United States Patent [19]

Johnson et al.

[11] Patent Number: 6,018,105
[45] Date of Patent: Jan. 25, 2000

[54] PROMOTERS FROM PLANT PROTOPORPHYRINOGEN OXIDASE GENES

[75] Inventors: Marie A. Johnson, Raleigh; Sandra L. Volrath; Eric R. Ward, both of Durham, all of N.C.

[73] Assignee: Novartis Finance Corporation, New York, N.Y.

[21] Appl. No.: 08/808,323

[22] Filed: Feb. 28, 1997

Related U.S. Application Data

[60] Provisional application No. 60/012,705, Feb. 28, 1996, provisional application No. 60/013,612, Feb. 28, 1996, and provisional application No. 60/020,003, Jun. 21, 1996.

[51] Int. Cl.[7] .............................. A01H 5/00; C07H 21/04; C12N 5/14; C12N 15/82
[52] U.S. Cl. ...................... 800/298; 435/320.1; 435/419; 536/24.1
[58] Field of Search ........................ 536/24.1; 435/320.1, 435/172.3, 419, 468; 800/205, DIG. 52, DIG. 15, DIG. 26, DIG. 55, DIG. 63, DIG. 27, DIG. 43, DIG. 9, DIG. 17, DIG. 56, DIG. 58, DIG. 57, 278, 298, 300, 312, 320, 314, 317.3, 306, 320.1, 320.3, 320.2

[56] References Cited

U.S. PATENT DOCUMENTS

| | | | |
|---|---|---|---|
| 5,086,169 | 2/1992 | Mascarenhas | 536/27 |
| 5,407,808 | 4/1995 | Halling et al. | 435/34 |
| 5,451,513 | 9/1995 | Maliga et al. | 435/122.3 |

FOREIGN PATENT DOCUMENTS

| | | |
|---|---|---|
| 0 360 750 | 9/1989 | European Pat. Off. . |
| 0 459 643 A2 | 5/1991 | European Pat. Off. . |
| 0 478 502 A2 | 4/1992 | European Pat. Off. . |
| WO 90/06748 | 6/1990 | WIPO . |
| WO 91/19418 | 12/1991 | WIPO . |
| WO 95/34659 | 12/1995 | WIPO . |
| WO 97/04088 | 2/1997 | WIPO . |
| WO 97/04089 | 2/1997 | WIPO . |
| WO 97/06250 | 2/1997 | WIPO . |

OTHER PUBLICATIONS

Benfey PN, et al. "The cauliflower mosaic virus 35S promoter: Combinatorial regulation of transcription in plants." Science 250: 959–966, Nov. 1990.

Kim Y, et al. "A 20 nucleotide upstream element is essential for the nopaline synthase (nos) promoter activity." Plant Mol. Biol. 24: 105–117, 1994.

Al–Hazimi et al., "Synthetic and Biosynthetic Studies of Porphyrins Part 7. The Action of Coproporphyrinogen Oxidase on Coproporphyrinogen IV: Syntheses of Protoporphyrin XIII, mesoporphyrin XIII, and Related Tricarboxylic Porphyrins", *J Chem Soc Perkin Trans. I*, 265–276 (1987).

Armbruster et al., "Herbicidal Action of Nitrophenyl Pyrazole Ether MON 12800: Immunolocalization, Ultrastructural, and Physiological Studies", *Pestice Biochemistry and Physiology*, 47: 21–35 (1993).

Becerril et al., "Acifluorfen Effects on Intermediates of Chlorophyll Synthesis in Green Cucumber Cotyledon Tissues", *Pesticide Biochemistry and Physiology*, 35: 119–126 (1989).

Brenner et al., "A Fluorometric Assay for Measurement of Protoporphyrinogen Oxidase Activity in Mammalian Tissue", *Clinica Chimica Acta*, 100: 259–266 (1980).

Brenner et al., "Cloning of murine ferrochelatase", *Proc. Natl. Acad. Sci. USA*, 88:849–853 (1991).

Camadro et al., "A New Assay for Protoporphyrinogen Oxidase—Evidence for a Total Deficiency in That Activity in a Heme–Less Mutant of *Saccharomyces cerevisiae*", *Biochemical and Biophysical Research Communications*, 106(3): 724–730 (1982).

Camadro et al., "Photoaffinity labeling of protoporphyrinogen oxidase, the molecular target of diphenylether–type herbicides", *Eur J of Biochem.*, 229: 669–674 (1995).

Camadro et al., "Molecular Properties of Yeast and Lettuce Protoporphyrinogen Oxidases", *Abstract Pap Am Chem. Soc.*, 111.(1–2) (1993).

Camadro et al., "Cloning and Characterization of the Yeast HEM14 Gene Codoing for Protoporphyrinogen Oxidase, the Molecular Target of Diphenyl Ether–type Herbicides", *The Journal of Biological Chemistry*, 271(15): 9120–9128 (1996).

Camadro et al., "Purification and Properties of Protoporphyrinogen Oxidase from the Yeast *Saccharomyces cerevisiae*: Mitochondrial Location and Evidence for a Precursor Form of the Protein", *The Journal of Biological Chemistry*, 269(51):32085–32091 (1994).

Cardin et al., "Characterization of Protoporphyrinogen Oxidase from *Rhodopseudomonas capsulata*", Abstracts of the Annual Meeting Am. Soc. Microbiol., Abstract #K–85, 207 (1986).

Che et al., "Localization of Target–Site of the Protoporphyrinogen Oxidase–Inhibiting Herbicide S–23142 in *Spinacia– oleracea* L.", *Z. Naturforsch.*, 48(c): 350–355 (1993).

Corrigall et al., "Inhibition of Mammalian Protoporphyrinogen Oxidase by Acifluorfen", *Biochemistry and Molecular Biology International*, 34(6): 1283–1289 (1994).

(List continued on next page.)

*Primary Examiner*—Lynette R. F. Smith
*Assistant Examiner*—Amy J. Nelson
*Attorney, Agent, or Firm*—J. Timothy Meigs; Larry W. Stults; Edouard G. Lebel

[57] ABSTRACT

Promoters naturally associated with plant protoporphyrinogen oxidase (protox) coding sequences, and derivatives thereof, are provided. These promoters can be used to control the expression of an operably linked heterologous coding sequence in a plant cell. These promoters are particularly useful for expressing modified forms of herbicide target enzymes, particularly modified forms of protox, to achieve tolerance to herbicides that inhibit the corresponding unmodified enzymes. Recombinant DNA molecules and chimeric genes comprising these promoters are provided, as well as plant tissue and plants containing such chimeric genes.

19 Claims, No Drawings

OTHER PUBLICATIONS

Crews et al., "Synthesis and Herbicidal Activity of bis–Aryloxybenzenes, a new Class of Protox Inhibitors", *Abstracts of Papers American Chemical Society*, Abstract #044. 209(1–2) (1995).

Dailey T.A. et al., "Human protoporphyrinogen oxidase: Expression, purification, and characterization of the cloned enzyme", *Protein Science*, 5: 98–105 (1996).

Dailey et al., "Expression of a Cloned Protoporphyrinogen Oxidase", *The Journal of Biological Chemistry*, 269(2):813–815 (1994).

Dailey T.A. et al., "Cloning, Sequence, and Expression of Mouse Protoporphyrinogen Oxidase", *Archives of Biochemistry and Biophysics*, 324(2): 379–384 (1995).

Derrick, Peter Michael, "An investigation into the mode of action of the herbicide M&B 39279", *Dissertation Abstracts International*, 50(10): 4283–B (1996).

Deybach et al., "The mitochondrial location of protoporphyrinogen oxidase", *Eur. J. Biochem.*, 149(2): 431–436 (1985).

Duke et al., "Protoporphyrinogen Oxidase as the Optimal Herbicide Site in the Porphyrin Pathway", ACS Symp. Ser.—*Porphyric Pesticides* 191–204 (1994).

Duke et al., "Protoporphyrinogen Oxidase–Inhibiting Herbicides", *Weed Science*, 39:465–473 (1991).

Duke et al., "Porphyric Pesticides Chemistry, Toxicology, and Pharmaceutical Applications", ACS Symposium Series 559, *American Chemical Society*, 1–318 (1994).

Duke et al., "Prospects for Herbicides Designed for Sites of Action in the Porphyrin Pathway Beyond Protoporphyrinogen Oxidase", *Abstracts of Papers American Chemical Society*, Abstract #129, 206(1–2) (1993).

Duke, S.O., "Pesticides that act Through Prophyrin Accumulation", Abstracts of the 22nd Annual Meeting of the American Society for Photobiology, Abstract #SPM–B2, 59 (Spec. Issue) (1994).

Elder et al., "A Radiochemical Method for the Measurement of Coproporphyrinogen Oxidase and the Utilization of Substrates other than Coproporphyrinogen III by the Enzyme from Rat Liver", *Biochem. J.*, 169: 205–214 (1978).

Falbel et al., "Characterization of a Family of Chlorophyll–Deficient Wheat (Triticum) and Barley (*Hordeum vulgare*) Mutants with Defects in the Magnesium–Insertion Step of Chlorophyll Biosynthesis", *Plant Physiology* (Rockville), 104: 639–648 (1994).

Ferreira et al., "Organization of the Terminal Two Enzymes of the Heme Biosynthetic Pathway Orientation of Protoporphyrinogen Oxidase and Evidence for a Membrane Complex", *The Journal of Biolocial Chemistry*, 263(8): 3835–3839 (1988).

Frustaci et al., "The *Escherichia–coli vis* A Gene Encodes Ferrochelatase, the Final Enzyme of the Heme Biosynthetic Pathway", *Journal of Bacteriology*, 175(7): 2154–2156 (1993).

Gollub et al., "Yeast Mutants Deficient in Heme Biosynthesis and a Heme Mutant Additionally Blocked in Cyclization of 2 3 Oxidosqualene", *The Journal of Biological Chemistry*, 252(9): 2846–2854 (1977).

Guo et al., "High–performance liquid chromatographic assays for protoporphyrinogen oidase and ferrochelatase in human leukocytes", *Journal of Chromatography Biomedical Applications*, 566: 383–396 (1991).

Hallahan et al., "Mode of Action Studies on a Chiral Diphenyl Ether Peroxidizing Herbicide Correlation between Differential Inhibition of Protoporphyrinogen IX Oxidase Activity and Induction of Tetrapyrrole Accumulation by the Enantiomers", *Plant Physiol.* (Bethesda), 100: 1211–1216 (1992).

Hansson et al., "Cloning and Characterization of the *Bacillus subtilis* hemEHY Gene Cluster, Which Encodes Protoheme IX Biosynthetic Enzymes", *J. Bacteriol.* 174(24) 8081–8093 (1992).

Hansson et al., "*Bacillus subtilis* Hem Y Is a Peripheral Membrane Protein Essential for Protoheme IX Synthesis Which Can Oxidize Coproporphyrinogen III and Protoporphyrinogen IX", *Journal of Bacteriology*, 176(19): 5962–5970 (1994).

Ihara et al., "Peroxidizing Phytotoxic Activity of 1,3, 4–Thiadiazolidine–2–thiones and 1,2,4–Triazolidine–3, 5–dithiones", *Journal of Pesticide Science*, 20: 41–47 (1995).

Iida et al., "Isomerization and Peroxidizing Phytotoxicity of Thiadiazolidine–thione Compounds", *Z. Naturforsch.*, 50(c): 186–192 (1995).

Jacobs et al., "Oxidation of protoporphyrinogen to protoporphyrin, a step in chlorophyll and haem biosynthesis", *Biochem J.*, 244: 219–224 (1987).

Jacobs J. M. et al., "Terminal Enzymes of Heme Biosynthesis in the Plant Plasma Membrane", *Archives of Biochemistry and Biophysics*, 323(2): 274–278 (1995).

Jacobs J.M. et al., "Effects of Diphenyl Dther Herbicides on Porphyrin Accumulation by Cultured Hepatocytes", *J. Biochem. Toxicology*, 7(2): 87–95 (1992).

Jacobs J.M. et al., "Protoporphyrinogen Oxidation, an Enzymatic Step in Heme and Chlorophyll Synthesis: Partial Characterization of the Reaction in Plant Organelles and Comparison with Mammalian and Bacterial Systems[1]", *Archives of Biochemistry and Biophysics*, 229(1): 312–319 (1984).

Jacobs J.M. et al., "Effects of the Photobleaching Herbicide, Acifluorfen–methyl, on Protoporphyrinogen Oxidation in Barley Organelles, Soybean Root Mitochondria Soybean Root Nodules, and Bacteria", *Archives of Biochemistry and Biophysics*, 280(2):369–375 (1990).

Jacobs et al., "Effect of Diphenyl Ether Herbicides on Oxidation of Protoporphyrinogen to Protoporphyrin in Organellar and Plasma Membrane Enriched Fractions of Barley", *Plant Physiol.* (Bethesda), 97: 197–203 (1991).

Jacobs et al., "Porphyrin Accumulation and Export by Isolated Barley (*Hordeum–vulgare*) Plastids. Effect of Diphenyl Ether Herbicides", *Plant Physiol.* (Rockv), 101:1181–1188 (1993).

Jacobs N. et al., "Protoporphyrinogen oxidation in plants and rhizobia", *Plant Physiol.* (Bethesda), #1055 (4 Suppl.) (1989).

Jacobs N.J. et al., "Mechanism of Protoporphyrin IX Accumulation in Plant Cells Treated with Herbicides Inhibiting Protoporphyrinogen Oxidase", *Abstract Pap Am. Chem. Soc.*, Abstract #113, 206 (1–2) (1993).

Jacobs N.J. et al., "Microbial Oxidation of Protoporphyrinogen an Intermediate in Heme and Chlorophyll Biosynthesis", *Archives of Biochemistry and Biophysics*, 197(2): 396–403 (1979).

Jacobs N.J. et al., "Characteristics of Purified Protoporphyrinogen Oxidase from Barley", *Biochemical and Biophysical Research Communications*, 161(2): 790–796 (1989).

Jacobs N.J. et al., "Assay for Enzymatic Protoporphyrinogen Oxidation, a Late Step in Heme Synthesis", *Enzyme* (Basel), 28: 206–217 (1982).

Jacobs N.J. et al., "Protoporphyrinogen Oxidation, a Step in Heme Synthesis in Soybean Root Nodules and Free–Living Rhizobia", *Journal of Bacteriology*, 171(1):573–576 (1989).

Jansen et al., "Mode of Evolved Photooxidant Resistance to Herbicides and Xenobiotics", *Z. Naturforsch Sect. Biosci.*, 45(c): 463–469 (1990).

Kataoka et al., "Isolation and Partial Characterization of Mutant *Chlamydomas reinhardtii* Resistant to Herbicide S–23142", *J. Pesticide Sci.*, 15:499–451(1990).

Klemm et al., "Protoporphyrinogen oxidation coupled to nitrite reduction with membranes from *Desulfovibrio–gigas*", *FEMS Microbiology Letters*, 61: 61–64 (1989).

Klemm et al., "Purification and Properties of Protoporphyrinogen Oxidase from an Anaerobic Bacterium, *Desulfovibrio–gigas*", *Journal of Bacteriology*, 169(11): 5209–5215 (1987).

Kohno et al., "Peroxidizing Phytotoxic Activity of Pyrazoles", *Journal of Pesticide Science*, 20: 137–143 (1995).

Kolarov et al., "Rat Liver Protoporphyrinogen IX Oxidase: Site of Synthesis and Factor Influencing its Activity", *Biochemical and Biophysical Research Communications*, 116(2): 383–387 (1983).

Komives et al., "Mechanisms of Plant Tolerance to Phytodynamic Herbicides", *Abstract Pap Am. Chem. Soc.*, Abstract #128, 206(1–2) (1993).

Labbe et al., "Fluorometric assays for coproporphyrinogen oxidase and protoporphyrinogen oxidase", *Analytical Biochemistry*, 149: 248–260 (1985).

Labbe–Bois R., "The Ferrochetelase from *Saccharomyces–Cerevisiae*. Sequence, Disruption, and Expression of its Structural Gene HEM15", *The Journal of Biological Chemistry*, 265(13): 7278–7283 (1990).

Lee et al., "Cellular Localization of Protoporphyrinogen–Oxidizing Activities of Etiolated Barley (*Hordeum vulgare* L.) Leaves", *Plant Physiol.*, 102:881–889 (1993).

Lee et al., "Peroxidase Involvement in the Accumulation of Protoporphyrin IX in Acifluorfen–Methyl–Treated Plant Tissues", *Plant Physiology* (Rockville), 105(1 Suppl.): 125 (1994).

Lee H.J. et al., "Protoporphyrinogen IX–Oxidizing Activities Involved in the Mode of Action of Peroxidizing Herbicides", *Journal of Agricultural and Food Chemistry*, 42(11): 2610–2618 (1994).

Li et al., "An h.p.l.c. assay for protoporphyrinogen oxidase activity in rat liver", *Biochem. J.*, 243: 863–866 (1987).

Lyga et al., "Synthesis, Mechanism of Action, and QSAR of Herbicidal 3–Substituted–2–aryl–4,5,6,7–tetrahydroindazoles", *Pesticide Science*, 42: 29–36 (1994).

Madsen et al., "A soybean coproporphyrinogen oxidase gene is highly expressed in root nodules", *Plant Molecular Biology*, 23: 35–43, (1993).

Martasek et al., "Molecular cloning, sequencing, and functional expression of a cDNA encoding human coproporphyrinogen oxidase", *Proceedings of the National Academy of Sciences of the United States of America*, 91: 3024–3028 (1994).

Martasek et al., "Homozygous hereditary coproporphyria caused by an arginine to tryptophan substitution in coproporphyrinogen oxidase and common intragenic polymorphisms", *Human Molecular Genetics*, 3(3): 477–480 (1994).

Matringe et al., "Localization within Chloroplasts of Protoporphyrinogen Oxidase, the Target Enzyme for Diphenylether–like Herbicides", *The Journal of Biological Chemistry*, 267(7):4646–4651 (1992).

Matringe et al., "Protoporphyrinogen oxidase as a molecular target for diphenyl ether herbicides", *Biochem. J.*, 260:231–235 (1989).

Matringe et al., "Protoporphyrinogen oxidase inhibition by three peroxidizing herbicides: oxadiazon, LS 82–556 and M&B 39279", *FEBS Letters*, 245(1,2): 35–38 (1989).

Matringe et al., "Characterization of [$^3$H]acifluorfen binding to purified pea etioplasts, and evidence that protoporphyrinogen oxidase specifically binds acifluorfen", *Eur. J. Biochem.*, 209: 861–868 (1992).

Matsumoto et al., "Variation in Crop Response to Protoporphyrinogen Oxidase Inhibitors", *Abstract. Pap Am. Chem. Soc.*, Abstract #124, 206 (1–2) (1993).

Matsumoto et al., "A Rapid and Strong Inhibition of Protoporphyrinogen Oxidase from Several Plant Species by Oxyfluorfen", *Pesticide Biochemistry and Physiology*, 47: 113–118 (1993).

Mullet, John E., "Dynamic Regulation of Chloroplast Transcription", *Plant Physiology*, 103: 309–313 (1993).

Nakayashiki et al., "Cloning and sequencing of a previously unidentified gene that is involved in the biosynthesis of heme in *Escherichia coli*", *Gene* (Amsterdam), 153: 67–70 (1995).

Nandihalli et al., "The Porphyrin Pathway as a H erbicide Target Site", *Abstract Pap Am. Chem. Soc.*, 203 (1–3) (1992).

Nandihalli et al., "Relationships between Molecular Properties and Biological Activities of O–Phenyl Pyrrolidino– and Piperidinocarbamate Herbicides", *J. Agri. Food Chem.*, 40(10): 1993–2000 (1992).

Nandihalli et al., "Correlation of Protoporphyrinogen Oxidase Inhibition by O–Phenyl Pyrrolidino– and Piperidino–Carbamates with their Herbicidal Effects", *Pestic. Sci.*, 35:227–235 (1992).

Nandihalli et al., "Enantioselectivity of Protophorphyrinogen Oxidase–Inhibiting Herbicides", *Pesticide Science*, 40: 265–277 (1994).

Nicolaus et al., "Binding Affinities of Peroxidizing Herbicides to Protoporphyrinogen Oxidase from Corn", *Pesticide Biochemistry and Physiology*, 51: 20–29 (1995).

Nicolaus et al., "Molecular Aspects of Herbicide Action on Protoporphyrinogen Oxidase", *Z. Naturforsch.*, 48(c): 326–333 (1993).

Nishimura et al., "Cloning of a Human cDNA for Protoporphyrinogen Oxidase by Complementation in Vivo of a hemG Mutant of *Escherichia coli*", *J. of Biological Chemistry*, 270(14): 8076–8080 (1995).

Oshio et al., "Isolation and Characterization of a *Chlamydomonas reinhardtii* Mutant Resistant to Photobleaching Herbicides", *Z. Naturforsch.* 48c: 339–344 (1993).

Pornprom et al., "Chracterization of Oxyfluorfen Tolerance in Selected Soybean Cell Line", *Pesticide Biochemistry and Physiology* 50: 107–114 (1994).

Pornprom et al., "Selection for Herbicide Tolerance in Soybean Using Cell Suspension Culture", *Weed Research*, 39(2): 102–108 (1994).

Prasad A.R.K. et al., "Generation of Resistance to the Diphenyl Ether Herbicide Acifluorfen by Mel Cells", *Biochemical and Biophysical Research Communications*, 215(1): 186–191 (1995).

Proulx et al., "Characteristics of murine protoporphyrinogen oxidase", *Protein Science,* 1: 801–809 (1992).

Proulx et al., "In situ conversion of coproporphyrinogen to heme by murine mitochondria: Terminal steps of the heme biosynthetic pathway", *Protein Science,* 2:1092–1098 (1993).

Ramseier et al., "Cloning of a DNA region from *Bradyrhizobium–japonicum* encoding pleiotropic functions in the heme metabolism and respiration", *Arch. Microbiol.,* 151:203–212 (1989).

Reddy K.N., "Modulators of the Porphyrin Pathway Beyond Protox", *Abstract Pap. Am. Chem. Soc.,* Abstract #127, 206(1–2) (1993).

Roberts et al., "Partial characterization and assignment of the gene for protoporphyrinogen oxidase and variegate porphyria to human chromosome 1q23", *Human Molecular Genetics,* 4(12): 2387–2390 (1995).

Sato et al., "Isomerization and Peroxidizing Phytotoxicity of Thiadiazolidine Herbicides", *Z. Naturforsch.,* 49(c): 49–56 (1994).

Sasarman et al., "Nucleotide sequence of the hemG gene involved in the protoporphyrinogen oxidase activity of *Escherichia coli* K12", *Can. J. Microbiol.,* 39:1155–1161 (1993).

Scalla et al., "Inhibitors of Protoporphyrinogen Oxidase as Herbicides: Diphenyl Ethers and Related Photobleaching Molecules", *Reviews of Weed Science,* 6: 103–132 (1994).

Sherman et al., "Tissue and Cellular Localization of Porphyrins in Cucumber Cotyledon Tissue with Inhibited Protoporphyrinogen Oxidase", *Plant Physiol.* (Bethesda), 93 (1Suppl.) (1990).

Sherman et al., "Pyrazole Phenyl Ether Herbicides Inhibit Protoporphyrinogen Oxidase", *Pesticide Biochemistry and Physiology,* 40: 236–245 (1991).

Sherman et al., "Physiological Basis for Differential Sensitivities of Plant Species to Protoporphyrinogen Oxidase–Inhibiting Herbicides", *Plant Physiol.* 97: 280–287 (1991).

Shibata et al., "Isolation and Characterization of a *Chlamydomonas reinhardtii* Mutant Resistant to an Experimental Herbicide S–23142, Which Inhibits Chlorophyll Synthesis", *Research in Photosynthesis,* III:567–570 (1992).

Shimizu et al., "A Novel Isourazole Herbicide, Fluthiacet- –Methyl, is a Potent Inhibitor of Protoporphyrinogen Oxidase after Isomerization by Glutathione S–Transferase", *Plant and Cell Physiology,* 36(4): 625–632 (1995).

Siepker et al., "Purification of bovine protoporphyrinogen oxidase: immunological cross–reactivity and structural relationship ferrochelatase", *Biochimica et Biophysica Acta,* 931: 349–358 (1987).

Smith et al., "Investigation of the subcellular location of the tetrapyrrole–biosynthesis enzyme coproporphyrinogen oxidase in higher pants", *Biochem. J.,* 292: 503–508 (1993).

Staub et al., "Long Regions og Homologous DNA Are Incorporated into the Tobacco Plastid Genome by Transformation", *The Plant Cell,* 4: 39–45 (1992).

Struhl, "They new yeast genetics", *Nature* 305:3 91–397 (1983).

Svab et al., "High–frequency plastid transformationin tobacco by selection for a chimeric aadA gene", *Proc. Natl. Acad. Sci. USA,* 90: 913–917 (1993).

Taketani et al., "The Human Protoporphyrinogen Oxidase Gene (PPOX): Organization and Location to Chromosome 1", *Genomics,* 29: 698–703 (1995).

Tietjen K.G., "Quinone Activation of Protoporphyrinogen Oxidase of Barley Plastids", *Pestic. Sci.,* 33: 467–471 (1991).

Tonkyn et al., "Differential expression of the partially duplicated chloroplast S10 ribosomal operon", *Mol Gen Genet,* 241: 141–152 (1993).

Troup et al., "Isolation of the hemF Operon Containing the Gene for the *Escherichia coli* Aerobic Coproporphyrinogen III Oxidase by In Vivo Complementation of a Yeast HEM13 Mutant", *Journal of Bacteriology,* 176(3): 673–680 (1994).

Troup et al., "Cloning and Characterization of the *Escherichia coli* hemN Gene Encoding the Oxygen–Independent Coproporphyrinogen III Oxidase", *Journal of Bacteriology,* 177(11): 3326–3331 (1995).

Varsano et al., "Competitive interaction of three peroxidizing herbicides with the binding of [$^3$ H]acifluorfen to corn etioplast membranes", *FEBS,* 272(1,2): 106–108 (1990).

Viljoen et al., "Protoporphyrinogen oxidase and ferrochelatase in porphyria variegata", *European Journal of Clinical Investigation,* 13: 283–287 (1983).

Wang et al., "New Assay Method for Protoporphyrinogen Oxidase Inhibitors Using Chloroplasts Isolated from *Spinacia oleracea* L", *Bioscience Biotechnology and Biochemistry,* 57(12): 2205–2206 (1993).

Wepplo et al., "Synthesis and Herbicidal Activity of 5–Aryloxybenzisoxazole–3–Acetate Esters", *Abstr. Pap. Am. Chem. Soc.,* Abstract #16, 205(1–2) (1993).

Witkowski et al., "Inhibition of Plant Protoporphyrinogen Oxidase by the Herbicide Acifluorfen–Methyl", *Plant Physiol.* (Bethesda), 90: 1239–1242 (1989).

Wright et al., "Herbicidal Activity of UCC–C4243 and Acifluorfen Is Due to Inhibition of Protoporphyrinogen Oxidase", *Weed Science,* 43: 47–54 (1995).

Xu et al., "The Genes Required for Heme Synthesis in *Salmonella–typhimurium* Include Those Encoding Alternative Functions for Aerobic and Anaerobic Coproporphyrinogen Oxidation", *Journal of Bacteriology,* 174(12): 3953–3963 (1992).

Xu et al., "An Oxygen–Dependent Coproporphyrinogen Oxidase Encoded by the hemF Gene of *Salmonella–typhimurium*", *Journal of Bacteriology,* 175(16): 4990–4999 (1993).

Yamato et al., "A Tobacco Soluble Protoporphyrinogen–oxidizing Enzyme Similar to Plant Peroxidases in Their Amino Acid Sequences and Immunochemical Reactivity", *Bioscience Biotechnology and Biochemistry,* 59(3): 558–559 (1995).

Yamato et al., "Purification and characterization of a protoporphyrinogen–oxidizing enzyme with peroxidase activity and light–dependent herbicide resistance in tobacco cultured cells", *Pestic. Biochem. Physiol.,* 50: 72–82 (1994).

EMBL Sequence Database Acc. No. M22063 Rel. No. 19, Apr. 22, 1989.

EMBL Sequence Database Acc. No. T43573, Rel. No. 42, Feb. 3, 1995.

Ichinose et al., "Selection and Characterization of Protoporphyrinogen Oxidase Inhibiting Herbicide (S23142) Resistant Photomixotrophic Cultured Cells of *Nicotiana tabacum*", *J. Plant Physiol.,* 146: 693–698 (1995).

SEQUENCE LISTING (1) GENERAL INFORMATION:

(iii) NUMBER OF SEQUENCES: 26

(2) INFORMATION FOR SEQ ID NO:1:

(i) SEQUENCE CHARACTERISTICS:
      (A) LENGTH: 1719 base pairs
      (B) TYPE: nucleic acid
      (C) STRANDEDNESS: single
      (D) TOPOLOGY: linear (ii) MOLECULE TYPE: cDNA (iii) HYPOTHETICAL: NO (iv) ANTI-SENSE: NO (vi) ORIGINAL SOURCE:
      (A) ORGANISM: Arabidopsis thaliana (vii) IMMEDIATE SOURCE:
      (B) CLONE: pWDC-2 (NRRL B-21238)

(ix) FEATURE:
      (A) NAME/KEY: CDS
      (B) LOCATION: 31..1644
      (D) OTHER INFORMATION: /product= "Arabidopsis protox-1"

(xi) SEQUENCE DESCRIPTION: SEQ ID NO:1:

```
TGACAAAATT CCGAATTCTC TGCGATTTCC ATG GAG TTA TCT CTT CTC CGT CCG         54
                                Met Glu Leu Ser Leu Leu Arg Pro
                                 1               5

ACG ACT CAA TCG CTT CTT CCG TCG TTT TCG AAG CCC AAT CTC CGA TTA         102
Thr Thr Gln Ser Leu Leu Pro Ser Phe Ser Lys Pro Asn Leu Arg Leu
     10              15                  20

AAT GTT TAT AAG CCT CTT AGA CTC CGT TGT TCA GTG GCC GGT GGA CCA         150
Asn Val Tyr Lys Pro Leu Arg Leu Arg Cys Ser Val Ala Gly Gly Pro
 25              30                  35                  40
```

| | |
|---|---|
| ACC GTC GGA TCT TCA AAA ATC GAA GGC GGA GGA GGC ACC ACC ATC ACG<br>Thr Val Gly Ser Ser Lys Ile Glu Gly Gly Gly Gly Thr Thr Ile Thr<br>                  45                  50                55 | 198 |
| ACG GAT TGT GTG ATT GTC GGC GGA GGT ATT AGT GGT CTT TGC ATC GCT<br>Thr Asp Cys Val Ile Val Gly Gly Gly Ile Ser Gly Leu Cys Ile Ala<br>                  60                  65                70 | 246 |
| CAG GCG CTT GCT ACT AAG CAT CCT GAT GCT GCT CCG AAT TTA ATT GTG<br>Gln Ala Leu Ala Thr Lys His Pro Asp Ala Ala Pro Asn Leu Ile Val<br>        75                  80                85 | 294 |
| ACC GAG GCT AAG GAT CGT GTT GGA GGC AAC ATT ATC ACT CGT GAA GAG<br>Thr Glu Ala Lys Asp Arg Val Gly Gly Asn Ile Ile Thr Arg Glu Glu<br>90                  95                100 | 342 |
| AAT GGT TTT CTC TGG GAA GAA GGT CCC AAT AGT TTT CAA CCG TCT GAT<br>Asn Gly Phe Leu Trp Glu Glu Gly Pro Asn Ser Phe Gln Pro Ser Asp<br>105              110                115            120 | 390 |
| CCT ATG CTC ACT ATG GTG GTA GAT AGT GGT TTG AAG GAT GAT TTG GTG<br>Pro Met Leu Thr Met Val Val Asp Ser Gly Leu Lys Asp Asp Leu Val<br>                  125                130            135 | 438 |
| TTG GGA GAT CCT ACT GCG CCA AGG TTT GTG TTG TGG AAT GGG AAA TTG<br>Leu Gly Asp Pro Thr Ala Pro Arg Phe Val Leu Trp Asn Gly Lys Leu<br>                  140                145            150 | 486 |
| AGG CCG GTT CCA TCG AAG CTA ACA GAC TTA CCG TTC TTT GAT TTG ATG<br>Arg Pro Val Pro Ser Lys Leu Thr Asp Leu Pro Phe Phe Asp Leu Met<br>            155                160                165 | 534 |
| AGT ATT GGT GGG AAG ATT AGA GCT GGT TTT GGT GCA CTT GGC ATT CGA<br>Ser Ile Gly Gly Lys Ile Arg Ala Gly Phe Gly Ala Leu Gly Ile Arg<br>        170                175                180 | 582 |
| CCG TCA CCT CCA GGT CGT GAA GAA TCT GTG GAG GAG TTT GTA CGG CGT<br>Pro Ser Pro Pro Gly Arg Glu Glu Ser Val Glu Glu Phe Val Arg Arg<br>185                  190                195            200 | 630 |
| AAC CTC GGT GAT GAG GTT TTT GAG CGC CTG ATT GAA CCG TTT TGT TCA<br>Asn Leu Gly Asp Glu Val Phe Glu Arg Leu Ile Glu Pro Phe Cys Ser<br>                  205                210            215 | 678 |
| GGT GTT TAT GCT GGT GAT CCT TCA AAA CTG AGC ATG AAA GCA GCG TTT<br>Gly Val Tyr Ala Gly Asp Pro Ser Lys Leu Ser Met Lys Ala Ala Phe<br>            220                225                230 | 726 |
| GGG AAG GTT TGG AAA CTA GAG CAA AAT GGT GGA AGC ATA ATA GGT GGT<br>Gly Lys Val Trp Lys Leu Glu Gln Asn Gly Gly Ser Ile Ile Gly Gly<br>        235                240                245 | 774 |
| ACT TTT AAG GCA ATT CAG GAG AGG AAA AAC GCT CCC AAG GCA GAA CGA<br>Thr Phe Lys Ala Ile Gln Glu Arg Lys Asn Ala Pro Lys Ala Glu Arg<br>250                  255                260 | 822 |
| GAC CCG CGC CTG CCA AAA CCA CAG GGC CAA ACA GTT GGT TCT TTC AGG<br>Asp Pro Arg Leu Pro Lys Pro Gln Gly Gln Thr Val Gly Ser Phe Arg<br>265                  270                275            280 | 870 |
| AAG GGA CTT CGA ATG TTG CCA GAA GCA ATA TCT GCA AGA TTA GGT AGC<br>Lys Gly Leu Arg Met Leu Pro Glu Ala Ile Ser Ala Arg Leu Gly Ser<br>                  285                290            295 | 918 |
| AAA GTT AAG TTG TCT TGG AAG CTC TCA GGT ATC ACT AAG CTG GAG AGC<br>Lys Val Lys Leu Ser Trp Lys Leu Ser Gly Ile Thr Lys Leu Glu Ser<br>        300                305                310 | 966 |
| GGA GGA TAC AAC TTA ACA TAT GAG ACT CCA GAT GGT TTA GTT TCC GTG<br>Gly Gly Tyr Asn Leu Thr Tyr Glu Thr Pro Asp Gly Leu Val Ser Val<br>            315                320                325 | 1014 |
| CAG AGC AAA AGT GTT GTA ATG ACG GTG CCA TCT CAT GTT GCA AGT GGT<br>Gln Ser Lys Ser Val Val Met Thr Val Pro Ser His Val Ala Ser Gly<br>330                  335                340 | 1062 |
| CTC TTG CGC CCT CTT TCT GAA TCT GCT GCA AAT GCA CTC TCA AAA CTA<br>Leu Leu Arg Pro Leu Ser Glu Ser Ala Ala Asn Ala Leu Ser Lys Leu<br>345                  350                355            360 | 1110 |

-continued

| | | | | | | | | | | | | | | | |
|---|---|---|---|---|---|---|---|---|---|---|---|---|---|---|---|
| TAT | TAC | CCA | CCA | GTT | GCA | GCA | GTA | TCT | ATC | TCG | TAC | CCG | AAA | GAA | GCA | 1158
| Tyr | Tyr | Pro | Pro | Val | Ala | Ala | Val | Ser | Ile | Ser | Tyr | Pro | Lys | Glu | Ala |
| | | | 365 | | | | 370 | | | | 375 | | | | |
| ATC | CGA | ACA | GAA | TGT | TTG | ATA | GAT | GGT | GAA | CTA | AAG | GGT | TTT | GGG | CAA | 1206
| Ile | Arg | Thr | Glu | Cys | Leu | Ile | Asp | Gly | Glu | Leu | Lys | Gly | Phe | Gly | Gln |
| | | 380 | | | | | 385 | | | | | 390 | | | |
| TTG | CAT | CCA | CGC | ACG | CAA | GGA | GTT | GAA | ACA | TTA | GGA | ACT | ATC | TAC | AGC | 1254
| Leu | His | Pro | Arg | Thr | Gln | Gly | Val | Glu | Thr | Leu | Gly | Thr | Ile | Tyr | Ser |
| | | 395 | | | | | 400 | | | | | 405 | | | |
| TCC | TCA | CTC | TTT | CCA | AAT | CGC | GCA | CCG | CCC | GGA | AGA | ATT | TTG | CTG | TTG | 1302
| Ser | Ser | Leu | Phe | Pro | Asn | Arg | Ala | Pro | Pro | Gly | Arg | Ile | Leu | Leu | Leu |
| | 410 | | | | | 415 | | | | | 420 | | | | |
| AAC | TAC | ATT | GGC | GGG | TCT | ACA | AAC | ACC | GGA | ATT | CTG | TCC | AAG | TCT | GAA | 1350
| Asn | Tyr | Ile | Gly | Gly | Ser | Thr | Asn | Thr | Gly | Ile | Leu | Ser | Lys | Ser | Glu |
| 425 | | | | | 430 | | | | | 435 | | | | | 440 |
| GGT | GAG | TTA | GTG | GAA | GCA | GTT | GAC | AGA | GAT | TTG | AGG | AAA | ATG | CTA | ATT | 1398
| Gly | Glu | Leu | Val | Glu | Ala | Val | Asp | Arg | Asp | Leu | Arg | Lys | Met | Leu | Ile |
| | | | | 445 | | | | | 450 | | | | | 455 | |
| AAG | CCT | AAT | TCG | ACC | GAT | CCA | CTT | AAA | TTA | GGA | GTT | AGG | GTA | TGG | CCT | 1446
| Lys | Pro | Asn | Ser | Thr | Asp | Pro | Leu | Lys | Leu | Gly | Val | Arg | Val | Trp | Pro |
| | | | 460 | | | | 465 | | | | | 470 | | | |
| CAA | GCC | ATT | CCT | CAG | TTT | CTA | GTT | GGT | CAC | TTT | GAT | ATC | CTT | GAC | ACG | 1494
| Gln | Ala | Ile | Pro | Gln | Phe | Leu | Val | Gly | His | Phe | Asp | Ile | Leu | Asp | Thr |
| | | 475 | | | | | 480 | | | | | 485 | | | |
| GCT | AAA | TCA | TCT | CTA | ACG | TCT | TCG | GGC | TAC | GAA | GGG | CTA | TTT | TTG | GGT | 1542
| Ala | Lys | Ser | Ser | Leu | Thr | Ser | Ser | Gly | Tyr | Glu | Gly | Leu | Phe | Leu | Gly |
| | 490 | | | | | 495 | | | | | 500 | | | | |
| GGC | AAT | TAC | GTC | GCT | GGT | GTA | GCC | TTA | GGC | CGG | TGT | GTA | GAA | GGC | GCA | 1590
| Gly | Asn | Tyr | Val | Ala | Gly | Val | Ala | Leu | Gly | Arg | Cys | Val | Glu | Gly | Ala |
| 505 | | | | | 510 | | | | | 515 | | | | | 520 |
| TAT | GAA | ACC | GCG | ATT | GAG | GTC | AAC | AAC | TTC | ATG | TCA | CGG | TAC | GCT | TAC | 1638
| Tyr | Glu | Thr | Ala | Ile | Glu | Val | Asn | Asn | Phe | Met | Ser | Arg | Tyr | Ala | Tyr |
| | | | | 525 | | | | | 530 | | | | | 535 | |

AAG TAAATGTAAA ACATTAAATC TCCCAGCTTG CGTGAGTTTT ATTAAATATT  1691
Lys

TTGAGATATC CAAAAAAAAA AAAAAAAA  1719

(2) INFORMATION FOR SEQ ID NO:2:

(i) SEQUENCE CHARACTERISTICS:
        (A) LENGTH: 537 amino acids
        (B) TYPE: amino acid
        (D) TOPOLOGY: linear (ii) MOLECULE TYPE: protein (xi) SEQUENCE DESCRIPTION: SEQ ID NO:2:

Met Glu Leu Ser Leu Leu Arg Pro Thr Thr Gln Ser Leu Leu Pro Ser
 1               5                  10                  15

Phe Ser Lys Pro Asn Leu Arg Leu Asn Val Tyr Lys Pro Leu Arg Leu
                20                  25                  30

Arg Cys Ser Val Ala Gly Gly Pro Thr Val Gly Ser Ser Lys Ile Glu
            35                  40                  45

Gly Gly Gly Gly Thr Thr Ile Thr Thr Asp Cys Val Ile Val Gly Gly
        50                  55                  60

Gly Ile Ser Gly Leu Cys Ile Ala Gln Ala Leu Ala Thr Lys His Pro
65                  70                  75                  80

Asp Ala Ala Pro Asn Leu Ile Val Thr Glu Ala Lys Asp Arg Val Gly
                85                  90                  95

-continued

```
Gly Asn Ile Ile Thr Arg Glu Glu Asn Gly Phe Leu Trp Glu Glu Gly
            100                 105                 110

Pro Asn Ser Phe Gln Pro Ser Asp Pro Met Leu Thr Met Val Val Asp
        115                 120                 125

Ser Gly Leu Lys Asp Asp Leu Val Leu Gly Asp Pro Thr Ala Pro Arg
    130                 135                 140

Phe Val Leu Trp Asn Gly Lys Leu Arg Pro Val Pro Ser Lys Leu Thr
145                 150                 155                 160

Asp Leu Pro Phe Phe Asp Leu Met Ser Ile Gly Gly Lys Ile Arg Ala
                165                 170                 175

Gly Phe Gly Ala Leu Gly Ile Arg Pro Ser Pro Gly Arg Glu Glu
            180                 185                 190

Ser Val Glu Glu Phe Val Arg Arg Asn Leu Gly Asp Glu Val Phe Glu
        195                 200                 205

Arg Leu Ile Glu Pro Phe Cys Ser Gly Val Tyr Ala Gly Asp Pro Ser
    210                 215                 220

Lys Leu Ser Met Lys Ala Ala Phe Gly Lys Val Trp Lys Leu Glu Gln
225                 230                 235                 240

Asn Gly Gly Ser Ile Ile Gly Gly Thr Phe Lys Ala Ile Gln Glu Arg
                245                 250                 255

Lys Asn Ala Pro Lys Ala Glu Arg Asp Pro Arg Leu Pro Lys Pro Gln
            260                 265                 270

Gly Gln Thr Val Gly Ser Phe Arg Lys Gly Leu Arg Met Leu Pro Glu
        275                 280                 285

Ala Ile Ser Ala Arg Leu Gly Ser Lys Val Lys Leu Ser Trp Lys Leu
    290                 295                 300

Ser Gly Ile Thr Lys Leu Glu Ser Gly Gly Tyr Asn Leu Thr Tyr Glu
305                 310                 315                 320

Thr Pro Asp Gly Leu Val Ser Val Gln Ser Lys Ser Val Val Met Thr
                325                 330                 335

Val Pro Ser His Val Ala Ser Gly Leu Leu Arg Pro Leu Ser Glu Ser
            340                 345                 350

Ala Ala Asn Ala Leu Ser Lys Leu Tyr Tyr Pro Pro Val Ala Ala Val
        355                 360                 365

Ser Ile Ser Tyr Pro Lys Glu Ala Ile Arg Thr Glu Cys Leu Ile Asp
    370                 375                 380

Gly Glu Leu Lys Gly Phe Gly Gln Leu His Pro Arg Thr Gln Gly Val
385                 390                 395                 400

Glu Thr Leu Gly Thr Ile Tyr Ser Ser Ser Leu Phe Pro Asn Arg Ala
                405                 410                 415

Pro Pro Gly Arg Ile Leu Leu Leu Asn Tyr Ile Gly Gly Ser Thr Asn
            420                 425                 430

Thr Gly Ile Leu Ser Lys Ser Glu Gly Glu Leu Val Glu Ala Val Asp
        435                 440                 445

Arg Asp Leu Arg Lys Met Leu Ile Lys Pro Asn Ser Thr Asp Pro Leu
    450                 455                 460

Lys Leu Gly Val Arg Val Trp Pro Gln Ala Ile Pro Gln Phe Leu Val
465                 470                 475                 480

Gly His Phe Asp Ile Leu Asp Thr Ala Lys Ser Ser Leu Thr Ser Ser
                485                 490                 495

Gly Tyr Glu Gly Leu Phe Leu Gly Gly Asn Tyr Val Ala Gly Val Ala
            500                 505                 510

Leu Gly Arg Cys Val Glu Gly Ala Tyr Glu Thr Ala Ile Glu Val Asn
        515                 520                 525
```

```
Asn Phe Met Ser Arg Tyr Ala Tyr Lys
    530                 535
```

(2) INFORMATION FOR SEQ ID NO:3:

(i) SEQUENCE CHARACTERISTICS:
        (A) LENGTH: 1738 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Arabidopsis thaliana (vii) IMMEDIATE SOURCE:
        (B) CLONE: pWDC-1 (NRRL B-21237)

(ix) FEATURE:
        (A) NAME/KEY: CDS
        (B) LOCATION: 70..1596
        (D) OTHER INFORMATION: /product= "Arabidopsis protox-2"

(xi) SEQUENCE DESCRIPTION: SEQ ID NO:3:

```
TTTTTTACTT ATTTCCGTCA CTGCTTTCGA CTGGTCAGAG ATTTTGACTC TGAATTGTTG        60

CAGATAGCA ATG GCG TCT GGA GCA GTA GCA GAT CAT CAA ATT GAA GCG          108
          Met Ala Ser Gly Ala Val Ala Asp His Gln Ile Glu Ala
          1               5                   10

GTT TCA GGA AAA AGA GTC GCA GTC GTA GGT GCA GGT GTA AGT GGA CTT        156
Val Ser Gly Lys Arg Val Ala Val Val Gly Ala Gly Val Ser Gly Leu
 15                  20                  25

GCG GCG GCT TAC AAG TTG AAA TCG AGG GGT TTG AAT GTG ACT GTG TTT        204
Ala Ala Ala Tyr Lys Leu Lys Ser Arg Gly Leu Asn Val Thr Val Phe
 30                  35                  40                  45

GAA GCT GAT GGA AGA GTA GGT GGG AAG TTG AGA AGT GTT ATG CAA AAT        252
Glu Ala Asp Gly Arg Val Gly Gly Lys Leu Arg Ser Val Met Gln Asn
                 50                  55                  60

GGT TTG ATT TGG GAT GAA GGA GCA AAC ACC ATG ACT GAG GCT GAG CCA        300
Gly Leu Ile Trp Asp Glu Gly Ala Asn Thr Met Thr Glu Ala Glu Pro
         65                  70                  75

GAA GTT GGG AGT TTA CTT GAT GAT CTT GGG CTT CGT GAG AAA CAA CAA        348
Glu Val Gly Ser Leu Leu Asp Asp Leu Gly Leu Arg Glu Lys Gln Gln
     80                  85                  90

TTT CCA ATT TCA CAG AAA AAG CGG TAT ATT GTG CGG AAT GGT GTA CCT        396
Phe Pro Ile Ser Gln Lys Lys Arg Tyr Ile Val Arg Asn Gly Val Pro
 95                 100                 105

GTG ATG CTA CCT ACC AAT CCC ATA GAG CTG GTC ACA AGT AGT GTG CTC        444
Val Met Leu Pro Thr Asn Pro Ile Glu Leu Val Thr Ser Ser Val Leu
110                 115                 120                 125

TCT ACC CAA TCT AAG TTT CAA ATC TTG TTG GAA CCA TTT TTA TGG AAG        492
Ser Thr Gln Ser Lys Phe Gln Ile Leu Leu Glu Pro Phe Leu Trp Lys
                130                 135                 140

AAA AAG TCC TCA AAA GTC TCA GAT GCA TCT GCT GAA GAA AGT GTA AGC        540
Lys Lys Ser Ser Lys Val Ser Asp Ala Ser Ala Glu Glu Ser Val Ser
                145                 150                 155

GAG TTC TTT CAA CGC CAT TTT GGA CAA GAG GTT GTT GAC TAT CTC ATC        588
Glu Phe Phe Gln Arg His Phe Gly Gln Glu Val Val Asp Tyr Leu Ile
        160                 165                 170
```

| | | |
|---|---|---|
| GAC CCT TTT GTT GGT GGA ACA AGT GCT GCG GAC CCT GAT TCC CTT TCA<br>Asp Pro Phe Val Gly Gly Thr Ser Ala Ala Asp Pro Asp Ser Leu Ser<br>175                    180                  185 | | 636 |
| ATG AAG CAT TCT TTC CCA GAT CTC TGG AAT GTA GAG AAA AGT TTT GGC<br>Met Lys His Ser Phe Pro Asp Leu Trp Asn Val Glu Lys Ser Phe Gly<br>190                195                200                205 | | 684 |
| TCT ATT ATA GTC GGT GCA ATC AGA ACA AAG TTT GCT GCT AAA GGT GGT<br>Ser Ile Ile Val Gly Ala Ile Arg Thr Lys Phe Ala Ala Lys Gly Gly<br>              210                215                220 | | 732 |
| AAA AGT AGA GAC ACA AAG AGT TCT CCT GGC ACA AAA AAG GGT TCG CGT<br>Lys Ser Arg Asp Thr Lys Ser Ser Pro Gly Thr Lys Lys Gly Ser Arg<br>                225                230              235 | | 780 |
| GGG TCA TTC TCT TTT AAG GGG GGA ATG CAG ATT CTT CCT GAT ACG TTG<br>Gly Ser Phe Ser Phe Lys Gly Gly Met Gln Ile Leu Pro Asp Thr Leu<br>            240                245                250 | | 828 |
| TGC AAA AGT CTC TCA CAT GAT GAG ATC AAT TTA GAC TCC AAG GTA CTC<br>Cys Lys Ser Leu Ser His Asp Glu Ile Asn Leu Asp Ser Lys Val Leu<br>255                    260                265 | | 876 |
| TCT TTG TCT TAC AAT TCT GGA TCA AGA CAG GAG AAC TGG TCA TTA TCT<br>Ser Leu Ser Tyr Asn Ser Gly Ser Arg Gln Glu Asn Trp Ser Leu Ser<br>270                    275                280              285 | | 924 |
| TGT GTT TCG CAT AAT GAA ACG CAG AGA CAA AAC CCC CAT TAT GAT GCT<br>Cys Val Ser His Asn Glu Thr Gln Arg Gln Asn Pro His Tyr Asp Ala<br>                    290                295              300 | | 972 |
| GTA ATT ATG ACG GCT CCT CTG TGC AAT GTG AAG GAG ATG AAG GTT ATG<br>Val Ile Met Thr Ala Pro Leu Cys Asn Val Lys Glu Met Lys Val Met<br>              305                310                315 | | 1020 |
| AAA GGA GGA CAA CCC TTT CAG CTA AAC TTT CTC CCC GAG ATT AAT TAC<br>Lys Gly Gly Gln Pro Phe Gln Leu Asn Phe Leu Pro Glu Ile Asn Tyr<br>            320                325                330 | | 1068 |
| ATG CCC CTC TCG GTT TTA ATC ACC ACA TTC ACA AAG GAG AAA GTA AAG<br>Met Pro Leu Ser Val Leu Ile Thr Thr Phe Thr Lys Glu Lys Val Lys<br>335                    340                345 | | 1116 |
| AGA CCT CTT GAA GGC TTT GGG GTA CTC ATT CCA TCT AAG GAG CAA AAG<br>Arg Pro Leu Glu Gly Phe Gly Val Leu Ile Pro Ser Lys Glu Gln Lys<br>350                    355                360              365 | | 1164 |
| CAT GGT TTC AAA ACT CTA GGT ACA CTT TTT TCA TCA ATG ATG TTT CCA<br>His Gly Phe Lys Thr Leu Gly Thr Leu Phe Ser Ser Met Met Phe Pro<br>                    370                375              380 | | 1212 |
| GAT CGT TCC CCT AGT GAC GTT CAT CTA TAT ACA ACT TTT ATT GGT GGG<br>Asp Arg Ser Pro Ser Asp Val His Leu Tyr Thr Thr Phe Ile Gly Gly<br>              385                390                395 | | 1260 |
| AGT AGG AAC CAG GAA CTA GCC AAA GCT TCC ACT GAC GAA TTA AAA CAA<br>Ser Arg Asn Gln Glu Leu Ala Lys Ala Ser Thr Asp Glu Leu Lys Gln<br>            400                405                410 | | 1308 |
| GTT GTG ACT TCT GAC CTT CAG CGA CTG TTG GGG GTT GAA GGT GAA CCC<br>Val Val Thr Ser Asp Leu Gln Arg Leu Leu Gly Val Glu Gly Glu Pro<br>415                    420                425 | | 1356 |
| GTG TCT GTC AAC CAT TAC TAT TGG AGG AAA GCA TTC CCG TTG TAT GAC<br>Val Ser Val Asn His Tyr Tyr Trp Arg Lys Ala Phe Pro Leu Tyr Asp<br>430                    435                440              445 | | 1404 |
| AGC AGC TAT GAC TCA GTC ATG GAA GCA ATT GAC AAG ATG GAG AAT GAT<br>Ser Ser Tyr Asp Ser Val Met Glu Ala Ile Asp Lys Met Glu Asn Asp<br>                450                455              460 | | 1452 |
| CTA CCT GGG TTC TTC TAT GCA GGT AAT CAT CGA GGG GGG CTC TCT GTT<br>Leu Pro Gly Phe Phe Tyr Ala Gly Asn His Arg Gly Gly Leu Ser Val<br>              465                470              475 | | 1500 |
| GGG AAA TCA ATA GCA TCA GGT TGC AAA GCA GCT GAC CTT GTG ATC TCA<br>Gly Lys Ser Ile Ala Ser Gly Cys Lys Ala Ala Asp Leu Val Ile Ser<br>            480                485                490 | | 1548 |

```
TAC CTG GAG TCT TGC TCA AAT GAC AAG AAA CCA AAT GAC AGC TTA TAACATTG  1603
Tyr Leu Glu Ser Cys Ser Asn Asp Lys Lys Pro Asn Asp Ser Leu
495                 500                 505

AAGGTTCGTC CCTTTTTATC ACTTACTTTG TAAACTTGTA AAATGCAACA AGCCGCCGTG     1663

CGATTAGCCA ACAACTCAGC AAAACCCAGA TTCTCATAAG GCTCACTAAT TCCAGAATAA     1723

ACTATTTATG TAAAA                                                     1738
```

(2) INFORMATION FOR SEQ ID NO:4:

(i) SEQUENCE CHARACTERISTICS:
        (A) LENGTH: 508 amino acids
        (B) TYPE: amino acid
        (D) TOPOLOGY: linear (ii) MOLECULE TYPE: protein (xi) SEQUENCE DESCRIPTION: SEQ ID NO:4:

```
Met Ala Ser Gly Ala Val Ala Asp His Gln Ile Glu Ala Val Ser Gly
 1               5                  10                  15

Lys Arg Val Ala Val Gly Ala Gly Val Ser Gly Leu Ala Ala Ala
            20                  25                  30

Tyr Lys Leu Lys Ser Arg Gly Leu Asn Val Thr Val Phe Glu Ala Asp
            35                  40                  45

Gly Arg Val Gly Gly Lys Leu Arg Ser Val Met Gln Asn Gly Leu Ile
 50                  55                  60

Trp Asp Glu Gly Ala Asn Thr Met Thr Glu Ala Glu Pro Glu Val Gly
 65                  70                  75                  80

Ser Leu Leu Asp Asp Leu Gly Leu Arg Glu Lys Gln Gln Phe Pro Ile
            85                  90                  95

Ser Gln Lys Lys Arg Tyr Ile Val Arg Asn Gly Val Pro Val Met Leu
            100                 105                 110

Pro Thr Asn Pro Ile Glu Leu Val Thr Ser Ser Val Leu Ser Thr Gln
            115                 120                 125

Ser Lys Phe Gln Ile Leu Leu Glu Pro Phe Leu Trp Lys Lys Ser
            130                 135                 140

Ser Lys Val Ser Asp Ala Ser Ala Glu Glu Ser Val Ser Glu Phe Phe
145                 150                 155                 160

Gln Arg His Phe Gly Gln Glu Val Val Asp Tyr Leu Ile Asp Pro Phe
                165                 170                 175

Val Gly Gly Thr Ser Ala Ala Asp Pro Asp Ser Leu Ser Met Lys His
                180                 185                 190

Ser Phe Pro Asp Leu Trp Asn Val Glu Lys Ser Phe Gly Ser Ile Ile
            195                 200                 205

Val Gly Ala Ile Arg Thr Lys Phe Ala Ala Lys Gly Lys Ser Arg
210                 215                 220

Asp Thr Lys Ser Ser Pro Gly Thr Lys Lys Gly Ser Arg Gly Ser Phe
225                 230                 235                 240

Ser Phe Lys Gly Gly Met Gln Ile Leu Pro Asp Thr Leu Cys Lys Ser
                245                 250                 255

Leu Ser His Asp Glu Ile Asn Leu Asp Ser Lys Val Leu Ser Leu Ser
            260                 265                 270

Tyr Asn Ser Gly Ser Arg Gln Glu Asn Trp Ser Leu Ser Cys Val Ser
            275                 280                 285

His Asn Glu Thr Gln Arg Gln Asn Pro His Tyr Asp Ala Val Ile Met
            290                 295                 300
```

```
Thr Ala Pro Leu Cys Asn Val Lys Glu Met Lys Val Met Lys Gly Gly
305                 310                 315                 320

Gln Pro Phe Gln Leu Asn Phe Leu Pro Glu Ile Asn Tyr Met Pro Leu
            325                 330                 335

Ser Val Leu Ile Thr Thr Phe Thr Lys Glu Lys Val Lys Arg Pro Leu
            340                 345                 350

Glu Gly Phe Gly Val Leu Ile Pro Ser Lys Glu Gln Lys His Gly Phe
            355                 360                 365

Lys Thr Leu Gly Thr Leu Phe Ser Ser Met Met Phe Pro Asp Arg Ser
    370                 375                 380

Pro Ser Asp Val His Leu Tyr Thr Thr Phe Ile Gly Gly Ser Arg Asn
385                 390                 395                 400

Gln Glu Leu Ala Lys Ala Ser Thr Asp Glu Leu Lys Gln Val Val Thr
            405                 410                 415

Ser Asp Leu Gln Arg Leu Leu Gly Val Glu Gly Glu Pro Val Ser Val
            420                 425                 430

Asn His Tyr Tyr Trp Arg Lys Ala Phe Pro Leu Tyr Asp Ser Ser Tyr
            435                 440                 445

Asp Ser Val Met Glu Ala Ile Asp Lys Met Glu Asn Asp Leu Pro Gly
    450                 455                 460

Phe Phe Tyr Ala Gly Asn His Arg Gly Gly Leu Ser Val Gly Lys Ser
465                 470                 475                 480

Ile Ala Ser Gly Cys Lys Ala Ala Asp Leu Val Ile Ser Tyr Leu Glu
            485                 490                 495

Ser Cys Ser Asn Asp Lys Lys Pro Asn Asp Ser Leu
            500                 505

(2) INFORMATION FOR SEQ ID NO:5:

(i) SEQUENCE CHARACTERISTICS:
        (A) LENGTH: 1691 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Zea mays (maize)

(vii) IMMEDIATE SOURCE:
        (B) CLONE: pWDC-4 (NRRL B-21260)

(ix) FEATURE:
        (A) NAME/KEY: CDS
        (B) LOCATION: 1..1443
        (D) OTHER INFORMATION: /product= "Maize protox-1
            cDNA (not full-length); first seven nucleotides removed
                            vs. serial no. 60/012,705"

(xi) SEQUENCE DESCRIPTION: SEQ ID NO:5:

GCG GAC TGC GTC GTG GTG GGC GGA GGC ATC AGT GGC CTC TGC ACC GCG        48
Ala Asp Cys Val Val Val Gly Gly Gly Ile Ser Gly Leu Cys Thr Ala
 1               5                  10                  15

CAG GCG CTG GCC ACG CGG CAC GGC GTC GGG GAC GTG CTT GTC ACG GAG        96
Gln Ala Leu Ala Thr Arg His Gly Val Gly Asp Val Leu Val Thr Glu
            20                  25                  30

GCC CGC GCC CGC CCC GGC GGC AAC ATT ACC ACC GTC GAG CGC CCC GAG       144
Ala Arg Ala Arg Pro Gly Gly Asn Ile Thr Thr Val Glu Arg Pro Glu
        35                  40                  45
```

```
GAA GGG TAC CTC TGG GAG GAG GGT CCC AAC AGC TTC CAG CCC TCC GAC        192
Glu Gly Tyr Leu Trp Glu Glu Gly Pro Asn Ser Phe Gln Pro Ser Asp
 50                  55                  60

CCC GTT CTC ACC ATG GCC GTG GAC AGC GGA CTG AAG GAT GAC TTG GTT        240
Pro Val Leu Thr Met Ala Val Asp Ser Gly Leu Lys Asp Asp Leu Val
 65                  70                  75                  80

TTT GGG GAC CCA AAC GCG CCG CGT TTC GTG CTG TGG GAG GGG AAG CTG        288
Phe Gly Asp Pro Asn Ala Pro Arg Phe Val Leu Trp Glu Gly Lys Leu
                     85                  90                  95

AGG CCC GTG CCA TCC AAG CCC GCC GAC CTC CCG TTC TTC GAT CTC ATG        336
Arg Pro Val Pro Ser Lys Pro Ala Asp Leu Pro Phe Phe Asp Leu Met
                100                 105                 110

AGC ATC CCA GGG AAG CTC AGG GCC GGT CTA GGC GCG CTT GGC ATC CGC        384
Ser Ile Pro Gly Lys Leu Arg Ala Gly Leu Gly Ala Leu Gly Ile Arg
            115                 120                 125

CCG CCT CCT CCA GGC CGC GAA GAG TCA GTG GAG GAG TTC GTG CGC CGC        432
Pro Pro Pro Pro Gly Arg Glu Glu Ser Val Glu Glu Phe Val Arg Arg
130                 135                 140

AAC CTC GGT GCT GAG GTC TTT GAG CGC CTC ATT GAG CCT TTC TGC TCA        480
Asn Leu Gly Ala Glu Val Phe Glu Arg Leu Ile Glu Pro Phe Cys Ser
145                 150                 155                 160

GGT GTC TAT GCT GGT GAT CCT TCT AAG CTC AGC ATG AAG GCT GCA TTT        528
Gly Val Tyr Ala Gly Asp Pro Ser Lys Leu Ser Met Lys Ala Ala Phe
                165                 170                 175

GGG AAG GTT TGG CGG TTG GAA GAA ACT GGA GGT AGT ATT ATT GGT GGA        576
Gly Lys Val Trp Arg Leu Glu Glu Thr Gly Gly Ser Ile Ile Gly Gly
                180                 185                 190

ACC ATC AAG ACA ATT CAG GAG AGG AGC AAG AAT CCA AAA CCA CCG AGG        624
Thr Ile Lys Thr Ile Gln Glu Arg Ser Lys Asn Pro Lys Pro Pro Arg
            195                 200                 205

GAT GCC CGC CTT CCG AAG CCA AAA GGG CAG ACA GTT GCA TCT TTC AGG        672
Asp Ala Arg Leu Pro Lys Pro Lys Gly Gln Thr Val Ala Ser Phe Arg
210                 215                 220

AAG GGT CTT GCC ATG CTT CCA AAT GCC ATT ACA TCC AGC TTG GGT AGT        720
Lys Gly Leu Ala Met Leu Pro Asn Ala Ile Thr Ser Ser Leu Gly Ser
225                 230                 235                 240

AAA GTC AAA CTA TCA TGG AAA CTC ACG AGC ATT ACA AAA TCA GAT GAC        768
Lys Val Lys Leu Ser Trp Lys Leu Thr Ser Ile Thr Lys Ser Asp Asp
                245                 250                 255

AAG GGA TAT GTT TTG GAG TAT GAA ACG CCA GAA GGG GTT GTT TCG GTG        816
Lys Gly Tyr Val Leu Glu Tyr Glu Thr Pro Glu Gly Val Val Ser Val
                260                 265                 270

CAG GCT AAA AGT GTT ATC ATG ACT ATT CCA TCA TAT GTT GCT AGC AAC        864
Gln Ala Lys Ser Val Ile Met Thr Ile Pro Ser Tyr Val Ala Ser Asn
            275                 280                 285

ATT TTG CGT CCA CTT TCA AGC GAT GCT GCA GAT GCT CTA TCA AGA TTC        912
Ile Leu Arg Pro Leu Ser Ser Asp Ala Ala Asp Ala Leu Ser Arg Phe
290                 295                 300

TAT TAT CCA CCG GTT GCT GCT GTA ACT GTT TCG TAT CCA AAG GAA GCA        960
Tyr Tyr Pro Pro Val Ala Ala Val Thr Val Ser Tyr Pro Lys Glu Ala
305                 310                 315                 320

ATT AGA AAA GAA TGC TTA ATT GAT GGG GAA CTC CAG GGC TTT GGC CAG       1008
Ile Arg Lys Glu Cys Leu Ile Asp Gly Glu Leu Gln Gly Phe Gly Gln
                325                 330                 335

TTG CAT CCA CGT AGT CAA GGA GTT GAG ACA TTA GGA ACA ATA TAC AGT       1056
Leu His Pro Arg Ser Gln Gly Val Glu Thr Leu Gly Thr Ile Tyr Ser
                340                 345                 350

TCC TCA CTC TTT CCA AAT CGT GCT CCT GAC GGT AGG GTG TTA CTT CTA       1104
Ser Ser Leu Phe Pro Asn Arg Ala Pro Asp Gly Arg Val Leu Leu Leu
            355                 360                 365
```

```
AAC TAC ATA GGA GGT GCT ACA AAC ACA GGA ATT GTT TCC AAG ACT GAA     1152
Asn Tyr Ile Gly Gly Ala Thr Asn Thr Gly Ile Val Ser Lys Thr Glu
        370                 375                 380

AGT GAG CTG GTC GAA GCA GTT GAC CGT GAC CTC CGA AAA ATG CTT ATA     1200
Ser Glu Leu Val Glu Ala Val Asp Arg Asp Leu Arg Lys Met Leu Ile
385                 390                 395                 400

AAT TCT ACA GCA GTG GAC CCT TTA GTC CTT GGT GTT CGA GTT TGG CCA     1248
Asn Ser Thr Ala Val Asp Pro Leu Val Leu Gly Val Arg Val Trp Pro
                405                 410                 415

CAA GCC ATA CCT CAG TTC CTG GTA GGA CAT CTT GAT CTT CTG GAA GCC     1296
Gln Ala Ile Pro Gln Phe Leu Val Gly His Leu Asp Leu Leu Glu Ala
            420                 425                 430

GCA AAA GCT GCC CTG GAC CGA GGT GGC TAC GAT GGG CTG TTC CTA GGA     1344
Ala Lys Ala Ala Leu Asp Arg Gly Gly Tyr Asp Gly Leu Phe Leu Gly
                435                 440                 445

GGG AAC TAT GTT GCA GGA GTT GCC CTG GGC AGA TGC GTT GAG GGC GCG     1392
Gly Asn Tyr Val Ala Gly Val Ala Leu Gly Arg Cys Val Glu Gly Ala
        450                 455                 460

TAT GAA AGT GCC TCG CAA ATA TCT GAC TTC TTG ACC AAG TAT GCC TAC     1440
Tyr Glu Ser Ala Ser Gln Ile Ser Asp Phe Leu Thr Lys Tyr Ala Tyr
465                 470                 475                 480

AAG TGATGAAAGA AGTGGAGCGC TACTTGTTAA TCGTTTATGT TGCATAGATG          1493
Lys

AGGTGCCTCC GGGAAAAAAA AAGCTTGAAT AGTATTTTTT ATTCTTATTT TGTAAATTGC   1553

ATTTCTGTTC TTTTTTCTAT CAGTAATTAG TTATATTTTA GTTCTGTAGG AGATTGTTCT   1613

GTTCACTGCC CTTCAAAAGA AATTTTATTT TTCATTCTTT TATGAGAGCT GTGCTACTTA   1673

AAAAAAAAAA AAAAAAAA                                                 1691

(2) INFORMATION FOR SEQ ID NO:6:

(i) SEQUENCE CHARACTERISTICS:
        (A) LENGTH: 481 amino acids
        (B) TYPE: amino acid
        (D) TOPOLOGY: linear (ii) MOLECULE TYPE: protein (xi) SEQUENCE DESCRIPTION: SEQ ID NO:6:

Ala Asp Cys Val Val Gly Gly Gly Ile Ser Gly Leu Cys Thr Ala
1               5                   10                  15

Gln Ala Leu Ala Thr Arg His Gly Val Gly Asp Val Leu Val Thr Glu
            20                  25                  30

Ala Arg Ala Arg Pro Gly Gly Asn Ile Thr Thr Val Glu Arg Pro Glu
        35                  40                  45

Glu Gly Tyr Leu Trp Glu Glu Gly Pro Asn Ser Phe Gln Pro Ser Asp
    50                  55                  60

Pro Val Leu Thr Met Ala Val Asp Ser Gly Leu Lys Asp Asp Leu Val
65                  70                  75                  80

Phe Gly Asp Pro Asn Ala Pro Arg Phe Val Leu Trp Glu Gly Lys Leu
                85                  90                  95

Arg Pro Val Pro Ser Lys Pro Ala Asp Leu Pro Phe Phe Asp Leu Met
            100                 105                 110

Ser Ile Pro Gly Lys Leu Arg Ala Gly Leu Gly Ala Leu Gly Ile Arg
        115                 120                 125

Pro Pro Pro Pro Gly Arg Glu Glu Ser Val Glu Glu Phe Val Arg Arg
    130                 135                 140
```

```
Asn Leu Gly Ala Glu Val Phe Glu Arg Leu Ile Glu Pro Phe Cys Ser
145                 150                 155                 160

Gly Val Tyr Ala Gly Asp Pro Ser Lys Leu Ser Met Lys Ala Ala Phe
            165                 170                 175

Gly Lys Val Trp Arg Leu Glu Thr Gly Ser Ile Ile Gly Gly
            180                 185                 190

Thr Ile Lys Thr Ile Gln Glu Arg Ser Lys Asn Pro Lys Pro Pro Arg
        195                 200                 205

Asp Ala Arg Leu Pro Lys Pro Lys Gly Gln Thr Val Ala Ser Phe Arg
        210                 215                 220

Lys Gly Leu Ala Met Leu Pro Asn Ala Ile Thr Ser Ser Leu Gly Ser
225                 230                 235                 240

Lys Val Lys Leu Ser Trp Lys Leu Thr Ser Ile Thr Lys Ser Asp Asp
            245                 250                 255

Lys Gly Tyr Val Leu Glu Tyr Glu Thr Pro Glu Gly Val Val Ser Val
            260                 265                 270

Gln Ala Lys Ser Val Ile Met Thr Ile Pro Ser Tyr Val Ala Ser Asn
        275                 280                 285

Ile Leu Arg Pro Leu Ser Ser Asp Ala Ala Asp Ala Leu Ser Arg Phe
        290                 295                 300

Tyr Tyr Pro Pro Val Ala Ala Val Thr Val Ser Tyr Pro Lys Glu Ala
305                 310                 315                 320

Ile Arg Lys Glu Cys Leu Ile Asp Gly Glu Leu Gln Gly Phe Gly Gln
            325                 330                 335

Leu His Pro Arg Ser Gln Gly Val Glu Thr Leu Gly Thr Ile Tyr Ser
            340                 345                 350

Ser Ser Leu Phe Pro Asn Arg Ala Pro Asp Gly Arg Val Leu Leu Leu
        355                 360                 365

Asn Tyr Ile Gly Gly Ala Thr Asn Thr Gly Ile Val Ser Lys Thr Glu
        370                 375                 380

Ser Glu Leu Val Glu Ala Val Asp Arg Asp Leu Arg Lys Met Leu Ile
385                 390                 395                 400

Asn Ser Thr Ala Val Asp Pro Leu Val Leu Gly Val Arg Val Trp Pro
            405                 410                 415

Gln Ala Ile Pro Gln Phe Leu Val Gly His Leu Asp Leu Leu Glu Ala
            420                 425                 430

Ala Lys Ala Ala Leu Asp Arg Gly Gly Tyr Asp Gly Leu Phe Leu Gly
        435                 440                 445

Gly Asn Tyr Val Ala Gly Val Ala Leu Gly Arg Cys Val Glu Gly Ala
        450                 455                 460

Tyr Glu Ser Ala Ser Gln Ile Ser Asp Phe Leu Thr Lys Tyr Ala Tyr
465                 470                 475                 480

Lys
```

(2) INFORMATION FOR SEQ ID NO:7:

(i) SEQUENCE CHARACTERISTICS:
        (A) LENGTH: 2061 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
            (A) ORGANISM: Zea mays (maize)

(vii) IMMEDIATE SOURCE:
            (B) CLONE: pWDC-3 (NRRL B-21259)

(ix) FEATURE:
            (A) NAME/KEY: CDS
            (B) LOCATION: 64..1698
            (D) OTHER INFORMATION: /product= "Maize protox-2"

(xi) SEQUENCE DESCRIPTION: SEQ ID NO:7:

```
CTCTCCTACC TCCACCTCCA CGACAACAAG CAAATCCCCA TCCAGTTCCA AACCCTAACT        60

CAA ATG CTC GCT TTG ACT GCC TCA GCC TCA TCC GCT TCG TCC CAT CCT         108
    Met Leu Ala Leu Thr Ala Ser Ala Ser Ser Ala Ser Ser His Pro
    1               5                   10                  15

TAT CGC CAC GCC TCC GCG CAC ACT CGT CGC CCC CGC CTA CGT GCG GTC         156
Tyr Arg His Ala Ser Ala His Thr Arg Arg Pro Arg Leu Arg Ala Val
                20                  25                  30

CTC GCG ATG GCG GGC TCC GAC GAC CCC CGT GCA GCG CCC GCC AGA TCG         204
Leu Ala Met Ala Gly Ser Asp Asp Pro Arg Ala Ala Pro Ala Arg Ser
                35                  40                  45

GTC GCC GTC GTC GGC GCC GGG GTC AGC GGG CTC GCG GCG GCG TAC AGG         252
Val Ala Val Val Gly Ala Gly Val Ser Gly Leu Ala Ala Ala Tyr Arg
            50                  55                  60

CTC AGA CAG AGC GGC GTG AAC GTA ACG GTG TTC GAA GCG GCC GAC AGG         300
Leu Arg Gln Ser Gly Val Asn Val Thr Val Phe Glu Ala Ala Asp Arg
        65                  70                  75

GCG GGA GGA AAG ATA CGG ACC AAT TCC GAG GGC GGG TTT GTC TGG GAT         348
Ala Gly Gly Lys Ile Arg Thr Asn Ser Glu Gly Gly Phe Val Trp Asp
80                  85                  90                  95

GAA GGA GCT AAC ACC ATG ACA GAA GGT GAA TGG GAG GCC AGT AGA CTG         396
Glu Gly Ala Asn Thr Met Thr Glu Gly Glu Trp Glu Ala Ser Arg Leu
                100                 105                 110

ATT GAT GAT CTT GGT CTA CAA GAC AAA CAG CAG TAT CCT AAC TCC CAA         444
Ile Asp Asp Leu Gly Leu Gln Asp Lys Gln Gln Tyr Pro Asn Ser Gln
            115                 120                 125

CAC AAG CGT TAC ATT GTC AAA GAT GGA GCA CCA GCA CTG ATT CCT TCG         492
His Lys Arg Tyr Ile Val Lys Asp Gly Ala Pro Ala Leu Ile Pro Ser
        130                 135                 140

GAT CCC ATT TCG CTA ATG AAA AGC AGT GTT CTT TCG ACA AAA TCA AAG         540
Asp Pro Ile Ser Leu Met Lys Ser Ser Val Leu Ser Thr Lys Ser Lys
145                 150                 155

ATT GCG TTA TTT TTT GAA CCA TTT CTC TAC AAG AAA GCT AAC ACA AGA         588
Ile Ala Leu Phe Phe Glu Pro Phe Leu Tyr Lys Lys Ala Asn Thr Arg
160                 165                 170                 175

AAC TCT GGA AAA GTG TCT GAG GAG CAC TTG AGT GAG AGT GTT GGG AGC         636
Asn Ser Gly Lys Val Ser Glu Glu His Leu Ser Glu Ser Val Gly Ser
                180                 185                 190

TTC TGT GAA CGC CAC TTT GGA AGA GAA GTT GTT GAC TAT TTT GTT GAT         684
Phe Cys Glu Arg His Phe Gly Arg Glu Val Val Asp Tyr Phe Val Asp
            195                 200                 205

CCA TTT GTA GCT GGA ACA AGT GCA GGA GAT CCA GAG TCA CTA TCT ATT         732
Pro Phe Val Ala Gly Thr Ser Ala Gly Asp Pro Glu Ser Leu Ser Ile
        210                 215                 220

CGT CAT GCA TTC CCA GCA TTG TGG AAT TTG GAA AGA AAG TAT GGT TCA         780
Arg His Ala Phe Pro Ala Leu Trp Asn Leu Glu Arg Lys Tyr Gly Ser
    225                 230                 235

GTT ATT GTT GGT GCC ATC TTG TCT AAG CTA GCA GCT AAA GGT GAT CCA         828
Val Ile Val Gly Ala Ile Leu Ser Lys Leu Ala Ala Lys Gly Asp Pro
240                 245                 250                 255
```

```
GTA AAG ACA AGA CAT GAT TCA TCA GGG AAA AGA AGG AAT AGA CGA GTG       876
Val Lys Thr Arg His Asp Ser Ser Gly Lys Arg Arg Asn Arg Arg Val
                260                 265                 270

TCG TTT TCA TTT CAT GGT GGA ATG CAG TCA CTA ATA AAT GCA CTT CAC       924
Ser Phe Ser Phe His Gly Gly Met Gln Ser Leu Ile Asn Ala Leu His
            275                 280                 285

AAT GAA GTT GGA GAT GAT AAT GTG AAG CTT GGT ACA GAA GTG TTG TCA       972
Asn Glu Val Gly Asp Asp Asn Val Lys Leu Gly Thr Glu Val Leu Ser
        290                 295                 300

TTG GCA TGT ACA TTT GAT GGA GTT CCT GCA CTA GGC AGG TGG TCA ATT      1020
Leu Ala Cys Thr Phe Asp Gly Val Pro Ala Leu Gly Arg Trp Ser Ile
    305                 310                 315

TCT GTT GAT TCG AAG GAT AGC GGT GAC AAG GAC CTT GCT AGT AAC CAA      1068
Ser Val Asp Ser Lys Asp Ser Gly Asp Lys Asp Leu Ala Ser Asn Gln
320                 325                 330                 335

ACC TTT GAT GCT GTT ATA ATG ACA GCT CCA TTG TCA AAT GTC CGG AGG      1116
Thr Phe Asp Ala Val Ile Met Thr Ala Pro Leu Ser Asn Val Arg Arg
                340                 345                 350

ATG AAG TTC ACC AAA GGT GGA GCT CCG GTT GTT CTT GAC TTT CTT CCT      1164
Met Lys Phe Thr Lys Gly Gly Ala Pro Val Val Leu Asp Phe Leu Pro
            355                 360                 365

AAG ATG GAT TAT CTA CCA CTA TCT CTC ATG GTG ACT GCT TTT AAG AAG      1212
Lys Met Asp Tyr Leu Pro Leu Ser Leu Met Val Thr Ala Phe Lys Lys
        370                 375                 380

GAT GAT GTC AAG AAA CCT CTG GAA GGA TTT GGG GTC TTA ATA CCT TAC      1260
Asp Asp Val Lys Lys Pro Leu Glu Gly Phe Gly Val Leu Ile Pro Tyr
    385                 390                 395

AAG GAA CAG CAA AAA CAT GGT CTG AAA ACC CTT GGG ACT CTC TTT TCC      1308
Lys Glu Gln Gln Lys His Gly Leu Lys Thr Leu Gly Thr Leu Phe Ser
400                 405                 410                 415

TCA ATG ATG TTC CCA GAT CGA GCT CCT GAT GAC CAA TAT TTA TAT ACA      1356
Ser Met Met Phe Pro Asp Arg Ala Pro Asp Asp Gln Tyr Leu Tyr Thr
                420                 425                 430

ACA TTT GTT GGG GGT AGC CAC AAT AGA GAT CTT GCT GGA GCT CCA ACG      1404
Thr Phe Val Gly Gly Ser His Asn Arg Asp Leu Ala Gly Ala Pro Thr
            435                 440                 445

TCT ATT CTG AAA CAA CTT GTG ACC TCT GAC CTT AAA AAA CTC TTG GGC      1452
Ser Ile Leu Lys Gln Leu Val Thr Ser Asp Leu Lys Lys Leu Leu Gly
        450                 455                 460

GTA GAG GGG CAA CCA ACT TTT GTC AAG CAT GTA TAC TGG GGA AAT GCT      1500
Val Glu Gly Gln Pro Thr Phe Val Lys His Val Tyr Trp Gly Asn Ala
    465                 470                 475

TTT CCT TTG TAT GGC CAT GAT TAT AGT TCT GTA TTG GAA GCT ATA GAA      1548
Phe Pro Leu Tyr Gly His Asp Tyr Ser Ser Val Leu Glu Ala Ile Glu
480                 485                 490                 495

AAG ATG GAG AAA AAC CTT CCA GGG TTC TTC TAC GCA GGA AAT AGC AAG      1596
Lys Met Glu Lys Asn Leu Pro Gly Phe Phe Tyr Ala Gly Asn Ser Lys
                500                 505                 510

GAT GGG CTT GCT GTT GGA AGT GTT ATA GCT TCA GGA AGC AAG GCT GCT      1644
Asp Gly Leu Ala Val Gly Ser Val Ile Ala Ser Gly Ser Lys Ala Ala
            515                 520                 525

GAC CTT GCA ATC TCA TAT CTT GAA TCT CAC ACC AAG CAT AAT AAT TCA      1692
Asp Leu Ala Ile Ser Tyr Leu Glu Ser His Thr Lys His Asn Asn Ser
        530                 535                 540

CAT TGAAAGTGTC TGACCTATCC TCTAGCAGTT GTCGACAAAT TTCTCCAGTT           1745
His

545

CATGTACAGT AGAAACCGAT GCGTTGCAGT TTCAGAACAT CTTCACTTCT TCAGATATTA   1805

ACCCTTCGTT GAACATCCAC CAGAAAGGTA GTCACATGTG TAAGTGGGAA AATGAGGTTA   1865
```

-continued

```
AAAACTATTA TGGCGGCCGA ATGTTCCTT  TTTGTTTTCC TCACAAGTGG CCTACGACAC    1925

TTGATGTTGG AAATACATTT AAATTTGTTG AATTGTTTGA GAACACATGC GTGACGTGTA    1985

ATATTTGCCT ATTGTGATTT TAGCAGTAGT CTTGGCCAGA TTATGCTTTA CGCCTTTAAA    2045

AAAAAAAAAA AAAAAA                                                    2061
```

(2) INFORMATION FOR SEQ ID NO:8:

(i) SEQUENCE CHARACTERISTICS:
        (A) LENGTH: 544 amino acids
        (B) TYPE: amino acid
        (D) TOPOLOGY: linear (ii) MOLECULE TYPE: protein (xi) SEQUENCE DESCRIPTION: SEQ ID NO:8:

```
Met Leu Ala Leu Thr Ala Ser Ala Ser Ser Ala Ser Ser His Pro Tyr
 1               5                  10                  15

Arg His Ala Ser Ala His Thr Arg Arg Pro Arg Leu Arg Ala Val Leu
                20                  25                  30

Ala Met Ala Gly Ser Asp Asp Pro Arg Ala Ala Pro Ala Arg Ser Val
            35                  40                  45

Ala Val Val Gly Ala Gly Val Ser Gly Leu Ala Ala Tyr Arg Leu
    50                  55                  60

Arg Gln Ser Gly Val Asn Val Thr Val Phe Glu Ala Ala Asp Arg Ala
65                  70                  75                  80

Gly Gly Lys Ile Arg Thr Asn Ser Glu Gly Gly Phe Val Trp Asp Glu
                85                  90                  95

Gly Ala Asn Thr Met Thr Glu Gly Glu Trp Glu Ala Ser Arg Leu Ile
            100                 105                 110

Asp Asp Leu Gly Leu Gln Asp Lys Gln Gln Tyr Pro Asn Ser Gln His
        115                 120                 125

Lys Arg Tyr Ile Val Lys Asp Gly Ala Pro Ala Leu Ile Pro Ser Asp
130                 135                 140

Pro Ile Ser Leu Met Lys Ser Ser Val Leu Ser Thr Lys Ser Lys Ile
145                 150                 155                 160

Ala Leu Phe Phe Glu Pro Phe Leu Tyr Lys Lys Ala Asn Thr Arg Asn
                165                 170                 175

Ser Gly Lys Val Ser Glu Glu His Leu Ser Glu Ser Val Gly Ser Phe
            180                 185                 190

Cys Glu Arg His Phe Gly Arg Glu Val Val Asp Tyr Phe Val Asp Pro
        195                 200                 205

Phe Val Ala Gly Thr Ser Ala Gly Asp Pro Glu Ser Leu Ser Ile Arg
    210                 215                 220

His Ala Phe Pro Ala Leu Trp Asn Leu Glu Arg Lys Tyr Gly Ser Val
225                 230                 235                 240

Ile Val Gly Ala Ile Leu Ser Lys Leu Ala Ala Lys Gly Asp Pro Val
                245                 250                 255

Lys Thr Arg His Asp Ser Ser Gly Lys Arg Arg Asn Arg Arg Val Ser
            260                 265                 270

Phe Ser Phe His Gly Gly Met Gln Ser Leu Ile Asn Ala Leu His Asn
        275                 280                 285

Glu Val Gly Asp Asp Asn Val Lys Leu Gly Thr Glu Val Leu Ser Leu
    290                 295                 300

Ala Cys Thr Phe Asp Gly Val Pro Ala Leu Gly Arg Trp Ser Ile Ser
305                 310                 315                 320
```

```
Val Asp Ser Lys Asp Ser Gly Asp Lys Asp Leu Ala Ser Asn Gln Thr
            325                 330                 335

Phe Asp Ala Val Ile Met Thr Ala Pro Leu Ser Asn Val Arg Arg Met
            340                 345                 350

Lys Phe Thr Lys Gly Gly Ala Pro Val Val Leu Asp Phe Leu Pro Lys
            355                 360                 365

Met Asp Tyr Leu Pro Leu Ser Leu Met Val Thr Ala Phe Lys Lys Asp
            370                 375                 380

Asp Val Lys Lys Pro Leu Glu Gly Phe Gly Val Leu Ile Pro Tyr Lys
385                 390                 395                 400

Glu Gln Gln Lys His Gly Leu Lys Thr Leu Gly Thr Leu Phe Ser Ser
            405                 410                 415

Met Met Phe Pro Asp Arg Ala Pro Asp Asp Gln Tyr Leu Tyr Thr Thr
            420                 425                 430

Phe Val Gly Gly Ser His Asn Arg Asp Leu Ala Gly Ala Pro Thr Ser
            435                 440                 445

Ile Leu Lys Gln Leu Val Thr Ser Asp Leu Lys Lys Leu Leu Gly Val
450                 455                 460

Glu Gly Gln Pro Thr Phe Val Lys His Val Tyr Trp Gly Asn Ala Phe
465                 470                 475                 480

Pro Leu Tyr Gly His Asp Tyr Ser Ser Val Leu Glu Ala Ile Glu Lys
            485                 490                 495

Met Glu Lys Asn Leu Pro Gly Phe Phe Tyr Ala Gly Asn Ser Lys Asp
            500                 505                 510

Gly Leu Ala Val Gly Ser Val Ile Ala Ser Gly Ser Lys Ala Ala Asp
            515                 520                 525

Leu Ala Ile Ser Tyr Leu Glu Ser His Thr Lys His Asn Asn Ser His
            530                 535                 540

(2) INFORMATION FOR SEQ ID NO:9:

(i) SEQUENCE CHARACTERISTICS:
        (A) LENGTH: 1811 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (vi) ORIGINAL SOURCE:
        (A) ORGANISM: Triticum aestivum (wheat)

(vii) IMMEDIATE SOURCE:
        (B) CLONE: pWDC-13 (NRRL B-21545)

(ix) FEATURE:
        (A) NAME/KEY: CDS
        (B) LOCATION: 3..1589
        (D) OTHER INFORMATION: /product= "wheat protox-1"

(xi) SEQUENCE DESCRIPTION: SEQ ID NO:9:

GC GCA ACA ATG GCC ACC GCC ACC GTC GCG GCC GCG TCG CCG CTC CGC        47
   Ala Thr Met Ala Thr Ala Thr Val Ala Ala Ala Ser Pro Leu Arg
    1               5                  10                  15

GGC AGG GTC ACC GGG CGC CCA CAC CGC GTC CGC CCG CGT TGC GCT ACC       95
Gly Arg Val Thr Gly Arg Pro His Arg Val Arg Pro Arg Cys Ala Thr
                20                  25                  30

GCG AGC AGC GCG ACC GAG ACT CCG GCG GCG CCC GGC GTG CGG CTG TCC      143
Ala Ser Ser Ala Thr Glu Thr Pro Ala Ala Pro Gly Val Arg Leu Ser
            35                  40                  45
```

-continued

| | |
|---|---|
| GCG GAA TGC GTC ATT GTG GGC GCC GGC ATC AGC GGC CTC TGC ACC GCG<br>Ala Glu Cys Val Ile Val Gly Ala Gly Ile Ser Gly Leu Cys Thr Ala<br>50                              55                         60 | 191 |
| CAG GCG CTG GCC ACC CGA TAC GGC GTC AGC GAC CTG CTC GTC ACG GAG<br>Gln Ala Leu Ala Thr Arg Tyr Gly Val Ser Asp Leu Leu Val Thr Glu<br>65                              70                         75 | 239 |
| GCC CGC GAC CGC CCG GGC GGC AAC ATC ACC ACC GTC GAG CGT CCC GAC<br>Ala Arg Asp Arg Pro Gly Gly Asn Ile Thr Thr Val Glu Arg Pro Asp<br>80                              85                      90                         95 | 287 |
| GAG GGG TAC CTG TGG GAG GAG GGA CCC AAC AGC TTC CAG CCC TCC GAC<br>Glu Gly Tyr Leu Trp Glu Glu Gly Pro Asn Ser Phe Gln Pro Ser Asp<br>                      100                     105                   110 | 335 |
| CCG GTC CTC ACC ATG GCC GTG GAC AGC GGG CTC AAG GAT GAC TTG GTG<br>Pro Val Leu Thr Met Ala Val Asp Ser Gly Leu Lys Asp Asp Leu Val<br>              115                     120                     125 | 383 |
| TTC GGG GAC CCC AAC GCG CCC CGG TTC GTG CTG TGG GAG GGG AAG CTG<br>Phe Gly Asp Pro Asn Ala Pro Arg Phe Val Leu Trp Glu Gly Lys Leu<br>130                            135                     140 | 431 |
| AGG CCG GTG CCG TCG AAG CCA GGC GAC CTG CCT TTC TTC AGC CTC ATG<br>Arg Pro Val Pro Ser Lys Pro Gly Asp Leu Pro Phe Phe Ser Leu Met<br>145                            150                     155 | 479 |
| AGT ATC CCT GGG AAG CTC AGG GCC GGC CTT GGC GCG CTC GGC ATT CGC<br>Ser Ile Pro Gly Lys Leu Arg Ala Gly Leu Gly Ala Leu Gly Ile Arg<br>160                            165                     170                     175 | 527 |
| CCA CCT CCT CCA GGG CGC GAG GAG TCG GTG GAG GAG TTT GTG CGC CGC<br>Pro Pro Pro Pro Gly Arg Glu Glu Ser Val Glu Glu Phe Val Arg Arg<br>                      180                     185                   190 | 575 |
| AAC CTC GGT GCC GAG GTC TTT GAG CGC CTC ATC GAG CCT TTC TGC TCA<br>Asn Leu Gly Ala Glu Val Phe Glu Arg Leu Ile Glu Pro Phe Cys Ser<br>                      195                     200                   205 | 623 |
| GGT GTA TAT GCT GGT GAT CCT TCG AAG CTT AGT ATG AAG GCT GCA TTT<br>Gly Val Tyr Ala Gly Asp Pro Ser Lys Leu Ser Met Lys Ala Ala Phe<br>                      210                     215                   220 | 671 |
| GGG AAG GTC TGG AGG TTG GAG GAG ATT GGA GGT AGT ATT ATT GGT GGA<br>Gly Lys Val Trp Arg Leu Glu Glu Ile Gly Gly Ser Ile Ile Gly Gly<br>225                            230                     235 | 719 |
| ACC ATC AAG GCG ATT CAG GAT AAA GGG AAG AAC CCC AAA CCG CCA AGG<br>Thr Ile Lys Ala Ile Gln Asp Lys Gly Lys Asn Pro Lys Pro Pro Arg<br>240                            245                     250                     255 | 767 |
| GAT CCC CGA CTT CCG GCA CCA AAG GGA CAG ACG GTG GCA TCT TTC AGG<br>Asp Pro Arg Leu Pro Ala Pro Lys Gly Gln Thr Val Ala Ser Phe Arg<br>                      260                     265                   270 | 815 |
| AAG GGT CTA GCC ATG CTC CCG AAT GCC ATC GCA TCT AGG CTG GGT AGT<br>Lys Gly Leu Ala Met Leu Pro Asn Ala Ile Ala Ser Arg Leu Gly Ser<br>                      275                     280                   285 | 863 |
| AAA GTC AAG CTG TCA TGG AAG CTT ACG AGC ATT ACA AAG GCG GAC AAC<br>Lys Val Lys Leu Ser Trp Lys Leu Thr Ser Ile Thr Lys Ala Asp Asn<br>290                            295                     300 | 911 |
| CAA GGA TAT GTA TTA GGT TAT GAA ACA CCA GAA GGA CTT GTT TCA GTG<br>Gln Gly Tyr Val Leu Gly Tyr Glu Thr Pro Glu Gly Leu Val Ser Val<br>305                            310                     315 | 959 |
| CAG GCT AAA AGT GTT ATC ATG ACC ATC CCG TCA TAT GTT GCT AGT GAT<br>Gln Ala Lys Ser Val Ile Met Thr Ile Pro Ser Tyr Val Ala Ser Asp<br>320                            325                     330                   335 | 1007 |
| ATC TTG CGC CCA CTT TCA ATT GAT GCA GCA GAT GCA CTC TCA AAA TTC<br>Ile Leu Arg Pro Leu Ser Ile Asp Ala Ala Asp Ala Leu Ser Lys Phe<br>                      340                     345                   350 | 1055 |
| TAT TAT CCG CCA GTT GCT GCT GTA ACT GTT TCA TAT CCA AAA GAA GCT<br>Tyr Tyr Pro Pro Val Ala Ala Val Thr Val Ser Tyr Pro Lys Glu Ala<br>                      355                     360                   365 | 1103 |

```
ATT AGA AAA GAA TGC TTA ATT GAT GGG GAG CTC CAG GGT TTC GGC CAG      1151
Ile Arg Lys Glu Cys Leu Ile Asp Gly Glu Leu Gln Gly Phe Gly Gln
        370                 375                 380

TTG CAT CCA CGT AGC CAA GGA GTC GAG ACT TTA GGG ACA ATA TAT AGC      1199
Leu His Pro Arg Ser Gln Gly Val Glu Thr Leu Gly Thr Ile Tyr Ser
385                 390                 395

TCT TCT CTC TTT CCT AAT CGT GCT CCT GCT GGA AGA GTG TTA CTT CTG      1247
Ser Ser Leu Phe Pro Asn Arg Ala Pro Ala Gly Arg Val Leu Leu Leu
400                 405                 410                 415

AAC TAT ATC GGG GGT TCT ACA AAT ACA GGG ATC GTC TCC AAG ACT GAG      1295
Asn Tyr Ile Gly Gly Ser Thr Asn Thr Gly Ile Val Ser Lys Thr Glu
                420                 425                 430

AGT GAC TTA GTA GGA GCC GTT GAC CGT GAC CTC AGA AAA ATG TTG ATA      1343
Ser Asp Leu Val Gly Ala Val Asp Arg Asp Leu Arg Lys Met Leu Ile
            435                 440                 445

AAC CCT AGA GCA GCA GAC CCT TTA GCA TTA GGG GTT CGA GTG TGG CCA      1391
Asn Pro Arg Ala Ala Asp Pro Leu Ala Leu Gly Val Arg Val Trp Pro
        450                 455                 460

CAA GCA ATA CCA CAG TTT TTG ATT GGG CAC CTT GAT CGC CTT GCT GCT      1439
Gln Ala Ile Pro Gln Phe Leu Ile Gly His Leu Asp Arg Leu Ala Ala
    465                 470                 475

GCA AAA TCT GCA CTG GGC CAA GGC GGC TAC GAC GGG TTG TTC CTA GGA      1487
Ala Lys Ser Ala Leu Gly Gln Gly Gly Tyr Asp Gly Leu Phe Leu Gly
480                 485                 490                 495

GGA AAC TAC GTC GCA GGA GTT GCC TTG GGC CGA TGC ATC GAG GGT GCG      1535
Gly Asn Tyr Val Ala Gly Val Ala Leu Gly Arg Cys Ile Glu Gly Ala
                500                 505                 510

TAC GAG AGT GCC TCA CAA GTA TCT GAC TTC TTG ACC AAG TAT GCC TAC      1583
Tyr Glu Ser Ala Ser Gln Val Ser Asp Phe Leu Thr Lys Tyr Ala Tyr
            515                 520                 525

AAG TGA TGGAAGTAGT GCATCTCTTC ATTTTGTTGC ATATACGAGG TGAGGCTAGG       1639
Lys

ATCGGTAAAA CATCATGAGA TTCTGTAGTG TTTCTTTAAT TGAAAAAACA AATTTTAGTG    1699

ATGCAATATG TGCTCTTTCC TGTAGTTCGA GCATGTACAT CGGTATGGGA TAAAGTAGAA    1759

TAAGCTATTC TGCAAAAGCA GTGATTTTTT TTGAAAAAAA AAAAAAAAA AA            1811

(2) INFORMATION FOR SEQ ID NO:10:

(i) SEQUENCE CHARACTERISTICS:
        (A) LENGTH: 528 amino acids
        (B) TYPE: amino acid
        (D) TOPOLOGY: linear (ii) MOLECULE TYPE: protein (xi) SEQUENCE DESCRIPTION: SEQ ID NO:10:

Ala Thr Met Ala Thr Ala Thr Val Ala Ala Ala Ser Pro Leu Arg Gly
 1               5                  10                  15

Arg Val Thr Gly Arg Pro His Arg Val Arg Pro Arg Cys Ala Thr Ala
            20                  25                  30

Ser Ser Ala Thr Glu Thr Pro Ala Ala Pro Gly Val Arg Leu Ser Ala
        35                  40                  45

Glu Cys Val Ile Val Gly Ala Gly Ile Ser Gly Leu Cys Thr Ala Gln
    50                  55                  60

Ala Leu Ala Thr Arg Tyr Gly Val Ser Asp Leu Leu Val Thr Glu Ala
65                  70                  75                  80

Arg Asp Arg Pro Gly Gly Asn Ile Thr Thr Val Glu Arg Pro Asp Glu
                85                  90                  95
```

-continued

```
Gly Tyr Leu Trp Glu Glu Gly Pro Asn Ser Phe Gln Pro Ser Asp Pro
            100                 105                 110

Val Leu Thr Met Ala Val Asp Ser Gly Leu Lys Asp Asp Leu Val Phe
            115                 120                 125

Gly Asp Pro Asn Ala Pro Arg Phe Val Leu Trp Glu Gly Lys Leu Arg
            130                 135                 140

Pro Val Pro Ser Lys Pro Gly Asp Leu Pro Phe Phe Ser Leu Met Ser
145                 150                 155                 160

Ile Pro Gly Lys Leu Arg Ala Gly Leu Gly Ala Leu Gly Ile Arg Pro
            165                 170                 175

Pro Pro Pro Gly Arg Glu Ser Val Glu Glu Phe Val Arg Arg Asn
            180                 185                 190

Leu Gly Ala Glu Val Phe Glu Arg Leu Ile Glu Pro Phe Cys Ser Gly
            195                 200                 205

Val Tyr Ala Gly Asp Pro Ser Lys Leu Ser Met Lys Ala Ala Phe Gly
            210                 215                 220

Lys Val Trp Arg Leu Glu Glu Ile Gly Gly Ser Ile Ile Gly Gly Thr
225                 230                 235                 240

Ile Lys Ala Ile Gln Asp Lys Gly Lys Asn Pro Lys Pro Pro Arg Asp
            245                 250                 255

Pro Arg Leu Pro Ala Pro Lys Gly Gln Thr Val Ala Ser Phe Arg Lys
            260                 265                 270

Gly Leu Ala Met Leu Pro Asn Ala Ile Ala Ser Arg Leu Gly Ser Lys
            275                 280                 285

Val Lys Leu Ser Trp Lys Leu Thr Ser Ile Thr Lys Ala Asp Asn Gln
            290                 295                 300

Gly Tyr Val Leu Gly Tyr Glu Thr Pro Glu Gly Leu Val Ser Val Gln
305                 310                 315                 320

Ala Lys Ser Val Ile Met Thr Ile Pro Ser Tyr Val Ala Ser Asp Ile
            325                 330                 335

Leu Arg Pro Leu Ser Ile Asp Ala Ala Asp Ala Leu Ser Lys Phe Tyr
            340                 345                 350

Tyr Pro Pro Val Ala Ala Val Thr Val Ser Tyr Pro Lys Glu Ala Ile
            355                 360                 365

Arg Lys Glu Cys Leu Ile Asp Gly Glu Leu Gln Gly Phe Gly Gln Leu
            370                 375                 380

His Pro Arg Ser Gln Gly Val Glu Thr Leu Gly Thr Ile Tyr Ser Ser
385                 390                 395                 400

Ser Leu Phe Pro Asn Arg Ala Pro Ala Gly Arg Val Leu Leu Leu Asn
            405                 410                 415

Tyr Ile Gly Gly Ser Thr Asn Thr Gly Ile Val Ser Lys Thr Glu Ser
            420                 425                 430

Asp Leu Val Gly Ala Val Asp Arg Asp Leu Arg Lys Met Leu Ile Asn
            435                 440                 445

Pro Arg Ala Ala Asp Pro Leu Ala Leu Gly Val Arg Val Trp Pro Gln
450                 455                 460

Ala Ile Pro Gln Phe Leu Ile Gly His Leu Asp Arg Leu Ala Ala Ala
465                 470                 475                 480

Lys Ser Ala Leu Gly Gln Gly Gly Tyr Asp Gly Leu Phe Leu Gly Gly
            485                 490                 495

Asn Tyr Val Ala Gly Val Ala Leu Gly Arg Cys Ile Glu Gly Ala Tyr
            500                 505                 510

Glu Ser Ala Ser Gln Val Ser Asp Phe Leu Thr Lys Tyr Ala Tyr Lys
            515                 520                 525
```

(2) INFORMATION FOR SEQ ID NO:11:

(i) SEQUENCE CHARACTERISTICS:
  (A) LENGTH: 1847 base pairs
  (B) TYPE: nucleic acid
  (C) STRANDEDNESS: single
  (D) TOPOLOGY: linear (ii) MOLECULE TYPE: cDNA (iii) HYPOTHETICAL: NO (vi) ORIGINAL SOURCE:
  (A) ORGANISM: soybean (vii) IMMEDIATE SOURCE:
  (B) CLONE: pWDC-12 (NRRL B-21516)

(ix) FEATURE:
  (A) NAME/KEY: CDS
  (B) LOCATION: 55..1683
  (D) OTHER INFORMATION: /product= "soybean protox-1"

(xi) SEQUENCE DESCRIPTION: SEQ ID NO:11:

```
CTTTAGCACA GTGTTGAAGA TAACGAACGA ATAGTGCCAT TACTGTAACC AACC ATG         57
                                                            Met
                                                              1

GTT TCC GTC TTC AAC GAG ATC CTA TTC CCG CCG AAC CAA ACC CTT CTT         105
Val Ser Val Phe Asn Glu Ile Leu Phe Pro Pro Asn Gln Thr Leu Leu
              5                  10                  15

CGC CCC TCC CTC CAT TCC CCA ACC TCT TTC TTC ACC TCT CCC ACT CGA         153
Arg Pro Ser Leu His Ser Pro Thr Ser Phe Phe Thr Ser Pro Thr Arg
         20                  25                  30

AAA TTC CCT CGC TCT CGC CCT AAC CCT ATT CTA CGC TGC TCC ATT GCG         201
Lys Phe Pro Arg Ser Arg Pro Asn Pro Ile Leu Arg Cys Ser Ile Ala
 35                  40                  45

GAG GAA TCC ACC GCG TCT CCG CCC AAA ACC AGA GAC TCC GCC CCC GTG         249
Glu Glu Ser Thr Ala Ser Pro Pro Lys Thr Arg Asp Ser Ala Pro Val
 50                  55                  60                  65

GAC TGC GTC GTC GTC GGC GGA GGC GTC AGC GGC CTC TGC ATC GCC CAG         297
Asp Cys Val Val Val Gly Gly Gly Val Ser Gly Leu Cys Ile Ala Gln
                 70                  75                  80

GCC CTC GCC ACC AAA CAC GCC AAT GCC AAC GTC GTC GTC ACG GAG GCC         345
Ala Leu Ala Thr Lys His Ala Asn Ala Asn Val Val Val Thr Glu Ala
                 85                  90                  95

CGA GAC CGC GTC GGC GGC AAC ATC ACC ACG ATG GAG AGG GAC GGA TAC         393
Arg Asp Arg Val Gly Gly Asn Ile Thr Thr Met Glu Arg Asp Gly Tyr
            100                 105                 110

CTC TGG GAA GAA GGC CCC AAC AGC TTC CAG CCT TCT GAT CCA ATG CTC         441
Leu Trp Glu Glu Gly Pro Asn Ser Phe Gln Pro Ser Asp Pro Met Leu
        115                 120                 125

ACC ATG GTG GTG GAC AGT GGT TTA AAG GAT GAG CTT GTT TTG GGG GAT         489
Thr Met Val Val Asp Ser Gly Leu Lys Asp Glu Leu Val Leu Gly Asp
130                 135                 140                 145

CCT GAT GCA CCT CGG TTT GTG TTG TGG AAC AGG AAG TTG AGG CCG GTG         537
Pro Asp Ala Pro Arg Phe Val Leu Trp Asn Arg Lys Leu Arg Pro Val
                150                 155                 160

CCC GGG AAG CTG ACT GAT TTG CCT TTC TTT GAC TTG ATG AGC ATT GGT         585
Pro Gly Lys Leu Thr Asp Leu Pro Phe Phe Asp Leu Met Ser Ile Gly
                165                 170                 175

GGC AAA ATC AGG GCT GGC TTT GGT GCG CTT GGA ATT CGG CCT CCT CCT         633
Gly Lys Ile Arg Ala Gly Phe Gly Ala Leu Gly Ile Arg Pro Pro Pro
            180                 185                 190
```

```
CCA GGT CAT GAG GAA TCG GTT GAA GAG TTT GTT CGT CGG AAC CTT GGT        681
Pro Gly His Glu Glu Ser Val Glu Glu Phe Val Arg Arg Asn Leu Gly
        195                 200                 205

GAT GAG GTT TTT GAA CGG TTG ATA GAG CCT TTT TGT TCA GGG GTC TAT        729
Asp Glu Val Phe Glu Arg Leu Ile Glu Pro Phe Cys Ser Gly Val Tyr
210                 215                 220                 225

GCA GGC GAT CCT TCA AAA TTA AGT ATG AAA GCA GCA TTC GGG AAA GTT        777
Ala Gly Asp Pro Ser Lys Leu Ser Met Lys Ala Ala Phe Gly Lys Val
                230                 235                 240

TGG AAG CTG GAA AAA AAT GGT GGT AGC ATT ATT GGT GGA ACT TTC AAA        825
Trp Lys Leu Glu Lys Asn Gly Gly Ser Ile Ile Gly Gly Thr Phe Lys
        245                 250                 255

GCA ATA CAA GAG AGA AAT GGA GCT TCA AAA CCA CCT CGA GAT CCG CGT        873
Ala Ile Gln Glu Arg Asn Gly Ala Ser Lys Pro Pro Arg Asp Pro Arg
260                 265                 270

CTG CCA AAA CCA AAA GGT CAG ACT GTT GGA TCT TTC CGG AAG GGA CTT        921
Leu Pro Lys Pro Lys Gly Gln Thr Val Gly Ser Phe Arg Lys Gly Leu
        275                 280                 285

ACC ATG TTG CCT GAT GCA ATT TCT GCC AGA CTA GGC AAC AAA GTA AAG        969
Thr Met Leu Pro Asp Ala Ile Ser Ala Arg Leu Gly Asn Lys Val Lys
290                 295                 300                 305

TTA TCT TGG AAG CTT TCA AGT ATT AGT AAA CTG GAT AGT GGA GAG TAC       1017
Leu Ser Trp Lys Leu Ser Ser Ile Ser Lys Leu Asp Ser Gly Glu Tyr
        310                 315                 320

AGT TTG ACA TAT GAA ACA CCA GAA GGA GTG GTT TCT TTG CAG TGC AAA       1065
Ser Leu Thr Tyr Glu Thr Pro Glu Gly Val Val Ser Leu Gln Cys Lys
            325                 330                 335

ACT GTT GTC CTG ACC ATT CCT TCC TAT GTT GCT AGT ACA TTG CTG CGT       1113
Thr Val Val Leu Thr Ile Pro Ser Tyr Val Ala Ser Thr Leu Leu Arg
            340                 345                 350

CCT CTG TCT GCT GCT GCT GCA GAT GCA CTT TCA AAG TTT TAT TAC CCT       1161
Pro Leu Ser Ala Ala Ala Ala Asp Ala Leu Ser Lys Phe Tyr Tyr Pro
        355                 360                 365

CCA GTT GCT GCA GTT TCC ATA TCC TAT CCA AAA GAA GCT ATT AGA TCA       1209
Pro Val Ala Ala Val Ser Ile Ser Tyr Pro Lys Glu Ala Ile Arg Ser
370                 375                 380                 385

GAA TGC TTG ATA GAT GGT GAG TTG AAG GGG TTT GGT CAA TTG CAT CCA       1257
Glu Cys Leu Ile Asp Gly Glu Leu Lys Gly Phe Gly Gln Leu His Pro
            390                 395                 400

CGT AGC CAA GGA GTG GAA ACA TTA GGA ACT ATA TAC AGC TCA TCA CTA       1305
Arg Ser Gln Gly Val Glu Thr Leu Gly Thr Ile Tyr Ser Ser Ser Leu
        405                 410                 415

TTC CCC AAC CGA GCA CCA CCT GGA AGG GTT CTA CTC TTG AAT TAC ATT       1353
Phe Pro Asn Arg Ala Pro Pro Gly Arg Val Leu Leu Leu Asn Tyr Ile
            420                 425                 430

GGA GGA GCA ACT AAT ACT GGA ATT TTA TCG AAG ACG GAC AGT GAA CTT       1401
Gly Gly Ala Thr Asn Thr Gly Ile Leu Ser Lys Thr Asp Ser Glu Leu
        435                 440                 445

GTG GAA ACA GTT GAT CGA GAT TTG AGG AAA ATC CTT ATA AAC CCA AAT       1449
Val Glu Thr Val Asp Arg Asp Leu Arg Lys Ile Leu Ile Asn Pro Asn
450                 455                 460                 465

GCC CAG GAT CCA TTT GTA GTG GGG GTG AGA CTG TGG CCT CAA GCT ATT       1497
Ala Gln Asp Pro Phe Val Val Gly Val Arg Leu Trp Pro Gln Ala Ile
                470                 475                 480

CCA CAG TTC TTA GTT GGC CAT CTT GAT CTT CTA GAT GTT GCT AAA GCT       1545
Pro Gln Phe Leu Val Gly His Leu Asp Leu Leu Asp Val Ala Lys Ala
        485                 490                 495

TCT ATC AGA AAT ACT GGG TTT GAA GGG CTC TTC CTT GGG GGT AAT TAT       1593
Ser Ile Arg Asn Thr Gly Phe Glu Gly Leu Phe Leu Gly Gly Asn Tyr
            500                 505                 510
```

```
GTG TCT GGT GTT GCC TTG GGA CGA TGC GTT GAG GGA GCC TAT GAG GTA    1641
Val Ser Gly Val Ala Leu Gly Arg Cys Val Glu Gly Ala Tyr Glu Val
515                 520                 525

GCA GCT GAA GTA AAC GAT TTT CTC ACA AAT AGA GTG TAC AAA            1683
Ala Ala Glu Val Asn Asp Phe Leu Thr Asn Arg Val Tyr Lys
530                 535                 540

TAGTAGCAGT TTTTGTTTTT GTGGTGGAAT GGGTGATGGG ACTCTCGTGT TCCATTGAAT  1743

TATAATAATG TGAAAGTTTC TCAAATTCGT TCGATAGGTT TTTGGCGGCT TCTATTGCTG  1803

ATAATGTAAA ATCCTCTTTA AGTTTGAAAA AAAAAAAAAA AAAA                   1847
```

(2) INFORMATION FOR SEQ ID NO:12:

(i) SEQUENCE CHARACTERISTICS:
        (A) LENGTH: 543 amino acids
        (B) TYPE: amino acid
        (D) TOPOLOGY: linear (ii) MOLECULE TYPE: protein (xi) SEQUENCE DESCRIPTION: SEQ ID 12:

```
Met Val Ser Val Phe Asn Glu Ile Leu Phe Pro Pro Asn Gln Thr Leu
1               5                   10                  15

Leu Arg Pro Ser Leu His Ser Pro Thr Ser Phe Phe Thr Ser Pro Thr
                20                  25                  30

Arg Lys Phe Pro Arg Ser Arg Pro Asn Pro Ile Leu Arg Cys Ser Ile
            35                  40                  45

Ala Glu Glu Ser Thr Ala Ser Pro Pro Lys Thr Arg Asp Ser Ala Pro
50                  55                  60

Val Asp Cys Val Val Gly Gly Val Ser Gly Leu Cys Ile Ala
65                  70                  75                  80

Gln Ala Leu Ala Thr Lys His Ala Asn Ala Asn Val Val Thr Glu
                85                  90                  95

Ala Arg Asp Arg Val Gly Gly Asn Ile Thr Thr Met Glu Arg Asp Gly
                100                 105                 110

Tyr Leu Trp Glu Glu Gly Pro Asn Ser Phe Gln Pro Ser Asp Pro Met
            115                 120                 125

Leu Thr Met Val Val Asp Ser Gly Leu Lys Asp Glu Leu Val Leu Gly
130                 135                 140

Asp Pro Asp Ala Pro Arg Phe Val Leu Trp Asn Arg Lys Leu Arg Pro
145                 150                 155                 160

Val Pro Gly Lys Leu Thr Asp Leu Pro Phe Phe Asp Leu Met Ser Ile
                165                 170                 175

Gly Gly Lys Ile Arg Ala Gly Phe Gly Ala Leu Gly Ile Arg Pro Pro
            180                 185                 190

Pro Pro Gly His Glu Glu Ser Val Glu Glu Phe Val Arg Arg Asn Leu
        195                 200                 205

Gly Asp Glu Val Phe Glu Arg Leu Ile Glu Pro Phe Cys Ser Gly Val
210                 215                 220

Tyr Ala Gly Asp Pro Ser Lys Leu Ser Met Lys Ala Ala Phe Gly Lys
225                 230                 235                 240

Val Trp Lys Leu Glu Lys Asn Gly Gly Ser Ile Ile Gly Gly Thr Phe
                245                 250                 255

Lys Ala Ile Gln Glu Arg Asn Gly Ala Ser Lys Pro Pro Arg Asp Pro
            260                 265                 270

Arg Leu Pro Lys Pro Lys Gly Gln Thr Val Gly Ser Phe Arg Lys Gly
        275                 280                 285
```

```
Leu Thr Met Leu Pro Asp Ala Ile Ser Ala Arg Leu Gly Asn Lys Val
    290                 295                 300
Lys Leu Ser Trp Lys Leu Ser Ser Ile Ser Lys Leu Asp Ser Gly Glu
305                 310                 315                 320
Tyr Ser Leu Thr Tyr Glu Thr Pro Glu Gly Val Val Ser Leu Gln Cys
                325                 330                 335
Lys Thr Val Val Leu Thr Ile Pro Ser Tyr Val Ala Ser Thr Leu Leu
            340                 345                 350
Arg Pro Leu Ser Ala Ala Ala Asp Ala Leu Ser Lys Phe Tyr Tyr
        355                 360                 365
Pro Pro Val Ala Ala Val Ser Ile Ser Tyr Pro Lys Glu Ala Ile Arg
    370                 375                 380
Ser Glu Cys Leu Ile Asp Gly Glu Leu Lys Gly Phe Gly Gln Leu His
385                 390                 395                 400
Pro Arg Ser Gln Gly Val Glu Thr Leu Gly Thr Ile Tyr Ser Ser Ser
                405                 410                 415
Leu Phe Pro Asn Arg Ala Pro Pro Gly Arg Val Leu Leu Leu Asn Tyr
            420                 425                 430
Ile Gly Gly Ala Thr Asn Thr Gly Ile Leu Ser Lys Thr Asp Ser Glu
        435                 440                 445
Leu Val Glu Thr Val Asp Arg Asp Leu Arg Lys Ile Leu Ile Asn Pro
    450                 455                 460
Asn Ala Gln Asp Pro Phe Val Val Gly Val Arg Leu Trp Pro Gln Ala
465                 470                 475                 480
Ile Pro Gln Phe Leu Val Gly His Leu Asp Leu Leu Asp Val Ala Lys
                485                 490                 495
Ala Ser Ile Arg Asn Thr Gly Phe Glu Gly Leu Phe Leu Gly Gly Asn
            500                 505                 510
Tyr Val Ser Gly Val Ala Leu Gly Arg Cys Val Glu Gly Ala Tyr Glu
        515                 520                 525
Val Ala Ala Glu Val Asn Asp Phe Leu Thr Asn Arg Val Tyr Lys
    530                 535                 540

(2) INFORMATION FOR SEQ ID NO:13:

(i) SEQUENCE CHARACTERISTICS:
        (A) LENGTH: 583 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: promoter
        (B) LOCATION: 1..583
        (D) OTHER INFORMATION: /function= "arabidopsis protox-1
            promoter"

(xi) SEQUENCE DESCRIPTION: SEQ ID NO:13:

GAATTCCGAT CGAATTATAT AATTATCATA AATTTGAATA AGCATGTTGC CTTTTATTAA      60

AGAGGTTTAA TAAAGTTTGG TAATAATGGA CTTTGACTTC AAACTCGATT CTCATGTAAT    120

TAATTAATAT TTCATCAAA ATTTGGTCAC TAATATTACC AAATTAATAT ACTAAAATGT     180

TAATTCGCAA ATAAAACACT AATTCCAAAT AAAGGGTCAT TATGATAAAC ACGTATTGAA    240

CTTGATAAAG CAAAGCAAAA ATAATGGGTT TCAAGGTTTG GGTTATATAT GACAAAAAAA    300

AAAAAGGTT TGGTTATATA TCTATTGGGC CTATAACCAT GTTATACAAA TTTGGGCCTA     360
```

```
ACTAAAATAA TAAAATAAAC GTAATGGTCC TTTTTATATT TGGGTCAAAC CCAACTCTAA      420

ACCCAAACCA AAGAAAAAGT ATACGGTACG GTACACAGAC TTATGGTGTG TGTGATTGCA      480

GGTGAATATT TCTCGTCGTC TTCTCCTTTC TTCTGAAGAA GATTACCCAA TCTGAAAAAA     540

ACCAAGAAGC TGACAAAATT CCGAATTCTC TGCGATTTCC ATG                        583
```

(2) INFORMATION FOR SEQ ID NO:14:

(i) SEQUENCE CHARACTERISTICS:
        (A) LENGTH: 3848 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (ix) FEATURE:
        (A) NAME/KEY: promoter
        (B) LOCATION: 1..3848
        (D) OTHER INFORMATION: /function= "maize protox-1 promoter"

(xi) SEQUENCE DESCRIPTION: SEQ ID NO:14:

```
TCGATCTTTC TAGGCTGATC CCCAAATCTT CCTCCGAAGC CCCTGGCGCC TCTGCCCCTT       60

GGAGCTGGTG GCCTGAAAGA GCTTTGCTGT TGCCCCGAAG ATTGTGAGGT ATATTGTGAC      120

CTCTGAGACT GACTTCCTTT GTCGTCACTT TGAGTGGAGT TATGGATTGA CCTGACGTGC      180

CTCAGATGGA TTCTTCCTCC GAAGCCCCTG GTCATTTCGG AGAATCTGTA ATCTTATTCC      240

CTTCTTTGGC GAAAATCTGT CAGCTTGGAT GTACTCATCC ATCTTCTGAA GCAGCTTCTC      300

CAGAGTTTGT GGAGGCTTCC TGGCGAAATA TTGGGCTGTA GGTCCTGGAC GAAGACCCTT      360

GATCATGGCC TCAATGACAA TCTCATTGGG CACCGTAGGC GCTTGTGCCC TCAATCGCAA      420

GAACCTTCGT ACATATGCCT GAAGGTATTC TTCGTGATCT TGTGTGCATT GGAACAGAGC      480

CTGAGCTGTG ACCGACTTCG TTTGAAAGCC TTGGAAGCTA GTAACCAACA TGTGCTTAAG      540

CTTCTGCCAC GACGTGATAG TCCCTGGCCG AAGAGAAGAA TACCATGTTT GGGCTACATT      600

CCGGACTGCC ATGACGAAGG ACTTCGCCAT GACTACAGTG TTGACCCCAT ACGAAGATAT      660

AGTTGCTTCG TAGCTCATCA GAAACTGCTT TGGATCTGAG TGCCCATCAT ACATGGGGAG      720

CTGAGGTGGC TTGTATGATG GGGGCCATGG GGTAGCCTGC AGTTCTGCTG CCAAGGGAGA      780

AGCATCATCA AAAGTAAAGG CATCATGATT AAAATCATCA TACCATCCAT CCTCGTTGAA      840

TAAGCCTTCT TGACGAAGCT CCCTGTGTTG GGGCCTTCGA TCTTGTTCAT CTTGAACAAG      900

ATGACGCACT TCTTCAGTGG CTTCGTCGAT CTTTCTTTGG AGATCAGCCA GTCGCACCAT      960

CTTCTCCTTC TTTCTTTGTA CTTGTTGATG GATGATCTCC ATGTCCCTGA TCTCTTGGTC     1020

CAACTCCTCC TCTTGGAGTG TCAGACTGGT GGCTTTCCTC TTCTGGCTTC GAGCCTCTCG     1080

AAGAGAAAGA GTTTCTTGAT TTGGGTCCAG CGGCTGCAGT GCAGTGGTCC CTGGTGCTGA     1140

AGCTTTCTTC GGTGGCATGA CAAAGGTCAG TGCTTGCCGA AGGTGGTCGA AAAGGGTTCA     1200

CTAGAGGTGG GAGCCAATGT TGGGGACTTC TCAAGTGCTA TGAGTTAAGA ACAAGGCAAC     1260

ACAAAATGTT AAATATTAAT AGCTTTCATC TTTCGAAGCA TTATTTCCCT TTGGGTATAA     1320

TGATCTTCAG ACGAAAGAGT CCTTCATCAT TGCGATATAT GTTAATAGAA GGAGGAGCAT     1380

ATGAAATGTA AGAGACAACA TGAACAATCG TGTAGCATTG TTAATTCATC ATCATTTTAT     1440

TATTATGGAA AAATAGAAAC AATATTGAAT TACAAATGTA CCTTTGGCTT GACAGAAGAT     1500

AAAAGTACAA GCTTGACGCA CGAGCAAGTA CAAGTCAGTG TGAACAGTAC GGGGGTACTG     1560
```

```
TTCATCTATT TATAGGCACA GGACACAGCC TGTGAGAAAT TACAGTCATG CCCTTTACAT    1620

TTACTATTGA CTTATAGAAA AATCTATGAG GACTGGATAG CCTTTTCCCC TTTAAGTCGG    1680

TGCCTTTTTC CGCGATTAAG CCGAATCTCC CTTGCGCATA GCTTCGGAGC ATCGGCAACC    1740

TTCGTCACGA TCATGCCCTT CTCATTGTGT ATGCTTTTAA TCCTGAATTC GAAGGTACCT    1800

GTCCATAAAC CATACTTGGA AGACATTGTT AAATTATGTT TTTGAGGACC TTCGGAGGAC    1860

GAAGGCCCCC AACAGTCGTG TTTTTGAGGA CCTTCGGAAG ATGAAGGCCC CCAACAAGAC    1920

CTATCCATAA AACCAACCTA TCCACAAAAC CGACCCCATT CACCCTTCAT TTGCCTCACC    1980

AACAACCCTA ATTAGGTTGT TGGTTTAAAT TTTTTAGGGT CAATTTGGTC ATCACCATCC    2040

ACTGTCACTC CACAAACTCA ATATCAATAA ACAGACTCAA TCACCCAAAC TGACCATACC    2100

CATAAAACCG CCCCACCCTT CTAGCGCCTC GCCAGAAACC AGAAACCCTG ATTCAGAGTT    2160

CAAACTTAAA ACGACCATAA CTTTCACCTT GGAACTCGAA TCAGGTCCAT TTTTTTCCAA    2220

ATCACACAAA ATTAAATTTC GCATCCGATA ATCAAGCCAT CTCTTCACTA TGGTTTTAAG    2280

TGTTGCTCAC ACTAGTGTAT TTATGGACTA ATCACCTGTG TATCTCATAC AATAACATAT    2340

CAGTACATCT AAGTTGTTAC TCAATTACCA AAACCGAATT ATAGCCTTCG AAAAAGGTTA    2400

TCGACTAGTC ACTCAATTAC CAAAACTAAA CTTTAGACTT TCATGTATGA CATCCAACAT    2460

GACACTGTAC TGGACTAAAC CACCTTTCAA GCTACACAAG GAGCAAAAAT AACTAATTTT    2520

CGTAGTTGTA GGAGCTAAAG TATATGTCCA CAACAATAGT TAAGGGAAGC CCCCAAGGAC    2580

TTAAAAGTCC TTTTACCTCT TGAAACTTTT GTCGTGGTCT ACTTTTTCAC TTTAAACTTC    2640

AAAATTTGAC ATTTTATCAC CCCTTAACTC TTAAAACCAT TTAAATTACA TTCTTACTAG    2700

ATTATAGATG ATTTTGTTGT GAAAAGTTTT TAAGACATGT TTACACATTG ATTAAAATCA    2760

TTTGTTCAAT TTCCTAGAGT TAAATCTAAT CTTATTAAAA CTATTAGAGA TACTTTCACG    2820

AGCTCTAAAT ATTTTTATTT TTTCATTATG GAATTTTGTT AGAATTCTTA TAGACCTTTT    2880

TTTGTGGTTT AAAAGCCTTG CCATGTTTTT AACAAGTTTT TTTTCTATTT TTTGAAATTT    2940

TCTTGGAAAC CACTTCTAAC CCGGTAGAAG ATTTATTTTG CTACACTTAT ATCTACAACA    3000

AAATCAACTT ATGAAATTGT CTTGGAAACT ACCTCTAACC CGGTAGAATG AATTTGAATG    3060

AAAATTAAAC CAACTTACGG AATCGCCCAA CATATGTCGA TTAAAGTGGA TATGGATACA    3120

TATGAAGAAG CCCTAGAGAT AATCTAAATG GTTTCAGAAT TGAGGGTTAT TTTTTGAAGT    3180

TTGATGGGAA GATAAGACCA TAACGGTAGT TCACAGAGAT AAAAGGGTTA TTTTTTTCAG    3240

AAATATTTGT GCTGCAATTG ATCCTGTGCC TCAAATTCAG CCTGCAACCA AGGCCAGGTT    3300

CTAGAGCGAA CAAGGCCCAC GTCACCCGTG GCCCGTCAGG CGAAGCAGGT CTTGTGCAGA    3360

CTTTGAGAGG GATTGGATAT CAACGGAACC AATCACGCAC GGCAATGCGA TTCCCAGCCC    3420

ACCTGTAACG TTCCAGTGGG CCATCCTTAA CTCCAAGCCC AACGGCCCTA CCCCATCTCG    3480

TCGTGTCATC CACTCCGCCG CACAGGCGCT CAGCTCCGCA ACGCCGCCGG AAATGGTCGC    3540

CGCCACAGCC ACCGCCATGG CCACCGCTGC ATCGCCGCTA CTCAACGGGA CCCGAATACC    3600

TGCGCGGCTC CGCCATCGAG GACTCAGCGT GCGCTGCGCT GCTGTGGCGG GCGGCGCGGC    3660

CGAGGCACCG GCATCCACCG GCGCGCGGCT GTCCGCGGAC TGCGTTGTGG TGGGCGGAGG    3720

CATCAGTGGC CTCTGCACCG CGCAGGCGCT GGCCACGCGG CACGGCGTCG GGACGTGCT    3780

TGTCACGGAG GCCCGCGCCC GCCCCGGCGG CAACATTACC ACCGTCGAGC GCCCCGAGGA    3840

AGGGTACC                                                             3848
```

(2) INFORMATION FOR SEQ ID NO:15:

(i) SEQUENCE CHARACTERISTICS:
        (A) LENGTH: 1826 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Gossypium hirsutum (cotton)

(vii) IMMEDIATE SOURCE:
        (B) CLONE: pWDC-15 (NRRL B-21594)

(ix) FEATURE:
        (A) NAME/KEY: misc_feature
        (B) LOCATION: 31..1647
        (D) OTHER INFORMATION: /product= "Cotton protox-1 coding
           region"

(xi) SEQUENCE DESCRIPTION: SEQ ID NO:15:

```
CCTCTCGCTC GCCTGGCCCC ACCACCAATC ATGACGGCTC TAATCGACCT TTCTCTTCTC      60

CGTTCCTCGC CCTCCGTTTC CCCTTTCTCC ATACCCCACC ACCAGCATCC GCCCCGCTTT     120

CGTAAACCTT TCAAGCTCCG ATGCTCCCTC GCCGAGGGTC CACGATTTC CTCATCTAAA      180

ATCGACGGGG GAGAATCATC CATCGCGGAT TGCGTCATCG TTGGAGGTGG TATCAGTGGA     240

CTTTGCATTG CTCAAGCTCT CGCCACCAAG CACCGTGACG TCGCTTCCAA TGTGATTGTG     300

ACGGAGGCCA GAGACCGTGT TGGTGGCAAC ATCACTACCG TTGAGAGAGA TGGATATCTG     360

TGGGAAGAAG GCCCCAACAG TTTTCAGCCC TCCGATCCTA TTCTAACCAT GGCCGTGGAT     420

AGTGGATTGA AGGACGATTT GGTTTTAGGT GACCCTAATG CACCGCGATT TGTACTATGG     480

GAGGGAAAAC TAAGGCCTGT GCCCTCCAAG CCAACCGACT TGCCGTTTTT TGATTTGATG     540

AGCATTGCTG GAAAACTTAG GGCTGGGTTC GGGGCTATTG GCATTCGGCC TCCCCCTCCG     600

GGTTATGAAG AATCGGTGGA GGAGTTTGTG CGCCGTAATC TTGGTGCTGA GGTTTTTGAA     660

CGCTTTATTG AACCATTTTG TTCAGGTGTT TATGCAGGGG ATCCTTCAAA ATTAAGCATG     720

AAAGCAGCAT TTGGAAGAGT ATGGAAGCTA GAAGAGATTG GTGGCAGCAT CATTGGTGGC     780

ACTTTCAAGA CAATCCAGGA GAGAAATAAG ACACCTAAGC CACCCAGAGA CCCGCGTCTG     840

CCAAAACCGA AGGGCCAAAC AGTTGGATCT TTTAGGAAGG GACTTACCAT GCTGCCTGAG     900

GCAATTGCTA ACAGTTTGGG TAGCAATGTA AAATTATCTT GGAAGCTTTC CAGTATTACC     960

AAATTGGGCA ATGGAGGGTA TAACTTGACA TTTGAAACAC CTGAAGGAAT GGTATCTCTT    1020

CAGAGTAGAA GTGTTGTAAT GACCATTCCA TCCCATGTTG CCAGTAACTT GTTGCATCCT    1080

CTCTCGGCTG CTGCTGCAGA TGCATTATCC CAATTTTATT ATCCTCCAGT TGCATCAGTC    1140

ACAGTCTCCT ATCCAAAAGA AGCCATTCGA AAAGAATGTT TGATTGATGG TGAACTTAAG    1200

GGGTTTGGCC AGTTGCACCC ACGCAGCCAA GGAATTGAAA CTTTAGGGAC GATATACAGT    1260

TCATCACTTT TCCCCAATCG AGCTCCATCT GGCAGGGTGT TGCTCTTGAA CTACATAGGA    1320

GGAGCTACCA ACACTGGAAT TTTGTCCAAG ACTGAAGGGG AACTTGTAGA AGCAGTTGAT    1380

CGTGATTTGA GAAAAATGCT TATAAATCCT AATGCAAAGG ATCCTCTTGT TTTGGGTGTA    1440

AGAGTATGGC CAAAAGCCAT TCCACAGTTC TTGGTTGGTC ATTTGGATCT CCTTGATAGT    1500

GCAAAAATGG CTCTCAGGGA TTCTGGGTTT CATGGACTGT TTCTTGGGGG CAACTATGTA    1560
```

```
TCTGGTGTGG CATTAGGACG GTGTGTGGAA GGTGCTTACG AGGTTGCAGC TGAAGTGAAG      1620

GAATTCCTGT CACAATATGC ATACAAATAA TATTGAAATT CTTGTCAGGC TGCAAATGTA      1680

GAAGTCAGTT ATTGGATAGT ATCTCTTTAG CTAAAAAATT GGGTAGGGTT TTTTTTGTTA      1740

GTTCCTTGAC CACTTTTTGG GGTTTTCATT AGAACTTCAT ATTTGTATAT CATGTTGCAA      1800

TATCAAAAAA AAAAAAAAAA AAAAAA                                          1826
```

(2) INFORMATION FOR SEQ ID NO:16:

(i) SEQUENCE CHARACTERISTICS:
        (A) LENGTH: 539 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:16:

```
Met Thr Ala Leu Ile Asp Leu Ser Leu Leu Arg Ser Ser Pro Ser Val
1               5                  10                  15

Ser Pro Phe Ser Ile Pro His His Gln His Pro Pro Arg Phe Arg Lys
            20                  25                  30

Pro Phe Lys Leu Arg Cys Ser Leu Ala Glu Gly Pro Thr Ile Ser Ser
        35                  40                  45

Ser Lys Ile Asp Gly Gly Glu Ser Ser Ile Ala Asp Cys Val Ile Val
50                  55                  60

Gly Gly Gly Ile Ser Gly Leu Cys Ile Ala Gln Ala Leu Ala Thr Lys
65                  70                  75                  80

His Arg Asp Val Ala Ser Asn Val Ile Val Thr Glu Ala Arg Asp Arg
                85                  90                  95

Val Gly Gly Asn Ile Thr Thr Val Glu Arg Asp Gly Tyr Leu Trp Glu
            100                 105                 110

Glu Gly Pro Asn Ser Phe Gln Pro Ser Asp Pro Ile Leu Thr Met Ala
        115                 120                 125

Val Asp Ser Gly Leu Lys Asp Asp Leu Val Leu Gly Asp Pro Asn Ala
    130                 135                 140

Pro Arg Phe Val Leu Trp Glu Gly Lys Leu Arg Pro Val Pro Ser Lys
145                 150                 155                 160

Pro Thr Asp Leu Pro Phe Phe Asp Leu Met Ser Ile Ala Gly Lys Leu
                165                 170                 175

Arg Ala Gly Phe Gly Ala Ile Gly Ile Arg Pro Pro Pro Pro Gly Tyr
            180                 185                 190

Glu Glu Ser Val Glu Glu Phe Val Arg Arg Asn Leu Gly Ala Glu Val
        195                 200                 205

Phe Glu Arg Phe Ile Glu Pro Phe Cys Ser Gly Val Tyr Ala Gly Asp
    210                 215                 220

Pro Ser Lys Leu Ser Met Lys Ala Ala Phe Gly Arg Val Trp Lys Leu
225                 230                 235                 240

Glu Glu Ile Gly Gly Ser Ile Ile Gly Gly Thr Phe Lys Thr Ile Gln
                245                 250                 255

Glu Arg Asn Lys Thr Pro Lys Pro Pro Arg Asp Pro Arg Leu Pro Lys
            260                 265                 270

Pro Lys Gly Gln Thr Val Gly Ser Phe Arg Lys Gly Leu Thr Met Leu
        275                 280                 285

Pro Glu Ala Ile Ala Asn Ser Leu Gly Ser Asn Val Lys Leu Ser Trp
    290                 295                 300
```

-continued

```
Lys Leu Ser Ser Ile Thr Lys Leu Gly Asn Gly Gly Tyr Asn Leu Thr
305                 310                 315                 320

Phe Glu Thr Pro Glu Gly Met Val Ser Leu Gln Ser Arg Ser Val Val
            325                 330                 335

Met Thr Ile Pro Ser His Val Ala Ser Asn Leu Leu His Pro Leu Ser
            340                 345                 350

Ala Ala Ala Ala Asp Ala Leu Ser Gln Phe Tyr Tyr Pro Pro Val Ala
            355                 360                 365

Ser Val Thr Val Ser Tyr Pro Lys Glu Ala Ile Arg Lys Glu Cys Leu
370                 375                 380

Ile Asp Gly Glu Leu Lys Gly Phe Gly Gln Leu His Pro Arg Ser Gln
385                 390                 395                 400

Gly Ile Glu Thr Leu Gly Thr Ile Tyr Ser Ser Ser Leu Phe Pro Asn
            405                 410                 415

Arg Ala Pro Ser Gly Arg Val Leu Leu Leu Asn Tyr Ile Gly Gly Ala
            420                 425                 430

Thr Asn Thr Gly Ile Leu Ser Lys Thr Glu Gly Glu Leu Val Glu Ala
            435                 440                 445

Val Asp Arg Asp Leu Arg Lys Met Leu Ile Asn Pro Asn Ala Lys Asp
450                 455                 460

Pro Leu Val Leu Gly Val Arg Val Trp Pro Lys Ala Ile Pro Gln Phe
465                 470                 475                 480

Leu Val Gly His Leu Asp Leu Asp Ser Ala Lys Met Ala Leu Arg
                485                 490                 495

Asp Ser Gly Phe His Gly Leu Phe Leu Gly Gly Asn Tyr Val Ser Gly
                500                 505                 510

Val Ala Leu Gly Arg Cys Val Glu Gly Ala Tyr Glu Val Ala Ala Glu
            515                 520                 525

Val Lys Glu Phe Leu Ser Gln Tyr Ala Tyr Lys
530                 535
```

(2) INFORMATION FOR SEQ ID NO:17:

(i) SEQUENCE CHARACTERISTICS:
        (A) LENGTH: 1910 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Beta vulgaris (Sugar Beet)

(vii) IMMEDIATE SOURCE:
        (B) CLONE: pWDC-16 (NRRL B-21595N)

(ix) FEATURE:
        (A) NAME/KEY: misc_feature
        (B) LOCATION: 1..1680
        (D) OTHER INFORMATION: /product= "Sugar Beet Protox-1
           coding region"

(xi) SEQUENCE DESCRIPTION: SEQ ID NO:17:

```
ATGAAATCAA TGGCGTTATC AAACTGCATT CCACAGACAC AGTGCATGCC ATTGCGCAGC      60

AGCGGGCATT ACAGGGGTAA TTGTATCATG TTGTCAATTC CATGTAGTTT AATTGGAAGA     120

CGAGGTTATT ATTCACATAA GAAGAGGAGG ATGAGCATGA GTTGCAGCAC AAGCTCAGGC     180
```

```
TCAAAGTCAG CGGTTAAAGA AGCAGGATCA GGATCAGGTG CAGGAGGATT GCTAGACTGC        240

GTAATCGTTG GAGGTGGAAT TAGCGGGCTT TGCATCGCGC AGGCTCTTTG TACAAAACAC        300

TCCTCTTCCT CTTTATCCCC AAATTTTATA GTTACAGAGG CCAAAGACAG AGTTGGCGGC        360

AACATCGTCA CTGTGGAGGC CGATGGCTAT ATCTGGGAGG AGGGACCCAA TAGCTTCCAG        420

CCTTCCGACG CGGTGCTCAC CATGGCGGTC GACAGTGGCT TGAAAGATGA GTTGGTGCTC        480

GGAGATCCCA ATGCTCCTCG CTTTGTGCTA TGGAATGACA AATTAAGGCC CGTACCTTCC        540

AGTCTCACCG ACCTCCCTTT CTTCGACCTC ATGACCATTC CGGGCAAGAT TAGGGCTGCT        600

CTTGGTGCTC TCGGATTTCG CCCTTCTCCT CCACCTCATG AGGAATCTGT TGAACACTTT        660

GTGCGTCGTA ATCTCGGAGA TGAGGTCTTT GAACGCTTGA TTGAACCCTT TTGTTCAGGT        720

GTGTATGCCG GTGATCCTGC CAAGCTGAGT ATGAAAGCTG CTTTTGGGAA GGTCTGGAAG        780

TTGGAGCAAA AGGGTGGCAG CATAATTGGT GGCACTCTCA AAGCTATACA GGAAAGAGGG        840

AGTAATCCTA AGCCGCCCCG TGACCAGCGC CTCCCTAAAC CAAAGGGTCA GACTGTTGGA        900

TCCTTTAGAA AGGGACTCGT TATGTTGCCT ACCGCCATTT CTGCTCGACT TGGCAGTAGA        960

GTGAAACTAT CTTGGACCCT TTCTAGTATC GTAAAGTCAC TCAATGGAGA ATATAGTCTG       1020

ACTTATGATA CCCCAGATGG CTTGGTTTCT GTAAGAACCA AAAGTGTTGT GATGACTGTT       1080

CCATCATATG TTGCAAGTAG GCTTCTTCGT CCACTTTCAG ACTCTGCTGC AGATTCTCTT       1140

TCAAAATTTT ACTATCCACC AGTTGCAGCA GTGTCACTTT CCTATCCTAA AGAAGCGATC       1200

AGATCAGAAT GCTTGATTAA TGGTGAACTT CAAGGTTTCG GGCAACTACA TCCCCGCAGT       1260

CAGGGTGTGG AAACCTTGGG AACAATTTAT AGTTCGTCTC TTTTCCCTGG TCGAGCACCA       1320

CCTGGTAGGA TCTTGATCTT GAGCTACATC GGAGGTGCTA AAAATCCTGG CATATTAAAC       1380

AAGTCGAAAG ATGAACTTGC CAAGACAGTT GACAAGGACC TGAGAAGAAT GCTTATAAAT       1440

CCTGATGCAA AACTTCCTCG TGTACTGGGT GTGAGAGTAT GGCCTCAAGC AATACCCCAG       1500

TTTTCTATTG GCACTTTGA TCTGCTCGAT GCTGCAAAAG CTGCTCTGAC AGATACAGGG       1560

GTCAAAGGAC TGTTTCTTGG TGGCAACTAT GTTTCAGGTG TTGCCTTGGG GCGGTGTATA       1620

GAGGGTGCTT ATGAGTCTGC AGCTGAGGTA GTAGATTTCC TCTCACAGTA CTCAGACAAA       1680

TAGAGCTTCA GCATCCTGTG TAATTCAACA CAGGCCTTTT TGTATCTGTT GTGCGCGCAT       1740

GTAGTCTGGT CGTGGTGCTA GGATTGATTA GTTGCTCTGC TGTGTGATCC ACAAGAATTT       1800

TGATGGAATT TTTCCAGATG TGGGCATTAT ATGTTGCTGT CTTATAAATC CTTAATTTGT       1860

ACGTTTAGTG AATTACACCG CATTTGATGA CTAAAAAAAA AAAAAAAAA                   1910
```

(2) INFORMATION FOR SEQ ID NO:18:

(i) SEQUENCE CHARACTERISTICS:
        (A) LENGTH: 560 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:18:

```
Met Lys Ser Met Ala Leu Ser Asn Cys Ile Pro Gln Thr Gln Cys Met
1               5                   10                  15

Pro Leu Arg Ser Ser Gly His Tyr Arg Gly Asn Cys Ile Met Leu Ser
            20                  25                  30

Ile Pro Cys Ser Leu Ile Gly Arg Arg Gly Tyr Tyr Ser His Lys Lys
        35                  40                  45
```

```
Arg Arg Met Ser Met Ser Cys Ser Thr Ser Ser Gly Ser Lys Ser Ala
 50              55                  60

Val Lys Glu Ala Gly Ser Gly Ser Gly Ala Gly Gly Leu Leu Asp Cys
 65              70                  75                      80

Val Ile Val Gly Gly Ile Ser Gly Leu Cys Ile Ala Gln Ala Leu
             85                  90                  95

Cys Thr Lys His Ser Ser Ser Leu Ser Pro Asn Phe Ile Val Thr
             100                 105             110

Glu Ala Lys Asp Arg Val Gly Gly Asn Ile Val Thr Val Glu Ala Asp
             115             120                 125

Gly Tyr Ile Trp Glu Glu Gly Pro Asn Ser Phe Gln Pro Ser Asp Ala
     130             135                 140

Val Leu Thr Met Ala Val Asp Ser Gly Leu Lys Asp Glu Leu Val Leu
 145             150                 155                     160

Gly Asp Pro Asn Ala Pro Arg Phe Val Leu Trp Asn Asp Lys Leu Arg
                 165                 170                 175

Pro Val Pro Ser Ser Leu Thr Asp Leu Pro Phe Phe Asp Leu Met Thr
             180                 185                 190

Ile Pro Gly Lys Ile Arg Ala Ala Leu Gly Ala Leu Gly Phe Arg Pro
         195                 200                 205

Ser Pro Pro His Glu Glu Ser Val Glu His Phe Val Arg Arg Asn
 210                 215                 220

Leu Gly Asp Glu Val Phe Glu Arg Leu Ile Glu Pro Phe Cys Ser Gly
 225                 230                 235                 240

Val Tyr Ala Gly Asp Pro Ala Lys Leu Ser Met Lys Ala Ala Phe Gly
                 245                 250                 255

Lys Val Trp Lys Leu Glu Gln Lys Gly Gly Ser Ile Ile Gly Gly Thr
                 260                 265                 270

Leu Lys Ala Ile Gln Glu Arg Gly Ser Asn Pro Lys Pro Pro Arg Asp
         275                 280                 285

Gln Arg Leu Pro Lys Pro Lys Gly Gln Thr Val Gly Ser Phe Arg Lys
     290                 295                 300

Gly Leu Val Met Leu Pro Thr Ala Ile Ser Ala Arg Leu Gly Ser Arg
 305                 310                 315                 320

Val Lys Leu Ser Trp Thr Leu Ser Ser Ile Val Lys Ser Leu Asn Gly
                 325                 330                 335

Glu Tyr Ser Leu Thr Tyr Asp Thr Pro Asp Gly Leu Val Ser Val Arg
                 340                 345                 350

Thr Lys Ser Val Val Met Thr Val Pro Ser Tyr Val Ala Ser Arg Leu
                 355                 360                 365

Leu Arg Pro Leu Ser Asp Ser Ala Ala Asp Ser Leu Ser Lys Phe Tyr
     370                 375                 380

Tyr Pro Pro Val Ala Ala Val Ser Leu Ser Tyr Pro Lys Glu Ala Ile
 385                 390                 395                 400

Arg Ser Glu Cys Leu Ile Asn Gly Glu Leu Gln Gly Phe Gly Gln Leu
                 405                 410                 415

His Pro Arg Ser Gln Gly Val Glu Thr Leu Gly Thr Ile Tyr Ser Ser
                 420                 425                 430

Ser Leu Phe Pro Gly Arg Ala Pro Pro Gly Arg Ile Leu Ile Leu Ser
             435                 440                 445

Tyr Ile Gly Gly Ala Lys Asn Pro Gly Ile Leu Asn Lys Ser Lys Asp
     450                 455                 460

Glu Leu Ala Lys Thr Val Asp Lys Asp Leu Arg Arg Met Leu Ile Asn
 465                 470                 475                 480
```

```
Pro Asp Ala Lys Leu Pro Arg Val Leu Gly Val Arg Val Trp Pro Gln
            485                 490                 495

Ala Ile Pro Gln Phe Ser Ile Gly His Phe Asp Leu Leu Asp Ala Ala
            500                 505                 510

Lys Ala Ala Leu Thr Asp Thr Gly Val Lys Gly Leu Phe Leu Gly Gly
            515                 520                 525

Asn Tyr Val Ser Gly Val Ala Leu Gly Arg Cys Ile Glu Gly Ala Tyr
    530                 535                 540

Glu Ser Ala Ala Glu Val Val Asp Phe Leu Ser Gln Tyr Ser Asp Lys
545                 550                 555                 560

(2) INFORMATION FOR SEQ ID NO:19:

(i) SEQUENCE CHARACTERISTICS:
        (A) LENGTH: 1784 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Brassica napus (rape)

(vii) IMMEDIATE SOURCE:
        (B) CLONE: pWDC-17 (NRRL B-21615)

(ix) FEATURE:
        (A) NAME/KEY: misc_feature
        (B) LOCATION: 47..1654
        (D) OTHER INFORMATION: /product= "Rape Protox-1 coding
            region"

(xi) SEQUENCE DESCRIPTION: SEQ ID NO:19:

GGGCCCCCCC CAAAATTGAG GATTCTCCTT CTCGCGGGCG ATCGCCATGG ATTTATCTCT    60

TCTCCGTCCG CAGCCATTCC TATCGCCATT CTCAAATCCA TTTCCTCGGT CGCGTCCCTA   120

CAAGCCTCTC AACCTCCGTT GCTCCGTATC CGGTGGATCC GTCGTCGGCT CTTCTACAAT   180

CGAAGGCGGA GGAGGAGGTA AAACCGTCAC GGCGGACTGC GTGATCGTCG GCGGAGGAAT   240

CAGCGGCCTG TGCATTGCGC AAGCGCTCGT GACGAAGCAC CCAGACGCTG CAAAGAATGT   300

GATGGTGACG GAGGCGAAGG ACCGTGTGGG AGGGAATATC ATCACGCGAG AGGAGCAAGG   360

GTTTCTATGG GAAGAAGGTC CCAATAGCTT TCAGCCGTCT GATCCTATGC TCACTATGGT   420

GGTAGATAGT GGTTTGAAAG ATGATCTAGT CTTGGGAGAT CCTACTGCTC GAGGTTTGT   480

GTTGTGGAAT GGGAAGCTGA GGCCGGTTCC GTCGAAGCTA ACTGACTTGC CTTTCTTTGA   540

CTTGATGAGT ATTGGAGGGA AGATTAGAGC TGGGTTTGGT GCCATTGGTA TTCGACCTTC   600

ACCTCCGGGT CGTGAGGAAT CAGTGGAAGA GTTTGTAAGG CGTAATCTTG GTGATGAGGT   660

TTTTGAGCGC TTGATTGAAC CCTTTTGCTC AGGTGTTTAT GCGGGAGATC CTGCGAAACT   720

GAGTATGAAA GCAGCTTTTG GAAGGTTTG GAAGCTAGAG GAGAATGGTG GGAGCATCAT   780

TGGTGGTGCT TTTAAGGCAA TTCAAGCGAA AAATAAAGCT CCCAAGACAA CCCGAGATCC   840

GCGTCTGCCA AAGCCAAAGG GCCAAACTGT TGGTTCTTTC AGGAAAGGAC TCACAATGCT   900

GCCAGAGGCA ATCCCGCAA GGTTGGGTGA CAAGGTGAAA GTTTCTTGGA AGCTCTCAAG   960

TATCACTAAG CTGGCCAGCG GAGAATATAG CTTAACTTAC GAAACTCCGG AGGGTATAGT  1020

CACTGTACAG AGCAAAAGTG TAGTGATGAC TGTGCCATCT CATGTTGCTA GTAGTCTCTT  1080
```

```
GCGCCCTCTC TCTGATTCTG CAGCTGAAGC GCTCTCAAAA CTCTACTATC CGCCAGTTGC      1140

AGCCGTATCC ATCTCATACG CGAAAGAAGC AATCCGAAGC GAATGCTTAA TAGATGGTGA      1200

ACTAAAAGGG TTCGGCCAGT TGCATCCACG CACGCAAAAA GTGGAAACTC TTGGAACAAT      1260

ATACAGTTCA TCGCTCTTTC CCAACCGAGC ACCGCCTGGA AGAGTATTGC TATTGAACTA      1320

CATCGGTGGA GCTACCAACA CTGGGATCTT ATCAAAGTCG GAAGGTGAGT TAGTGGAAGC      1380

AGTAGATAGA GACTTGAGGA AGATGCTGAT AAAGCCAAGC TCGACCGATC CACTTGTACT      1440

TGGAGTAAAA TTATGGCCTC AAGCCATTCC TCAGTTTCTG ATAGGTCACA TTGATTTGGT      1500

AGACGCAGCG AAAGCATCGC TCTCGTCATC TGGTCATGAG GGCTTATTCT TGGGTGGAAA      1560

TTACGTTGCC GGTGTAGCAT TGGGTCGGTG TGTGGAAGGT GCTTATGAAA CTGCAACCCA      1620

AGTGAATGAT TCATGTCAA GGTATGCTTA CAAGTAATGT AACGCAGCAA CGATTTGATA       1680

CTAAGTAGTA GATTTTGCAG TTTTGACTTT AAGAACACTC TGTTTGTGAA AAATTCAAGT      1740

CTGTGATTGA GTAAATTTAT GTATTATTAC TAAAAAAAAA AAAA                      1784
```

(2) INFORMATION FOR SEQ ID NO:20:

(i) SEQUENCE CHARACTERISTICS:
        (A) LENGTH: 536 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:20:

```
Met Asp Leu Ser Leu Leu Arg Pro Gln Pro Phe Leu Ser Pro Phe Ser
 1               5                  10                  15

Asn Pro Phe Pro Arg Ser Arg Pro Tyr Lys Pro Leu Asn Leu Arg Cys
                20                  25                  30

Ser Val Ser Gly Gly Ser Val Gly Ser Ser Thr Ile Glu Gly Gly
            35                  40                  45

Gly Gly Gly Lys Thr Val Thr Ala Asp Cys Val Ile Val Gly Gly
        50                  55                  60

Ile Ser Gly Leu Cys Ile Ala Gln Ala Leu Val Thr Lys His Pro Asp
65                  70                  75                  80

Ala Ala Lys Asn Val Met Val Thr Glu Ala Lys Asp Arg Val Gly Gly
                85                  90                  95

Asn Ile Ile Thr Arg Glu Glu Gln Gly Phe Leu Trp Glu Gly Pro
                100                 105                 110

Asn Ser Phe Gln Pro Ser Asp Pro Met Leu Thr Met Val Val Asp Ser
            115                 120                 125

Gly Leu Lys Asp Asp Leu Val Leu Gly Asp Pro Thr Ala Pro Arg Phe
        130                 135                 140

Val Leu Trp Asn Gly Lys Leu Arg Pro Val Pro Ser Lys Leu Thr Asp
145                 150                 155                 160

Leu Pro Phe Phe Asp Leu Met Ser Ile Gly Lys Ile Arg Ala Gly
                165                 170                 175

Phe Gly Ala Ile Gly Ile Arg Pro Ser Pro Gly Arg Glu Glu Ser
            180                 185                 190

Val Glu Glu Phe Val Arg Arg Asn Leu Gly Asp Glu Val Phe Glu Arg
        195                 200                 205

Leu Ile Glu Pro Phe Cys Ser Gly Val Tyr Ala Gly Asp Pro Ala Lys
    210                 215                 220
```

```
Leu Ser Met Lys Ala Ala Phe Gly Lys Val Trp Lys Leu Glu Glu Asn
225                 230                 235                 240

Gly Gly Ser Ile Ile Gly Gly Ala Phe Lys Ala Ile Gln Ala Lys Asn
            245                 250                 255

Lys Ala Pro Lys Thr Thr Arg Asp Pro Arg Leu Pro Lys Pro Lys Gly
        260                 265                 270

Gln Thr Val Gly Ser Phe Arg Lys Gly Leu Thr Met Leu Pro Glu Ala
    275                 280                 285

Ile Ser Ala Arg Leu Gly Asp Lys Val Lys Val Ser Trp Lys Leu Ser
290                 295                 300

Ser Ile Thr Lys Leu Ala Ser Gly Glu Tyr Ser Leu Thr Tyr Glu Thr
305                 310                 315                 320

Pro Glu Gly Ile Val Thr Val Gln Ser Lys Ser Val Val Met Thr Val
                325                 330                 335

Pro Ser His Val Ala Ser Ser Leu Leu Arg Pro Leu Ser Asp Ser Ala
            340                 345                 350

Ala Glu Ala Leu Ser Lys Leu Tyr Tyr Pro Pro Val Ala Ala Val Ser
        355                 360                 365

Ile Ser Tyr Ala Lys Glu Ala Ile Arg Ser Glu Cys Leu Ile Asp Gly
    370                 375                 380

Glu Leu Lys Gly Phe Gly Gln Leu His Pro Arg Thr Gln Lys Val Glu
385                 390                 395                 400

Thr Leu Gly Thr Ile Tyr Ser Ser Ser Leu Phe Pro Asn Arg Ala Pro
                405                 410                 415

Pro Gly Arg Val Leu Leu Leu Asn Tyr Ile Gly Gly Ala Thr Asn Thr
            420                 425                 430

Gly Ile Leu Ser Lys Ser Glu Gly Glu Leu Val Glu Ala Val Asp Arg
        435                 440                 445

Asp Leu Arg Lys Met Leu Ile Lys Pro Ser Ser Thr Asp Pro Leu Val
450                 455                 460

Leu Gly Val Lys Leu Trp Pro Gln Ala Ile Pro Gln Phe Leu Ile Gly
465                 470                 475                 480

His Ile Asp Leu Val Asp Ala Ala Lys Ala Ser Leu Ser Ser Ser Gly
                485                 490                 495

His Glu Gly Leu Phe Leu Gly Gly Asn Tyr Val Ala Gly Val Ala Leu
            500                 505                 510

Gly Arg Cys Val Glu Gly Ala Tyr Glu Thr Ala Thr Gln Val Asn Asp
        515                 520                 525

Phe Met Ser Arg Tyr Ala Tyr Lys
530                 535

(2) INFORMATION FOR SEQ ID NO:21:

(i) SEQUENCE CHARACTERISTICS:
        (A) LENGTH: 1224 base pairs
        (B) TYPE: nucleic acid
        (C) STRANDEDNESS: single
        (D) TOPOLOGY: linear (ii) MOLECULE TYPE: cDNA (iii) HYPOTHETICAL: NO (iv) ANTI-SENSE: NO (vi) ORIGINAL SOURCE:
        (A) ORGANISM: Oryza sative (rice)

(vii) IMMEDIATE SOURCE:
        (B) CLONE: pWDC-18 (NRRL B-21648)
```

-continued (ix) FEATURE:
   (A) NAME/KEY: misc_feature
   (B) LOCATION: 1..936
   (D) OTHER INFORMATION: /product= "Rice Protox-1 partial
       coding region"

(xi) SEQUENCE DESCRIPTION: SEQ ID NO:21:

```
CGGGCTTTGA AGGCTGCATT TGGGAAGGTG TGGAGGCTGG AGGATACTGG AGGTAGCATT      60
ATTGGTGGAA CCATCAAGAC AATCCAGGAG AGGGGGAAAA ACCCCAAACC GCCGAGGGAT     120
CCCCGCCTTC AACGCCAAA GGGGCAGACA GTTGCATCTT TCAGGAAGGG TCTGACTATG      180
CTCCCGGATG CTATTACATC TAGGTTGGGT AGCAAAGTCA AACTTTCATG GAAGTTGACA     240
AGCATTACAA AGTCAGACAA CAAAGGATAT GCATTAGTGT ATGAAACACC AGAAGGGGTG     300
GTCTCGGTGC AAGCTAAAAC TGTTGTCATG ACCATCCCAT CATATGTTGC TAGTGATATC     360
TTGCGGCCAC TTTCAAGTGA TGCAGCAGAT GCTCTGTCAA TATTCTATTA TCCACCAGTT     420
GCTGCTGTAA CTGTTTCATA TCCAAAAGAA GCAATTAGAA AAGAATGCTT AATTGACGGA     480
GAGCTCCAGG GTTTCGGCCA GCTGCATCCG CGTAGTCAGG GAGTTGAGAC TTTAGGAACA     540
ATATATAGCT CATCACTCTT TCCAAATCGT GCTCCAGCTG GAAGGGTGTT ACTTCTGAAC     600
TACATAGGAG GTTCTACAAA TACAGGGATT GTTTCCAAGA CTGAAAGTGA GCTGGTAGAA     660
GCAGTTGACC GTGACCTCAG GAAGATGCTG ATAAATCCTA GAGCAGTGGA CCCTTTGGTC     720
CTTGGCGTCC GGGTATGGCC ACAAGCCATA CCACAGTTCC TCATTGGCCA TCTTGATCAT     780
CTTGAGGCTG CAAAATCTGC CCTGGGCAAA GGTGGGTATG ATGGATTGTT CCTCGGAGGG     840
AACTATGTTG CAGGAGTTGC CCTGGGCCGA TGCGTTGAAG GTGCATATGA GAGTGCCTCA     900
CAAATATCTG ACTACTTGAC CAAGTACGCC TACAAGTGAT CAAAGTTGGC CTGCTCCTTT     960
TGGCACATAG ATGTGAGGCT TCTAGCAGCA AAAATTTCAT GGGCATCTTT TTATCCTGAT    1020
TCTAATTAGT TAGAATTTAG AATTGTAGAG GAATGTTCCA TTTGCAGTTC ATAATAGTTG    1080
TTCAGATTTC AGCCATTCAA TTTGTGCAGC CATTTACTAT ATGTAGTATG ATCTTGTAAG    1140
TACTACTAAG AACAAATCAA TTATATTTTC CTGCAAGTGA CATCTTAATC GTCAGCAAAT    1200
CCAGTTACTA GTAAAAAAAA AAAA                                           1224
```

(2) INFORMATION FOR SEQ ID NO:22:

(i) SEQUENCE CHARACTERISTICS:
       (A) LENGTH: 312 amino acids
       (B) TYPE: amino acid
       (C) STRANDEDNESS: Not Relevant
       (D) TOPOLOGY: Not Relevant (ii) MOLECULE TYPE: protein (xi) SEQUENCE DESCRIPTION: SEQ ID NO:22:

```
Arg Ala Leu Lys Ala Ala Phe Gly Lys Val Trp Arg Leu Glu Asp Thr
 1               5                  10                  15

Gly Gly Ser Ile Ile Gly Gly Thr Ile Lys Thr Ile Gln Glu Arg Gly
                20                  25                  30

Lys Asn Pro Lys Pro Pro Arg Asp Pro Arg Leu Pro Thr Pro Lys Gly
            35                  40                  45

Gln Thr Val Ala Ser Phe Arg Lys Gly Leu Thr Met Leu Pro Asp Ala
        50                  55                  60

Ile Thr Ser Arg Leu Gly Ser Lys Val Lys Leu Ser Trp Lys Leu Thr
65                  70                  75                  80
```

```
Ser Ile Thr Lys Ser Asp Asn Lys Gly Tyr Ala Leu Val Tyr Glu Thr
             85                  90                  95

Pro Glu Gly Val Val Ser Val Gln Ala Lys Thr Val Val Met Thr Ile
           100                 105                 110

Pro Ser Tyr Val Ala Ser Asp Ile Leu Arg Pro Leu Ser Ser Asp Ala
       115                 120                 125

Ala Asp Ala Leu Ser Ile Phe Tyr Tyr Pro Pro Val Ala Ala Val Thr
    130                 135                 140

Val Ser Tyr Pro Lys Glu Ala Ile Arg Lys Glu Cys Leu Ile Asp Gly
145                 150                 155                 160

Glu Leu Gln Gly Phe Gly Gln Leu His Pro Arg Ser Gln Gly Val Glu
                165                 170                 175

Thr Leu Gly Thr Ile Tyr Ser Ser Ser Leu Phe Pro Asn Arg Ala Pro
            180                 185                 190

Ala Gly Arg Val Leu Leu Leu Asn Tyr Ile Gly Gly Ser Thr Asn Thr
        195                 200                 205

Gly Ile Val Ser Lys Thr Glu Ser Glu Leu Val Glu Ala Val Asp Arg
    210                 215                 220

Asp Leu Arg Lys Met Leu Ile Asn Pro Arg Ala Val Asp Pro Leu Val
225                 230                 235                 240

Leu Gly Val Arg Val Trp Pro Gln Ala Ile Pro Gln Phe Leu Ile Gly
                245                 250                 255

His Leu Asp His Leu Glu Ala Ala Lys Ser Ala Leu Gly Lys Gly Gly
            260                 265                 270

Tyr Asp Gly Leu Phe Leu Gly Gly Asn Tyr Val Ala Gly Val Ala Leu
        275                 280                 285

Gly Arg Cys Val Glu Gly Ala Tyr Glu Ser Ala Ser Gln Ile Ser Asp
    290                 295                 300

Tyr Leu Thr Lys Tyr Ala Tyr Lys
305                 310

(2) INFORMATION FOR SEQ ID NO:23:

(i) SEQUENCE CHARACTERISTICS:
         (A) LENGTH: 1590 base pairs
         (B) TYPE: nucleic acid
         (C) STRANDEDNESS: single
         (D) TOPOLOGY: linear (ii) MOLECULE TYPE: cDNA (iii) HYPOTHETICAL: NO (iv) ANTI-SENSE: NO (vi) ORIGINAL SOURCE:
         (A) ORGANISM: Sorghum bicolor (sorghum)

(vii) IMMEDIATE SOURCE:
         (B) CLONE: pWDC-19 (NRRL B-21649)

(ix) FEATURE:
         (A) NAME/KEY: misc_feature
         (B) LOCATION: 1..1320
         (D) OTHER INFORMATION: /product= "Sorghum Protox-1 partial
             coding region"

(xi) SEQUENCE DESCRIPTION: SEQ ID NO:23:

TCCACCGTCG AGCGCCCCGA GGAAGGGTAC CTCTGGGAGG AGGGTCCCAA CAGCTTCCAG      60

CCATCCGACC CCGTTCTCTC CATGGCCGTG GACAGCGGGC TGAAGGATGA CCTGGTTTTT    120

GGGGACCCCA ACGCGCCACG GTTCGTGCTG TGGGAGGGGA AGCTGAGGCC CGTGCCATCC    180
```

-continued

```
AAGCCCGCCG ACCTCCCGTT CTTCGATCTC ATGAGCATCC CTGGCAAGCT CAGGGCCGGT      240

CTCGGCGCGC TTGGCATCCG CCCGCCTGCT CCAGGCCGCG AGGAGTCAGT GGAGGAGTTT      300

GTGCGCCGCA ACCTCGGTGC TGAGGTCTTT GAGCGCCTAA TTGAGCCTTT CTGCTCAGGT      360

GTCTATGCTG GCGATCCTTC CAAGCTCAGT ATGAAGGCTG CATTTGGGAA GGTGTGGCGG      420

TTAGAAGAAG CTGGAGGTAG TATTATTGGT GGAACCATCA AGACGATTCA GGAGAGGGGC      480

AAGAATCCAA AACCACCGAG GGATCCCCGC CTTCCGAAGC CAAAAGGGCA GACAGTTGCA      540

TCTTTCAGGA AGGGTCTTGC CATGCTTCCA AATGCCATCA CATCCAGCTT GGGTAGTAAA      600

GTCAAACTAT CATGGAAACT CACGAGCATG ACAAAATCAG ATGGCAAGGG GTATGTTTTG      660

GAGTATGAAA CACCAGAAGG GGTTGTTTTG GTGCAGGCTA AAAGTGTTAT CATGACCATT      720

CCATCATATG TTGCTAGCGA CATTTTGCGT CCACTTTCAG GTGATGCTGC AGATGTTCTA      780

TCAAGATTCT ATTATCCACC AGTTGCTGCT GTAACGGTTT CGTATCCAAA GGAAGCAATT      840

AGAAAAGAAT GCTTAATTGA TGGGGAACTC CAGGGTTTTG GCCAGTTGCA TCCACGTAGT      900

CAAGGAGTTG AGACATTAGG AACAATATAC AGCTCATCAC TCTTTCCAAA TCGTGCTCCT      960

GCTGGTAGGG TGTTACTTCT AAACTACATA GGAGGTGCTA CAAACACAGG AATTGTTTCC     1020

AAGACTGAAA GTGAGCTGGT AGAAGCAGTT GACCGTGACC TCCGAAAAAT GCTTATAAAT     1080

CCTACAGCAG TGGACCCTTT AGTCCTTGGT GTCCGAGTTT GGCCACAAGC CATACCTCAG     1140

TTCCTGGTAG ACATCTTGA TCTTCTGGAG GCCGCAAAAT CTGCCCTGGA CCAAGGTGGC      1200

TATAATGGGC TGTTCCTAGG AGGGAACTAT GTTGCAGGAG TTGCCCTGGG CAGATGCATT     1260

GAGGGCGCAT ATGAGAGTGC CGCGCAAATA TATGACTTCT TGACCAAGTA CGCCTACAAG     1320

TGATGGAAGA AGTGGAGCGC TGCTTGTTAA TTGTTATGTT GCATAGATGA GGTGAGACCA     1380

GGAGTAGTAA AAGGCGTCAC GAGTATTTTT CATTCTTATT TTGTAAATTG CACTTCTGTT     1440

TTTTTTTCCT GTCAGTAATT AGTTAGATTT TAGTTATGTA GGAGATTGTT GTGTTCACTG     1500

CCCTACAAAA GAATTTTTAT TTTGCATTCG TTTATGAGAG CTGTGCAGAC TTATGTAACG     1560

TTTTACTGTA AGTATCAACA AAATCAAATA                                     1590
```

(2) INFORMATION FOR SEQ ID NO:24:

(i) SEQUENCE CHARACTERISTICS:
        (A) LENGTH: 440 amino acids
        (B) TYPE: amino acid
        (C) STRANDEDNESS: Not Relevant
        (D) TOPOLOGY: Not Relevant (ii) MOLECULE TYPE: protein (xi) SEQUENCE DESCRIPTION: SEQ ID NO:24:

```
Ser Thr Val Glu Arg Pro Glu Glu Gly Tyr Leu Trp Glu Glu Gly Pro
  1               5                  10                  15

Asn Ser Phe Gln Pro Ser Asp Pro Val Leu Ser Met Ala Val Asp Ser
             20                  25                  30

Gly Leu Lys Asp Asp Leu Val Phe Gly Asp Pro Asn Ala Pro Arg Phe
         35                  40                  45

Val Leu Trp Glu Gly Lys Leu Arg Pro Val Pro Ser Lys Pro Ala Asp
     50                  55                  60

Leu Pro Phe Phe Asp Leu Met Ser Ile Pro Gly Lys Leu Arg Ala Gly
 65                  70                  75                  80

Leu Gly Ala Leu Gly Ile Arg Pro Pro Ala Pro Gly Arg Glu Glu Ser
                 85                  90                  95
```

-continued

```
Val Glu Glu Phe Val Arg Arg Asn Leu Gly Ala Glu Val Phe Glu Arg
            100                 105                 110

Leu Ile Glu Pro Phe Cys Ser Gly Val Tyr Ala Gly Asp Pro Ser Lys
        115                 120                 125

Leu Ser Met Lys Ala Ala Phe Gly Lys Val Trp Arg Leu Glu Glu Ala
    130                 135                 140

Gly Gly Ser Ile Ile Gly Gly Thr Ile Lys Thr Ile Gln Glu Arg Gly
145                 150                 155                 160

Lys Asn Pro Lys Pro Pro Arg Asp Pro Arg Leu Pro Lys Pro Lys Gly
                165                 170                 175

Gln Thr Val Ala Ser Phe Arg Lys Gly Leu Ala Met Leu Pro Asn Ala
            180                 185                 190

Ile Thr Ser Ser Leu Gly Ser Lys Val Lys Leu Ser Trp Lys Leu Thr
        195                 200                 205

Ser Met Thr Lys Ser Asp Gly Lys Gly Tyr Val Leu Glu Tyr Glu Thr
    210                 215                 220

Pro Glu Gly Val Val Leu Val Gln Ala Lys Ser Val Ile Met Thr Ile
225                 230                 235                 240

Pro Ser Tyr Val Ala Ser Asp Ile Leu Arg Pro Leu Ser Gly Asp Ala
                245                 250                 255

Ala Asp Val Leu Ser Arg Phe Tyr Tyr Pro Pro Val Ala Ala Val Thr
            260                 265                 270

Val Ser Tyr Pro Lys Glu Ala Ile Arg Lys Glu Cys Leu Ile Asp Gly
        275                 280                 285

Glu Leu Gln Gly Phe Gly Gln Leu His Pro Arg Ser Gln Gly Val Glu
    290                 295                 300

Thr Leu Gly Thr Ile Tyr Ser Ser Ser Leu Phe Pro Asn Arg Ala Pro
305                 310                 315                 320

Ala Gly Arg Val Leu Leu Leu Asn Tyr Ile Gly Gly Ala Thr Asn Thr
                325                 330                 335

Gly Ile Val Ser Lys Thr Glu Ser Glu Leu Val Glu Ala Val Asp Arg
            340                 345                 350

Asp Leu Arg Lys Met Leu Ile Asn Pro Thr Ala Val Asp Pro Leu Val
        355                 360                 365

Leu Gly Val Arg Val Trp Pro Gln Ala Ile Pro Gln Phe Leu Val Gly
    370                 375                 380

His Leu Asp Leu Leu Glu Ala Ala Lys Ser Ala Leu Asp Gln Gly Gly
385                 390                 395                 400

Tyr Asn Gly Leu Phe Leu Gly Gly Asn Tyr Val Ala Gly Val Ala Leu
                405                 410                 415

Gly Arg Cys Ile Glu Gly Ala Tyr Glu Ser Ala Ala Gln Ile Tyr Asp
            420                 425                 430

Phe Leu Thr Lys Tyr Ala Tyr Lys
    435                 440
```

(2) INFORMATION FOR SEQ ID NO:25:

(i) SEQUENCE CHARACTERISTICS:
        (A) LENGTH: 93 base pairs
        (B) TYPE: nucleic acid
        (C) STRANDEDNESS: single
        (D) TOPOLOGY: linear (ii) MOLECULE TYPE: other nucleic acid
        (A) DESCRIPTION: /desc = "maize protox-1 intron
            sequence"

(xi) SEQUENCE DESCRIPTION: SEQ ID NO:25:

```
GTACGCTCCT CGCTGGCGCC GCAGCGTCTT CTTCTCAGAC TCATGCGCAG CCATGGAATT      60

GAGATGCTGA ATGGATTTTA TACGCGCGCG CAG                                   93

(2) INFORMATION FOR SEQ ID NO:26:

(i) SEQUENCE CHARACTERISTICS:
        (A) LENGTH: 2606 base pairs
        (B) TYPE: nucleic acid
        (C) STRANDEDNESS: single
        (D) TOPOLOGY: linear (ii) MOLECULE TYPE: DNA (genomic)

(iii) HYPOTHETICAL: NO (iv) ANTI-SENSE: NO (vi) ORIGINAL SOURCE:
        (A) ORGANISM: Beta vulgaris (sugar beet)

(vii) IMMEDIATE SOURCE:
        (B) CLONE: pWDC-20 (NRRL B-21650)

(ix) FEATURE:
        (A) NAME/KEY: misc_feature
        (B) LOCATION: 1..6
        (D) OTHER INFORMATION: /note= "SalI site"

(ix) FEATURE:
        (A) NAME/KEY: misc_feature
        (B) LOCATION: complement (1..538)
        (D) OTHER INFORMATION: /note= "partial cDNA of sugar beet
            protox-1 in 3' - 5' direction"

(ix) FEATURE:
        (A) NAME/KEY: misc_feature
        (B) LOCATION: 539..2606
        (D) OTHER INFORMATION: /note= "sugar beet protox-1
            promoter region presented in 3' - 5' direction (partial
            sequence of the [ ] 3 kb PstI-SalI fragment subcloned from
            pWDC-20)"

(xi) SEQUENCE DESCRIPTION: SEQ ID NO:26:

GTCGACCTAC GCACATGCCA CATTCCACAT TCCACGTTAG GAATTGAATT GAATTGAATT       60

ATGATTATGA ATAATGAAGA GACAGAATTA CCGCCATGGT GAGCACCGCG TCGGAAGGCT      120

GGAAGCTATT GGGTCCCTCC TCCCAGATAT AGCCATCGGC CTCCACAGTG ACGATGTTGC      180

CGCCAACTCT GTCTTTGGCC TCTGTCACTA TAAAATTTGG GGATAAAGAG GACTGTTTTG      240

TACAAAGAGC CTGCGCGATG CAAAGCCCGC TAATTCCACC TCCAACGATT ACGCAGTCTA      300

GCAATCCTCC TGCTCCTGAT CCTGATCCTG ATCCTGCTTC TTTAACCGCT GACTTTGAGC      360

CTGAGCTTGT GCTGCAACTC ATGCTCATCC TCCTCTTCTT ATGTGAATAA TAACCTCGTC      420

TTCCAATTAA ACTACATGGA ATTGACAACA TGATACAATT GCCCCTGTAA TGCCCGCTGC      480

TGTGCAATGG CATGCACTGT GTCTGTGGAA TGCAGTTTGA TAACGCCATT GATTTCATCT      540

CTCTCTCGCT CTCTCGCCCT CCTTATCCTC TATATCCCCT TCTTGCTTGC TCGGGAATTC      600

TAATTAACCT TATATCAAAA TGAAACAACT GTTTCTAGTT AAAAAGTTTT TTATAAATAG      660

TACTCTAAAT AAACGATTAC ATGTATCTTC TAACCATACT TGTTTGGTGG AGGTGGTGCG      720

TAACCGGTAA CTTACCTTTG TAACTCACCT CAATACCTAC TTATGCTTAA GGATACGGAT      780

TCTTTTAAAC TCTCAGGCAT TGACCTATGT AGCTGGACTG ACTAACATCT GAATTTGTTT      840

CTCTGGTTAT ATATGCAATT TTAACTGAAT CGAAATTTCT CTGGATGCTA AAAATGTCTT      900

TAACGGGGTT TATGAGGACT AAATTATCTC CTTCAATGAG GAGGTTCTTG ATTTGCATGT      960

ATGAGCGTGA AAATGCATTC TTAACGGCTA TAGATTCAGT AATAAGTGGT GTTAAAAGTA     1020
```

```
AAAAGTACTT GGAAAAATGA TTAAGCGACT TAATTTTTTT TATTTGTTTG AAAGTTGCCT   1080

TTTCTTGGCT ATCTTAACAT GTATTTATCA AACACCTTTT TTAATTACAT GGAAATCGAA   1140

AAGTTTGAAA AAAAAAAATC ATACTCACTA ACCGCCTTAA AATATAAGCT GAAGATGTCT   1200

CACTAACAGA GTGCATGTGA AGCACCCCCA AAGCAATTAT AACACAACAT CTCCGCCTCT   1260

TCAAAATTCC TACAAATACA TCTAATAAAC TTGTTGAAAC AATCAAAGTA ACATGGTGTG   1320

TCAATTGCGG ATGCTTCTCA TTCCAGACTT TATATAGTGA TTTTGTTTAA TCCATAGTCA   1380

ACAACTCACA TAATGGTACC CAAAGAATAC CCAAATTTTT TGCTCAAAAT CCCTAAACAT   1440

TGTAGCTGTG TAAGTTTGAC TAACATGTTT CAGCATGCTT GCCATGGGTA AATAAGACTT   1500

AGGGGCAAAT CTCGAATCCA CAAACTCATC ATTGGTTTTA GTTTGTCTCC AACGTAAAAC   1560

AATGATGTGA AATACACCAC AAAATTCATA CAATCTCGTT ATCTTGGAAG CTTGAAAGCC   1620

ATAATCTTGT TTGTACTTTC ACTACGTCGA GAAGACAAAA TTACAACTAA GAAGAGGTCA   1680

TTGCTCAGTG TCGTGTACTA CTTATCTTTC AACTCATAGA AACAAGCAAA CCAATTGTCA   1740

CCTATATACT GTACTTCTCC ATCATATACT TCCAACTTGC CTTAAACTCA ATACTATCAT   1800

AAAAACCACA AAGACATTTC ATAAAAGCAT AATAAAAATG TGTCATCACT CTTCAAAGTT   1860

CCAAAGTGAT TCTAACTACA TTCTAATGAA AATGACATTG GTGTAAACCT AATCCTTGTG   1920

TTATAAAACA CCTACATACC ACGATTATGT TAGAAATATA TTTATGAATG CAGTACCTAC   1980

ATAAAGCCAT TAAATAACCA GTTTTATGTT ATTTCGTGAC CAACATAGTT CCTAAAGATT   2040

ACGAAGTAAT TTATAGTCAT TTTGTGGCCA CTTAATTCAT TTAATACCCA GTATATTTAT   2100

AAGTTACCAG CTTAAGTAGT TTTGTGACCA TCTCTACATA CTTCCTCCGG TCCATAATAA   2160

GGGGGCGTTT GGTTGCAACG GGGTAAAGGG AATGGAATCA AGAAAGGGAG AGGAGAGGAA   2220

AGGAAAAGAA AACCCTTAGA TTTAGAGTGG TGTTTGGTTA AGATAATGTT AATTCTCTTT   2280

CTTCCTCTTT CTTACCCTTC TTCCACCCTA GCACCACCAC TCCTCCCTCT GTTACTATTC   2340

TCCACGCCGC CTCTCCCTAC CCCAGTAACA CCACCTTGTC GGCCCCCCGG TCTTCCCCTT   2400

CCCGCGACGG TTCCCCCCTC CCCTGCGCCG TCACGTCGTC CCCCTCACCT CCCTGCACCG   2460

TCGAGTTATC CCCCTCCCCT GCGCGTCGCG TTCTCCCCTC CCTCACCATC GCGTTCTCCC   2520

CTCCCTCACC GTCGCGTTCT CCCCTCCCTC ACCGTCGCGG TCTCCCCTCC CTCACCGTCG   2580

CGGTCTCTCT TTCCCTCCCC CTGCAG                                      2606
```

PROMOTERS FROM PLANT PROTOPORPHYRINOGEN OXIDASE GENES

CROSS-REFERENCE TO RELATED APPLICATIONS

This application claims priority to of U.S. Provisional Application No. 60/012,705, filed Feb. 28, 1996; U.S. Provisional Application No. 60/013,612, filed Feb. 28, 1996; and U.S. Provisional Application No. 60/020,003, filed Jun. 21, 1996.

FIELD OF THE INVENTION

This invention relates to novel DNA sequences that function as promoters of transcription of associated DNA sequences in plants. More specifically, this invention relates to novel promoters that are naturally associated with plant protoporphyrinogen oxidase (protox) coding sequences.

BACKGROUND OF THE INVENTION

I. The Protox Enzyme and its Involvement in the Chlorophyll/Heme Biosynthetic Pathway The biosynthetic pathways that lead to the production of chlorophyll and heme share a number of common steps. Chlorophyll is a light harvesting pigment present in all green photosynthetic organisms. Heme is a cofactor of hemoglobin, cytochromes, P450 mixed-function oxygenases, peroxidases, and catalases (see, e.g. Lehninger, *Biochemistry*. Worth Publishers, New York (1975)), and is therefore a necessary component for all aerobic organisms.

The last common step in chlorophyll and heme biosynthesis is the oxidation of protoporphyrinogen IX to protoporphyrin IX. Protoporphyrinogen oxidase (referred to herein as "protox") is the enzyme that catalyzes this last oxidation step (Matringe et al., *Biochem. J.* 260:231 (1989)).

The protox enzyme has been purified either partially or completely from a number of organisms including the yeast *Saccharomyces cerevisiae* (Labbe-Bois and Labbe, In *Biosynthesis of Heme and Chlorophyll*, E. H. Dailey, ed. McGraw Hill: New York, pp. 235–285 (1990)), barley etioplasts (Jacobs and Jacobs, *Biochem. J.* 244:219 (1987)), and mouse liver (Dailey and Karr, *Biochem.* 26:2697 (1987)). Genes encoding protox have been isolated from two prokaryotic organisms, *Escherichia coli* (Sasarman et al., *Can. J. Microbiol.* 39:1155 (1993)) and *Bacillus subtilis* (Dailey et al., *J. Biol. Chem.* 269:813 (1994)). These genes share no sequence similarity; neither do their predicted protein products share any amino acid sequence identity. The *E. coli* protein is approximately 21 kDa, and associates with the cell membrane. The *B. subtilis* protein is 51 kDa, and is a soluble, cytoplasmic activity.

Protox encoding cDNAs have now also been isolated from humans (see Nishimura et al., *J. Biol. Chem.* 270(14): 8076–8080 (1995) and plants (International application no. PCT/IB95/00452 filed Jun. 8, 1995, published Dec. 21, 1995 as WO 95/34659).

II. The Protox Gene as a Herbicide Target

The use of herbicides to control undesirable vegetation such as weeds or plants in crops has become almost a universal practice. The relevant market exceeds a billion dollars annually. Despite this extensive use, weed control remains a significant and costly problem for farmers.

Effective use of herbicides requires sound management. For instance, time and method of application and stage of weed plant development are critical to getting good weed control with herbicides. Since various weed species are resistant to herbicides, the production of effective herbicides becomes increasingly important.

Unfortunately, herbicides that exhibit greater potency, broader weed spectrum and more rapid degradation in soil can also have greater crop phytotoxicity. One solution applied to this problem has been to develop crops that are resistant or tolerant to herbicides. Crop hybrids or varieties resistant to the herbicides allow for the use of the herbicides without attendant risk of damage to the crop. Development of resistance can allow application of a herbicide to a crop where its use was previously precluded or limited (e.g. to pre-emergence use) due to sensitivity of the crop to the herbicide. For example, U.S. Pat. No. 4,761,373 to Anderson et al. is directed to plants resistant to various imidazolinone or sulfonamide herbicides. The resistance is conferred by an altered acetohydroxyacid synthase (AHAS) enzyme. U.S. Pat. No. 4,975,374 to Goodman et al. relates to plant cells and plants containing a gene encoding a mutant glutamine synthetase (GS) resistant to inhibition by herbicides that were known to inhibit GS, e.g. phosphinothricin and methionine sulfoximine. U.S. Pat. No. 5,013,659 to Bedbrook et al. is directed to plants that express a mutant acetolactate synthase that renders the plants resistant to inhibition by sulfonylurea herbicides. U.S. Pat. No. 5,162,602 to Somers et al. discloses plants tolerant to inhibition by cyclohexanedione and aryloxyphenoxypropanoic acid herbicides. The tolerance is conferred by an altered acetyl coenzyme A carboxylase(ACCase).

The protox enzyme serves as the target for a variety of herbicidal compounds. The herbicides that inhibit protox include many different structural classes of molecules (Duke et al, *Weed Sci.* 39:465 (1991); Nandihalli et al., *Pesticide Biochem. Physiol.* 43:193 (1992); Matringe et al., *FEBS Lett.* 245:35 (1989); Yanase and Andoh, *Pesticide Biochem. Physiol.* 35:70 (1989)). These herbicidal compounds include the diphenylethers {e.g. acifluorfen, 5-[2-chloro-4-(trifluoromethyl)phenoxy]-2-nitrobezoic acid; its methyl ester; or oxyfluorfen, 2-chloro-1-(3-ethoxy-4-nitrophenoxy)-4-(trifluorobenzene)}, oxidiazoles, (e.g. oxidiazon, 3-[2,4-dichloro-5-(1-methylethoxy)phenyl]-5-(1, 1-dimethylethyl)-1,3,4-oxadiazol-2-(3H)-one), cyclic imides (e.g. S-23142, N-(4-chloro-2-fluoro-5-propargyloxyphenyl)-3,4,5,6-tetrahydrophthalimide; chlorophthalim, N-(4-chlorophenyl)-3,4,5,6-tetrahydrophthalimide), phenyl pyrazoles (e.g. TNPP-ethyl, ethyl 2-[1-(2,3,4-trichlorophenyl)-4-nitropyrazolyl-5-oxy] propionate; M&B 39279), pyridine derivatives (e.g. LS 82–556), and phenopylate and its O-phenylpyrrolidino- and piperidinocarbamate analogs. Many of these compounds competitively inhibit the normal reaction catalyzed by the enzyme, apparently acting as substrate analogs.

Typically, the inhibitory effect on protox is determined by measuring fluorescence at about 622 to 635 nM, after excitation at about 395 to 410 nM (see, e.g. Jacobs and Jacobs, *Enzyme* 28:206 (1982); Sherman et al., *Plant Physiol.* 97:280 (1991)). This assay is based on the fact that protoporphyrin IX is a fluorescent pigment, and protoporphyrinogen IX is nonfluorescent.

The predicted mode of action of protox-inhibiting herbicides involves the accumulation of protoporphyrinogen IX in the chloroplast. This accumulation is thought to lead to leakage of protoporphyrinogen IX into the cytosol where it is oxidized by a peroxidase activity to protoporphyrin IX. When exposed to light, protoporphyrin IX can cause formation of singlet oxygen in the cytosol. This singlet oxygen can in turn lead to the formation of other reactive oxygen species, which can cause lipid peroxidation and membrane disruption leading to rapid cell death (Lee et al., *Plant Physiol.* 102:881 (1993)).

Not all protox enzymes are sensitive to herbicides that inhibit plant protox enzymes. Both of the protox enzymes encoded by genes isolated from *Escherichia coli* (Sasarman et al., *Can. J. Microbiol.* 39:1155 (1993)) and *Bacillus subtilis* (Dailey et al., *J. Biol. Chem.* 269:813 (1994)) are resistant to these herbicidal inhibitors. In addition, mutants of the unicellular alga *Chlamydomonas reinhardtii* resistant to the phenylimide herbicide S-23142 have been reported (Kataoka et al., *J. Pesticide Sci.* 15:449 (1990); Shibata et al., In *Research in Photosynthesis,* Vol. III, N. Murata, ed. Kluwer:Netherlands. pp. 567–570 (1992)). At least one of these mutants appears to have an altered protox activity that is resistant not only to the herbicidal inhibitor on which the mutant was selected, but also to other classes of protox inhibitors (Oshio et al., *Z. Naturforsch.* 48c:339 (1993); Sato et al., In *ACS Symposium on Pornphyric Pesticides,* S. Duke, ed. ACS Press:Washington, D.C. (1994)). A mutant tobacco cell line has also been reported that is resistant to the inhibitor S-21432 (Che et al., *Z. Naturforsch.* 48c:350 (1993). In addition, modified, inhibitor-resistant forms of plant protox coding sequences have been described in international application no. PCT/IB95/00452 filed Jun. 8,1995, published Dec. 21, 1995 as WO 95/34659.

III. Regulation of Protox Gene Expression

The bulk of the research related to the protox gene that has been conducted thus far has focused upon the coding sequence and modifications to this enzyme that may render it resistant to protox inhibitors. No information is available in the art with regard to the regulatory elements that control and promote the expression of protox coding sequences in plants.

SUMMARY OF THE INVENTION

The present invention is based on the discovery that the promoter regions naturally associated with the plant protoporphyrinogen oxidase (protox) coding sequences, referred to herein generally as the "protox promoter", are useful for promoting expression of a heterologous coding sequence in a plant.

In accordance with the discovery that the promoter regions naturally associated with the plant protoporphyrinogen oxidase (protox) coding sequence are useful for promoting expression of a heterologous coding sequence in a plant, the present invention provides an isolated DNA molecule comprising a plant protox promoter or a functionally equivalent thereof. The present invention further provides a chimeric gene comprising a plant protox promoter operably linked to a heterologous coding sequence. Plant tissue and plants containing such a chimeric gene are also provided.

In one aspect of the invention the protox promoter is used to express herbicide resistant forms of herbicide target proteins in a plant to confer tolerance to the herbicide. According to this aspect, the protox promoter may be operably linked to a coding sequence for a herbicide-resistant plant protox protein that is resistant to inhibitors of unmodified plant protox protein.

DEPOSITS

The following vector molecules have been deposited with Agricultural Research Service, Patent Culture Collection (NRRL), Northern Regional Research Center, 1815 North University Street, Peoria, Ill. 61604, U.S.A on the dates indicated below:

AraPT1Pro containing the Arabidopsis Protox-1 promoter was deposited Dec. 15, 1995, as pWDC-11 (NRRL #B-21515).

A plasmid containing the maize Protox-1 promoter fused to the remainder of the maize Protox-1 coding sequence was deposited Mar. 19, 1996 as pWDC-14 (NRRL #B21546).

A plasmid containing the Sugar Beet Protox-1 promoter was deposited Dec. 6, 1996, as pWDC-20 (NRRL #B-21650).

DESCRIPTION OF THE SEQUENCE LISTING

SEQ ID NO:1: DNA coding sequence for an *Arabidopsis thaliana* protox-1 protein.

SEQ ID NO:2: Arabidopsis protox-1 amino acid sequence encoded by SEQ ID NO:1.

SEQ ID NO:3: DNA coding sequence for an *Arabidopsis thaliana* protox-2 protein.

SEQ ID NO:4: Arabidopsis protox-2 amino acid sequence encoded by SEQ ID NO:3.

SEQ ID NO:5: DNA coding sequence for a maize protox-1 protein.

SEQ ID NO:6: Maize protox-1 amino acid sequence encoded by SEQ ID NO:5.

SEQ ID NO:7: DNA coding sequence for a maize protox-2 protein.

SEQ ID NO:8: Maize protox-2 amino acid sequence encoded by SEQ ID NO:7.

SEQ ID NO:9: DNA coding sequence for a wheat protox-1 protein.

SEQ ID NO:10: Wheat protox-1 amino acid sequence encoded by SEQ ID NO:9.

SEQ ID NO:11: DNA coding sequence for a soybean protox-1 protein.

SEQ ID NO:12: Soybean protox-1 protein encoded by SEQ ID NO:11.

SEQ ID NO:13: Promoter sequence from *Arabidopsis thaliana* protox-1 gene.

SEQ ID NO:14: Promoter sequence from maize protox-1 gene.

SEQ ID NO:15: DNA coding sequence for a cotton protox-1 protein.

SEQ ID NO:16: Cotton protox-1 amino acid sequence encoded by SEQ ID NO:15.

SEQ ID NO:17: DNA coding sequence for a sugar beet protox-1 protein.

SEQ ID NO:18: Sugar beet protox-1 amino acid sequence encoded by SEQ ID NO:17.

SEQ ID NO:19: DNA coding sequence for a rape protox-1 protein.

SEQ ID NO:20: Rape protox-1 amino acid sequence encoded by SEQ ID NO:19.

SEQ ID NO:21: DNA coding sequence for a rice protox-1 protein.

SEQ ID NO:22: Rice protox-1 amino acid sequence encoded by SEQ ID NO:21.

SEQ ID NO:23: DNA coding sequence for a sorghum protox-1 protein.

SEQ ID NO:24: Sorghum protox-1 amino acid sequence encoded by SEQ ID NO:23.

SEQ ID NO:25: Maize protox-1 intron sequence.

SEQ ID NO:26: Promoter sequence from sugar beet protox-1 gene.

DEFINITIONS

As used herein a "plant protox promoter" is used to refer to the regulatory region that naturally occurs immediately upstream of a protoporphyrinogen oxidase (protox) coding sequence in a plant and is responsible, in its naturally occurring state, for regulating the transcription of the associated protox coding sequence. The plant protox promoter includes the DNA region directly involved in binding of RNA polymerase to initiate transcription and additional upstream regulatory cis-elements that influence the transcription of an operably linked coding sequence.

As used herein a "gene" is used to refer to a DNA molecule that includes (1) a coding sequence and (2) associated regulatory regions that promote and regulate the transcription of the coding sequence in a suitable host cell. The coding sequence may encode a useful transcript (e.g. antisense RNA) or polypeptide produced by translation of the encoded transcript. A gene includes at a minimum, in 5'-3' orientation, a promoter region, a coding sequence and a transcription terminator. A gene may also include additional regulatory regions that can occur as part of the minimal elements (e.g. leaders or signal peptides within the coding sequence) or as discrete elements (e.g. introns).

As used herein a "chimeric gene" refers to a gene that does not naturally occur wherein at least one component part is heterologous with respect to another component part. As used herein to describe the present invention a "chimeric gene" refers to a gene that includes the promoter of the invention operably linked to a heterologous coding sequence.

As used herein with reference to the relationship between a promoter and a coding sequence, the term "heterologous" is used to refer to a relationship that does not naturally occur. For instance, a coding sequence is considered heterologous with respect to a promoter sequence if it is different from the coding sequence that naturally occurs in association with the promoter sequence. This includes modified forms of coding sequences that are naturally associated with a subject promoter. Accordingly, a modified, inhibitor-resistant protox coding sequence is considered to be heterologous with respect to the promoter that is naturally associated with the unmodified, inhibitor-sensitive form of this coding sequence. This further includes the promoter of the invention operably linked to a coding sequence from a different plant or non-plant species.

As used herein, the term "substantial sequence homology" is used to indicate that a nucleotide sequence (in the case of DNA or RNA) or an amino acid sequence (in the case of a protein or polypeptide) exhibits substantial structural and functional equivalence with another nucleotide or amino acid sequence. Any functional or structural differences between sequences having substantial sequence homology will be de minimis; that is they will not affect the ability of the sequence to function as indicated in the present application. For example, a sequence that has substantial sequence homology with a DNA sequence disclosed to be a plant protox promoter will be able to direct the same level and pattern of expression of an associated DNA sequence as the plant protox promoter. Sequences that have substantial sequence homology with the sequences disclosed herein are usually variants of the disclosed sequence, such as mutations, but may also be synthetic sequences. Structural differences are considered de minimis if there is a significant amount of sequence overlap or similarity between two or more different sequences or if the different sequences exhibit similar physical characteristics. Such characteristics can include, for example, immunological reactivity, enzyme activity, structural protein integrity, etc.

Two nucleotide sequences may have substantial sequence homology if the sequences have at least 70 percent, more preferably 80 percent and most preferably 90 percent sequence similarity between them. Two amino acid sequences have substantial sequence homology if they have at least 50 percent, preferably 70 percent, and most preferably 90 percent similarity between the active portions of the polypeptides. In the case of promoter DNA sequences, "substantial sequence homology" also refers to those fragments of a promoter DNA sequence that are able to operate to promote the expression of associated DNA sequences. Such operable fragments of a promoter DNA sequence may be derived from the promoter DNA sequence, for example, by cleaving the promoter DNA sequence using restriction enzymes, synthesizing in accordance with the sequence of the promoter DNA sequence, or may be obtained through the use of PCR technology. Mullis et al., *Meth. Enzymol.*, 155:335–350 (1987); Erlich (ed.), *PCR Technology*, Stockton Press (New York 1989).

A promoter DNA sequence is said to be "operably linked" to a second DNA sequence if the two are situated such that the promoter DNA sequence influences the transcription or translation of the second DNA sequence. For example, if the second DNA sequence codes for the production of a protein, the promoter DNA sequence would be operably linked to the second DNA sequence if the promoter DNA sequence affects the expression of the protein product from the second DNA sequence. For example, in a DNA sequence comprising a promoter DNA sequence physically attached to a coding DNA sequence in the same chimeric construct, the two sequences are likely to be operably linked.

As used herein 'protox-1' refers to a chloroplast protox whereas 'protox-2' refers to a mitochondrial protox.

DETAILED DESCRIPTION OF THE INVENTION

The present invention relates to promoter DNA sequences that are naturally associated with coding sequences for plant protoporphyrinogen oxidase (referred to herein as "protox"; see international application no. PCT/IB95/00452 filed Jun. 8, 1995, published Dec. 21, 1995 as WO 95/34659, incorporated by reference in its entirety; and co-pending U.S. patent application Ser. No. 08/808,931 entitled "DNA Molecules Encoding Plant Protoporphyrinogen Oxidase and Inhibitor Resistant Mutants Thereof" filed on the same day as the instant application and also incorporated by reference in its entirety). These protox promoter sequences have been found to be useful for the expression of a heterologous coding sequence in a plant.

The promoter sequence for the *Arabidopsis thaliana* protox-1 coding sequence (SEQ ID NO:1) is provided as SEQ ID NO:13. Isolation of this promoter from a genomic library using the associated coding sequence as a probe is described in Example 1. The promoter sequence for the maize protox-1 coding sequence (SEQ ID NO:5) is provided as SEQ ID NO:14. Isolation of this promoter from a genomic library using the associated coding sequence as a probe is described in Example 4. The promoter sequence for the sugar beet protox-1 coding sequence (SEQ ID NO:17) is provided as SEQ ID NO:26. Isolation of this promoter from a genomic library using the associated coding sequence as a probe is described in Example 11.

Based on the information provided by the present invention the approach used to isolate the Arabidopsis and maize protox-1 promoters can now be used to isolate the promoter sequence from any plant protox gene. Any protox coding sequence that shares sufficient homology to hybridize to the protox coding sequence associated with the promoter of interest may be used as a probe in this approach. Since the respective protox-1 and protox-2 coding sequences from all plants are contemplated to share this requisite degree of homology, the choice of which protox coding sequence is used as a probe is not considered critical. However, for optimal hybridization results it is preferable to use the most closely related protox coding sequence. Most preferably, the coding sequence used as a probe is from the same plant species as the protox promoter of interest and is the coding sequence naturally associated with the promoter.

The present invention thus relates to an isolated promoter DNA molecule that is naturally associated with coding sequences for plant protoporphyrinogen oxidase. Preferred is an isolated promoter DNA molecule that is naturally associated with coding sequences for plant protoporphyrinogen oxidase from a plant selected from the group consisting of Arabidopsis, sugar cane, soybean, barley, cotton, tobacco, sugar beet, oilseed rape, maize, wheat, sorghum, rye, oats, turf and forage grasses, millet and rice. More preferred is an isolated promoter DNA molecule that is naturally associated with coding sequences for plant protoporphyrinogen oxidase from a plant selected from the group consisting of Arabidopsis, soybean, cotton, tobacco, sugar beet, oilseed rape, maize, wheat, sorghum, rye, oats, turf grass and rice. Particularly preferred is an isolated promoter DNA molecule that is naturally associated with coding sequences for plant protoporphyrinogen oxidase from a plant selected from the group consisting of Arabidopsis, sugar beet and maize. Most preferred is an isolated promoter DNA molecule that is naturally associated with coding sequences for plant protoporphyrinogen oxidase from Arabidopsis. Most preferred is an isolated promoter DNA molecule that is naturally associated with coding sequences for plant protoporphyrinogen oxidase from maize. Most preferred is an isolated promoter DNA molecule that is naturally associated with coding sequences for plant protoporphyrinogen oxidase from sugar beet.

Comprised by the present invention are DNA molecules that hybridize to a DNA molecule according to the invention as defined hereinbefore, but preferably to an oligonucleotide probe obtainable from said DNA molecule comprising a contiguous portion of the sequence of the said protox promoter at least 10 nucleotides in length, under moderately stringent conditions. Most preferred are DNA molecules that hybridize to the nucleotide sequence of either SEQ ID NO:13 (Arabidopsis Protox-1 promoter), SEQ ID NO:14 (maize Protox-1 promoter), or SEQ ID NO:26 (sugar beet Protox-1 promoter) under the following set of conditions:

(a) hybridization in 7% sodium dodecyl sulfate (SDS), 0.5 M NaPO4 pH 7.0, 1 mM EDTA at 50° C.; and (b) wash in 2×SSC, 1% SDS at 50° C.

Factors that effect the stability of hybrids determine the stringency of the hybridization. One such factor is the melting temperature $T_m$, which can be easily calculated according to the formula provided in DNA PROBES, George H. Keller and Mark M. Manak, Macmillan Publishers Ltd, 1993, Section one: Molecular Hybridization Technology; page 8 ff. The preferred hybridization temperature is in the range of about 25° C. below the calculated melting temperature $T_m$ and preferably in the range of about 12–15° C. below the calculated melting temperature $T_m$ and in the case of oligonucleotides in the range of about 5–10° C. below the melting temperature $T_m$.

A further embodiment of the invention is a method of producing a DNA molecule comprising a DNA portion containing a protox promoter sequence and a DNA portion encoding a protox protein comprising (a) preparing a nucleotide probe capable of specifically hybridizing to a plant protox gene or mRNA, wherein said probe comprises a contiguous portion of the coding sequence for a protox protein or the protox promoter sequence from a plant of at least 10 nucleotides length;

(b) probing for other protox coding sequences in populations of cloned genomic DNA fragments or cDNA fragments from a chosen organism using the nucleotide probe prepared according to step (a); and (c) isolating and multiplying a DNA molecule comprising a DNA portion containing a protox promoter sequence and a DNA portion encoding a protox protein.

A further embodiment of the invention is a method of producing a DNA molecule comprising a DNA portion containing a protox promoter sequence comprising (a) preparing a nucleotide probe capable of specifically hybridizing to a plant protox gene or mRNA, wherein said probe comprises a contiguous portion of the coding sequence for a protox protein from a plant of at least 10 nucleotides length;

(b) probing for other protox coding sequences or protox promoter sequences in populations of cloned genomic DNA fragments or cDNA fragments from a chosen organism using the nucleotide probe prepared according to step (a); and (c) isolating and multiplying a DNA molecule comprising a DNA portion containing a protox promoter sequence.

A further embodiment of the invention is a method of isolating a DNA molecule comprising a DNA portion containing a protox promoter sequence from any plant protox gene comprising (a) preparing a nucleotide probe capable of specifically hybridizing to a plant protox gene or mRNA, wherein said probe comprises a contiguous portion of the coding sequence for a protox protein or the protox promoter sequence from a plant of at least 10 nucleotides length;

(b) probing for other protox coding sequences or protox promoter sequences in populations of cloned genomic DNA fragments or cDNA fragments from a chosen organism using the nucleotide probe prepared according to step (a); and (c) isolating a DNA molecule comprising a DNA portion containing a protox promoter sequence.

The invention further embodies the use of a nucleotide probe capable of specifically hybridizing to a plant protox gene or mRNA of at least 10 nucleotides length in a polymerase chain reaction (PCR), wherein the said probe can either be obtained from the coding region or the promoter region of the protox gene.

The invention further embodies the use of a nucleotide probe capable of specifically hybridizing to a plant protox gene or to map the location of the protox gene(s) in the genome of a chosen plant using standard techniques based on the selective hybridization of the probe to genomic protox sequences.

The invention embodies the use of a protox coding sequence that shares sufficient homology to hybridize to the protox coding sequence associated with the promoter of interest as a probe. Preferred is the use of a protox coding sequence wherein the coding sequence used as a probe is from the same plant species as the protox promoter of interest and is the coding sequence naturally associated with the promoter.

The plant protox promoter of the present invention includes the Arabidopsis protox-1 promoter sequence set forth in SEQ ID NO:13, the *Zea mays* (maize) protox-1 promoter sequence set forth in SEQ ID NO:14, the sugar beet protox-1 promoter sequence set forth in SEQ ID NO:26 as well as corresponding protox-1 promoter sequences available from other plant species as indicated above. The present invention also includes functional fragments of these DNA sequences that retain the ability to regulate expression of an operably linked coding sequence in the same manner as the exemplified protox promoter sequence. Such functional fragments may be identified through deletion analyses or other standard techniques used in the art to identify protox promoter activity (see, e.g. pages 546–549 of "Genes IV", ed. by Lewin, Oxford Univ. Press (1990)). The present invention also includes DNA sequences having substantial sequence homology with the protox promoters available from plant genes that confer an equivalent level and pattern of expression upon an operably linked sequence. Such promoter sequences may be obtained through modification of the protox promoters isolated from plant genes and are considered functionally equivalent derivatives of the plant protox promoters.

As illustrated in the examples below, the DNA sequences, vectors and transgenic plants of the present invention comprise a promoter sequence derived from a plant protox gene. The protox promoter DNA sequences are preferably linked operably to a coding DNA sequence, for example a DNA sequence that is transcribed into a useful RNA transcript such as an antisense transcript, or a coding sequence that is ultimately expressed in the production of a useful protein product.

In a preferred embodiment, the protox promoter is used to direct the expression of a modified herbicide target enzyme that is resistant to herbicides at levels that inhibit the corresponding unmodified version of the enzyme. The invention thus relates to the use of a protox promoter to express herbicide resistant forms of herbicide target proteins in a plant to confer tolerance to the herbicide. Such modified herbicide-resistant enzymes include herbicide-resistant forms of imidazoleglycerol phosphate dehydratase (IGPD; see WO 9426909 published Nov. 24, 1994), EPSP synthase (see U.S. Pat. Nos. 4,535,060; 4,769,061; 4,940,835 and EP 550,633), glutamine synthetase (GS; see U.S. Pat. No. 4,975,374), acetyl coenzyme A carboxylase(ACCase; see U.S. Pat. No. 5,162,602), and acetolactate synthase (see U.S. Pat. Nos. 4,761,373; 5,304,732; 5,331,107; 5,013,659; 5,141,870; and 5,378,824). In a most preferred embodiment, the protox promoter is used to direct the expression of a modified protox enzyme that is resistant to protox inhibitors as illustrated in Examples 2–3 (see also International application no. PCT/IB95/00452 filed Jun. 8, 1995, published Dec. 21, 1995 as WO 95/34659 whose relevant parts are herein incorporated by reference; see also co-pending application entitled "DNA Molecules Encoding Plant Protoporphyrinogen Oxidase and Inhibitor Resistant Mutants Thereof" filed on the same day as the instant application).

The invention relates to a chimeric gene that comprises an expression cassette comprising a plant protox promoter operably linked to a heterologous DNA coding sequence. Preferred is a chimeric gene wherein said plant protox promoter is from a protox-1 gene or protox-2 gene. Particularly preferred is a chimeric gene wherein said plant protox promoter is from a protox-1 gene. Particularly preferred is a chimeric gene wherein said plant protox promoter is from a protox-2 gene.

Preferred is a chimeric gene wherein said plant protox promoter is from a plant selected from the group consisting of Arabidopsis, sugar cane, soybean, barley, cotton, tobacco, sugar beet, oilseed rape, maize, wheat, sorghum, rye, oats, turf and forage grasses, millet and rice. More preferred is a chimeric gene wherein said plant protox promoter is from a plant selected from the group consisting of Arabidopsis, soybean, cotton, tobacco, sugar beet, oilseed rape, maize, wheat, sorghum, rye, oats, turf grass and rice. Particularly preferred is a chimeric gene wherein said plant protox promoter is from a plant selected from the group consisting of Arabidopsis, maize and sugar beet. More preferred is a chimeric gene wherein said plant protox promoter is from a plant selected from the group consisting of Arabidopsis and maize. Most preferred is a chimeric gene wherein said plant protox promoter has the sequence set forth in SEQ ID NO:13. Most preferred is a chimeric gene wherein said plant protox promoter has the sequence set forth in SEQ ID NO:14. Most preferred is a chimeric gene wherein said plant protox promoter has the sequence set forth in SEQ ID NO:26. Preferred is a chimeric gene wherein said plant protox promoter is at least 500 nucleotides, more preferably at least 300 nucleotides in length.

Preferred is a chimeric gene, wherein the DNA molecule encodes a protein from an Arabidopsis species having protox-1 activity or protox-2 activity, preferably wherein said protein comprises the amino acid sequence set forth in SEQ ID NO:2 or SEQ ID NO:4. Also preferred is a chimeric gene, wherein the DNA molecule encodes a protein from maize having protox-1 activity or protox-2 activity, preferably wherein said protein comprises the amino acid sequence set forth in set forth in SEQ ID NO:6 or SEQ ID NO:8. Also preferred is a chimeric gene, wherein the DNA molecule encodes a protein from wheat having protox-1 activity, preferably wherein said protein comprises the amino acid sequence set forth in SEQ ID NO:10. Also preferred is a chimeric gene, wherein the DNA molecule encodes a protein from soybean having protox-1 activity, preferably wherein said protein comprises the amino acid sequence set forth in SEQ ID NO:12. Also preferred is a chimeric gene, wherein the DNA molecule encodes a protein from cotton having protox-1 activity, preferably wherein said protein comprises the amino acid sequence set forth in SEQ ID NO:16. Also preferred is a chimeric gene, wherein the DNA molecule encodes a protein from sugar beet having protox-1 activity, preferably wherein said protein comprises the amino acid sequence set forth in SEQ ID NO:18. Also preferred is a chimeric gene, wherein the DNA molecule encodes a protein from rape having protox-1 activity, preferably wherein said protein comprises the amino acid sequence set forth in SEQ ID NO:20. Also preferred is a chimeric gene, wherein the DNA molecule encodes a protein from rice having protox-1 activity, preferably wherein said protein comprises the amino acid sequence set forth in SEQ ID NO:22. Also preferred is a chimeric gene, wherein the DNA molecule encodes a protein from sorghum having protox-1 activity, preferably wherein said protein comprises the amino acid sequence set forth in SEQ ID NO:24.

The invention further relates to a chimeric gene that comprises an expression cassette comprising a plant protox promoter operably linked to the DNA molecule encoding a protein from a plant, that is resistant to herbicides at levels that inhibit the corresponding unmodified version of the enzyme.

Preferred is a chimeric gene, wherein said heterologous coding sequence encodes a modified, herbicide-resistant form of a plant enzyme. Especially preferred is a chimeric gene wherein said plant enzyme is selected from the group consisting of imidazoleglycerol phosphate dehyratase (IGPD), 5-enolpyruvylshikimate-3-phosphate synthase (EPSP), glutamine synthetase (GS), acetyl coenzyme A carboxylase, acetolactate synthase, histidinol dehydrogenase and protoporphyrinogen oxidase (protox). More preferred is a chimeric gene wherein said plant enzyme is selected from the group consisting of imidazoleglycerol phosphate dehyratase (IGPD), 5-enolpyruvylshikimate-3-phosphate synthase (EPSP), glutamine synthetase (GS), acetyl coenzyme A carboxylase, acetolactate synthase and protoporphyrinogen oxidase (protox).

Particularly preferred is a chimeric gene wherein said plant enzyme is a eukaryotic protox. More preferred is a chimeric gene wherein said plant enzyme is a eukaryotic protox having a amino acid substitution, said amino acid substitution having the property of conferring resistance to a protox inhibitor. Most preferred is a chimeric gene wherein said plant enzyme is a eukaryotic protox according to the copending International application No. . . . entitled "DNA Molecules Encoding Plant Protoporphyrinogen Oxidase and Inhibitor Resistant Mutants Thereof", having the property of conferring resistance to a protox inhibitor.

Preferred is a chimeric gene, wherein the DNA molecule encodes a protein from a plant that is selected from the group consisting of which is selected from the group consisting of Arabidopsis, sugar cane, soybean, barley, cotton, tobacco, sugar beet, oilseed rape, maize, wheat, sorghum, rye, oats, turf and forage grasses, millet, forage and rice. More preferred is a chimeric gene, wherein the DNA molecule encodes a protein from a plant that is selected from the group consisting of Arabidopsis, soybean, cotton, sugar beet, oilseed rape, maize, wheat, sorghum. Particularly preferred is a chimeric gene, wherein the DNA molecule a protein from a plant that is selected from the group consisting of Arabidopsis, wheat, soybean and maize. Most preferred is a chimeric gene, wherein the DNA molecule encodes a protein from a plant that is selected from the group consisting of soybean and wheat.

The invention further relates to the use of chimeric gene according to the invention to express a herbicide resistant plant protox protein that is resistant to inhibitors of unmodified plant protox protein. The invention relates further to the stable integration of said chimeric gene into a host genome. The invention relates to a recombinant DNA molecule comprising a plant protoporphyrinogen oxidase (protox) promoter or a functionally equivalent derivative thereof. The invention further relates to a recombinant DNA vector comprising said recombinant DNA molecule.

A further object of the invention is a recombinant vector comprising the said chimeric gene wherein said vector is capable of being stably transformed into a plant, plant seeds, plant tissue or plant cell. The plant and progeny thereof, plant seeds, plant tissue or plant cell stably transformed with the vector is capable of expressing the DNA molecule encoding a desired protein, which may be from a non-plant or plant source, preferably from a plant. Preferred is a recombinant vector, wherein the plant and progeny thereof, plant seeds, plant tissue or plant cell stably transformed with the said vector is capable of expressing the DNA molecule encoding a desired protein, which may be from a non-plant or plant source, preferably from a plant that is resistant to herbicides at levels that inhibit the corresponding unmodified version of the enzyme.

The present invention is further directed to transgenic plant tissue, including plants, and the descendants thereof, seeds, and cultured tissue, stably transformed with at least one chimeric gene according to the invention. Preferred is transgenic plant tissue, including plants, seeds, and cultured tissue, stably transformed with at least one chimeric gene that comprises an expression cassette comprising a plant protox promoter operably linked to a DNA coding sequence capable of expressing a protein, which may be from a non-plant or plant source, preferably from a plant, which is resistant to herbicides at levels that inhibit the corresponding unmodified version of the enzyme in the plant tissue.

Also encompassed by the present invention is a host cell stably transformed with the vector according to the invention, wherein said host cell is capable of expressing said DNA molecule. Preferred is a host cell selected from the group consisting of a plant cell, a bacterial cell, a yeast cell, and an insect cell.

The present invention is further directed to plants and the progeny thereof, plant tissue and plant seeds tolerant to herbicides that inhibit the naturally occurring protox activity in these plants, wherein the tolerance is conferred by a gene expressing a modified inhibitor-resistant protox enzyme as taught herein. Representative plants include any plants to which these herbicides may be applied for their normally intended purpose. Preferred are agronomically important crops, i.e., angiosperms and gymnosperms such as Arabidopsis, soybean, sugar cane, barley, cotton, tobacco, sugar beet, oilseed rape, maize, wheat, sorghum, rye, oats, turf and forage grasses, millet and rice and the like. More preferred are agronomically important crops, i.e., angiosperms and gymnosperms such as Arabidopsis, cotton, soybean, rape, sugar beet, tobacco, maize, rice, wheat, oats, rye, sorghum, turf grass. Particularly preferred are agronomically important crops, i.e., angiosperms and gymnosperms such as Arabidopsis, soybean, cotton, sugar beet, oilseed rape, maize, wheat, sorghum, and rice.

The transgenic plants of the present invention may be transformed by any method of transformation known in the art. These methods include, for instance, transformation by direct infection or co-cultivation of plants, plant tissue or cells with *Agrobacterium tumefaciens;* Horsch et al., *Science,* 225:1229 (1985); Marton, "Cell Culture and Somatic Cell Genetic of Plants", vol. 1, pp. 514–521 (1984); direct gene transfer into protoplasts; Paszkowski et al., *EMBO J.* 12:2717 (1984); Loerz et al., *Mol. Gen. & Genet.* 1199:178 (1985); Fromm et al., *Nature* 319:719 (1986); microprojectile bombardment, Klein et al., *Bio/Technology,* 6:559–563 (1988); injection into protoplasts cultured cells and tissues, Reich et al., *Bio/Technology,* 4:1001–1004 (1986); or injection into meristematic tissues of seedlings and plants as described by De La Pena et al., *Nature,* 325:274–276 (1987); Hooykaas-Van Slogteren et al., *Nature,* 311:763–764 (1984); Grimsley et al., *Bio/Technology,* 6:185 (1988); and Grimsley et al., *Nature,* 325:177 (1988).

The genetic properties engineered into the transgenic seeds and plants described above are passed on by sexual reproduction or vegetative growth and can thus be maintained and propagated in progeny plants. Generally said maintenance and propagation make use of known agricultural methods developed to fit specific purposes such as tilling, sowing or harvesting. Specialized processes such as hydroponics or greenhouse technologies can also be applied. As the growing crop is vulnerable to attack and damages caused by insects or infections as well as to competition by weed plants, measures are undertaken to control weeds, plant diseases, insects, nematodes, and other adverse conditions to improve yield. These include mechanical measures such a tillage of the soil or removal of weeds and infected plants, as well as the application of agrochemicals such as herbicides, fungicides, gametocides, nematicides, growth regulants, ripening agents and insecticides.

Use of the advantageous genetic properties of the transgenic plants and seeds according to the invention can further be made in plant breeding that aims at the development of plants with improved properties such as tolerance of pests, herbicides, or stress, improved nutritional value, increased yield, or improved structure causing less loss from lodging or shattering. The various breeding steps are characterized by well-defined human intervention such as selecting the lines to be crossed, directing pollination of the parental lines, or selecting appropriate progeny plants. Depending on the desired properties different breeding measures are taken. The relevant techniques are well known in the art and include but are not limited to hybridization, inbreeding, backcross breeding, multiline breeding, variety blend, interspecific hybridization, aneuploid techniques, etc. Hybridization techniques also include the sterilization of plants to yield male or female sterile plants by mechanical, chemical or biochemical means. Cross pollination of a male sterile plant with pollen of a different line assures that the genome of the male sterile but female fertile plant will uniformly obtain properties of both parental lines. Thus, the transgenic seeds and plants according to the invention can be used for the breeding of improved plant lines that for example increase the effectiveness of conventional methods such as herbicide or pesticide treatment or allow to dispense with said methods due to their modified genetic properties. Alternatively new crops with improved stress tolerance can be obtained that, due to their optimized genetic "equipment", yield harvested product of better quality than products that were not able to tolerate comparable adverse developmental conditions.

In seeds production germination quality and uniformity of seeds are essential product characteristics, whereas germination quality and uniformity of seeds harvested and sold by the farmer is not important. As it is difficult to keep a crop free from other crop and weed seeds, to control seedborne diseases, and to produce seed with good germination, fairly extensive and well-defined seed production practices have been developed by seed producers, who are experienced in the art of growing, conditioning and marketing of pure seed. Thus, it is common practice for the farmer to buy certified seed meeting specific quality standards instead of using seed harvested from his own crop. Propagation material to be used as seeds is customarily treated with a protectant coating comprising herbicides, insecticides, fungicides, bactericides, nematicides, molluscicides or mixtures thereof. Customarily used protectant coatings comprise compounds such as captan, carboxin, thiram (TMTD®), methalaxyl (Apron®), and pirimiphos-methyl (Actellic®). If desired these compounds are formulated together with further carriers, surfactants or application-promoting adjuvants customarily employed in the art of formulation to provide protection against damage caused by bacterial, fungal or animal pests. The protectant coatings may be applied by impregnating propagation material with a liquid formulation or by coating with a combined wet or dry formulation. Other methods of application are also possible such as treatment directed at the buds or the fruit.

It is a further aspect of the present invention to provide new agricultural methods such as the methods exemplified above, which are characterized by the use of transgenic plants, transgenic plant material, or transgenic seed according to the present invention. The invention is directed to an agricultural method, wherein a transgenic plant or the progeny thereof is used comprising a chimeric gene according to the invention in an amount sufficient to express herbicide resistant forms of herbicide target proteins in a plant to confer tolerance to the herbicide.

To breed progeny from plants transformed according to the method of the present invention, a method such as that which follows may be used: maize plants produced as described in the examples set forth below are grown in pots in a greenhouse or in soil, as is known in the art, and permitted to flower. Pollen is obtained from the mature tassel and used to pollinate the ears of the same plant, sibling plants, or any desirable maize plant. Similarly, the ear developing on the transformed plant may be pollinated by pollen obtained from the same plant, sibling plants, or any desirable maize plant. Transformed progeny obtained by this method may be distinguished from non-transformed progeny by the presence of the introduced gene(s) and/or accompanying DNA (genotype), or the phenotype conferred. The transformed progeny may similarly be selfed or crossed to other plants, as is normally done with any plant carrying a desirable trait. Similarly, tobacco or other transformed plants produced by this method may be selfed or crossed as is known in the art in order to produce progeny with desired characteristics. Similarly, other transgenic organisms produced by a combination of the methods known in the art and this invention may be bred as is known in the art in order to produce progeny with desired characteristics.

The invention is illustrated in more detail by the following examples, without implying any restriction to what is described therein.

EXAMPLES

Example 1

Isolation of the *Arabidopsis thaliana* Protox-1 Promoter Sequence

A Lambda Zap II genomic DNA library prepared from *Arabidopsis thaliana* (Columbia, whole plant) was purchased from Stratagene. Approximately 125,000 phage were plated at a density of 25,000 pfu (plaque forming units) per 15 cm Petri dish and duplicate lifts were made onto Colony/Plaque Screen membranes (NEN Dupont). The plaque lifts were probed with the Arabidopsis Protox-1 cDNA (SEQ ID NO:1 labeled with 32P-dCTP by the random priming method (Life Technologies). Hybridization and wash conditions were at 65° C. as described in Church and Gilbert, Proc. Natl. Acad. Sci. USA 81:1991–1995 (1984). Positively hybridizing plaques were purified and in vivo excised into pBluescript plasmids. Sequence from the genomic DNA inserts was determined by the chain termination method using dideoxy terminators labeled with fluorescent dyes (Applied Biosystems, Inc.). One clone, AraPT1Pro, was determined to contain 580 bp of Arabidopsis sequence upstream from the initiating methionine (ATG) of the Protox-1 protein coding sequence. This clone also contains coding sequence and introns that extend to bp 1241 of the Protox-1 cDNA sequence. The 580 bp 5' noncoding fragment is the putative Arabidopsis Protox-1 promoter, and the sequence is set forth in SEQ ID NO:13.

AraPT1Pro was deposited Dec. 4, 1995, as pWDC-11 (NRRL #B-21515).

Example 2

Construction of Plant Transformation Vectors Expressing Altered Protox-1 Genes Behind the Native Arabidopsis Protox-1 Promoter A full-length cDNA of the appropriate altered Arabidopsis Protox-1 cDNA is isolated as an EcoRI-XhoI partial digest fragment and cloned into the plant expression vector pCGN1761ENX (see Example 9 of International application no. PCT/IB95/00452 filed Jun. 8, 1995, published Dec. 21, 1995 as WO 95/34659). This plasmid is digested with NcoI and BamHI to produce a fragment comprised of the complete Protox-1 cDNA plus a transcription terminator from the 3' untranslated sequence of the tml gene of *Agrobacterium tumefaciens*. The AraPT1Pro plasmid described above is digested with NcoI and BamHI to produce a fragment comprised of pBluescript and the 580 bp putative Arabidopsis Protox-1 promoter. Ligation of these two fragments produces a fusion of the altered protox cDNA to the native protox promoter. The expression cassette containing the Protox-1 promoter/Protox-1 cDNA/tml terminator fusion is excised by digestion with KpnI and cloned into the binary vector pCIB200. The binary plasmid is transformed by electroporation into Agrobacterium and then into Arabidopsis using the vacuum infiltration method (Bechtold et al. C.R. Acad. Sci. Paris 316:1194–1199 (1993)). Transformants expressing altered protox genes are selected on kanamycin or on various concentrations of protox inhibiting herbicide.

Example 3
Production of Herbicide Tolerant Plants by Expression of a Native Protox-1 Promoter/Altered Protox-1 Fusion Using the procedure described above, an Arabidopsis Protox-1 cDNA containing a TAC to ATG (Tyrosine to Methionine) change at nucleotides 1306–1308 the Protox-1 sequence (SEQ ID NO:1) was fused to the native Protox-1 promoter fragment and transformed into *Arabidopsis thaliana*. This altered Protox-1 enzyme (AraC-2Met) has been shown to be >10-fold more tolerant to various protox-inhibiting herbicides than the naturally occurring enzyme when tested in a bacterial expression system (see copending International application entitled "DNA Molecules Encoding Plant Protoporphyrinogen Oxidase and Inhibitor Resistant Mutants Thereof" (docket number PH/5-20757/P1/CGC1847) filed on the same day as the instant application). Seed from the vacuum infiltrated plants was collected and plated on a range (10.0 nM–1.0 uM) of a protox inhibitory aryluracil herbicide of formula XVII. Multiple experiments with wild type Arabidopsis have shown that a 10.0 nM concentration of this compound is sufficient to prevent normal seedling germination. Transgenic seeds expressing the AraC-2Met altered enzyme fused to the native Protox-1 promoter produced normal Arabidopsis seedlings at herbicide concentrations up to 500 nM, indicating at least 50-fold higher herbicide tolerance when compared to wild-type Arabidopsis. This promoter/altered protox enzyme fusion therefore functions as an effective selectable marker for plant transformation. Several of the plants that germinated on 100.0 nM of protox-inhibiting herbicide were transplanted to soil, grown 2–3 weeks, and tested in a spray assay with various concentrations of the protox-inhibiting herbicide. When compared to empty vector control transformants, the AraPT1Pro/AraC-2Met transgenics were >10-fold more tolerant to the herbicide spray.

Example 4
Isolation of a Maize Protox-1 Promoter Sequence

A *Zea Mays* (Missouri 17 inbred, etiolated seedlings) genomic DNA library in the Lambda FIX II vector was purchased from Stratagene. Approximately 250,000 pfu of the library was plated at a density of 50,000 phage per 15 cm plate and duplicate lifts were made onto Colony/Plaque screen membranes (NEN Dupont).The plaque lifts were probed with the maize Protox-1 cDNA (SEQ ID NO:5) labeled with 32P-dCTP by the random priming method (Life Technologies). Hybridization and wash conditions were at 65° C. as described in Church and Gilbert, Proc. Natl. Acad. Sci. USA 81:1991–1995 (1984). Lambda phage DNA was isolated from three positively hybridizing phage using the Wizard Lambda Preps DNA Purification System (Promega). Analysis by restriction digest, hybridization patterns, and DNA sequence analysis identified a lambda clone containing approximately 3.5 kb of maize genomic DNA located 5' to the maize Protox-1 coding sequence previously isolated as a cDNA clone. This fragment is contemplated to include the maize Protox-1 promoter. The sequence of this fragment is set forth in SEQ ID NO:14. From nucleotide 1 to 3532, this sequence is comprised of 5' noncoding sequence. From nucleotide 3533 to 3848, this sequence encodes the 5' end of the maize Protox-1 protein.

A plasmid containing the sequence of SEQ ID NO:14 fused to the remainder of the maize Protox-1 coding sequence was deposited Mar. 19, 1996 as pWDC-14 (NRRL #B21546).

Example 5
Construction of Plant Transformation Vectors

Numerous transformation vectors are available for plant transformation, and the promoters and chimeric genes of this invention can be used in conjunction with any such vectors. The selection of vector for use will depend upon the preferred transformation technique and the target species for transformation. For certain target species, different antibiotic or herbicide selection markers may be preferred. Selection markers used routinely in transformation include the nptII gene, which confers resistance to kanamycin and related antibiotics (Messing & Vierra, *Gene* 19:259–268 (1982); Bevan et al., *Nature* 304:184–187 (1983)), the bar gene, which confers resistance to the herbicide phosphinothricin (White et al., *Nucl Acids Res* 18:1062 (1990), Spencer et al. *Theor Appl Genet* 79:625–631(1990)), the hph gene, which confers resistance to the antibiotic hygromycin (Blochinger & Diggelmann, *Mol Cell Biol* 4:2929–2931), and the dhfr gene, which confers resistance to methotrexate (Bourouis et al., *EMBO J.* 2(7):1099–1104 (1983)).

I. Construction of Vectors Suitable for Agrobacterium Transformation

Many vectors are available for transformation using *Agrobacterium tumefaciens*. These typically carry at least one T-DNA border sequence and include vectors such as pBIN19 (Bevan, *Nucl. Acids Res.* (1984)) and pXYZ. Below the construction of two typical vectors is described.

Construction of pCIB200 and pCIB2001: The binary vectors pCIB200 and pCIB2001 are used for the construction of recombinant vectors for use with Agrobacterium and was constructed in the following manner. pTJS75kan was created by NarI digestion of pTJS75 (Schmidhauser & Helinski, *J Bacteriol.* 164:446–455 (1985)) allowing excision of the tetracycline-resistance gene, followed by insertion of an AccI fragment from pUC4K carrying an NPTII (Messing & Vierra, *Gene* 19:259–268 (1982); Bevan et al., *Nature* 304:184–187 (1983); McBride et al., *Plant Molecular Biology* 14:266–276 (1990)). XhoI linkers were ligated to the EcoRV fragment of pCIB7, which contains the left and right T-DNA borders, a plant selectable nos/nptII chimeric gene and the pUC polylinker (Rothstein et al., *Gene* 53:153–161 (1987)), and the XhoI-digested fragment was cloned into SalI-digested pTJS75kan to create pCIB200 (see also EP 0 332 104, example 19 [1338]). pCIB200 contains the following unique polylinker restriction sites: EcoRI, SstI, KpnI, BglII, XbaI, and SalI. pCIB2001 is a derivative of pCIB200, which was created by the insertion into the polylinker of additional restriction sites. Unique restriction sites in the polylinker of pCIB2001 are EcoRI, SstI, KpnI, BglII, XbaI, SalI, MluI, BclI, AvrII, ApaI, HpaI, and StuI. pCIB2001, in addition to containing these unique restriction sites also has plant and bacterial kanamycin selection, left and right T-DNA borders for Agrobacterium-mediated transformation, the RK2-derived trfA function for mobilization between *E. coli* and other hosts, and the OriT and OriV functions also from RK2. The pCIB2001 polylinker is suitable for the cloning of plant expression cassettes containing their own regulatory signals.

Construction of pCIB10 and Hygromycin Selection Derivatives thereof: The binary vector pCIB10 contains a gene encoding kanamycin resistance for selection in plants, T-DNA right and left border sequences and incorporates sequences from the wide host-range plasmid pRK252 allowing it to replicate in both *E. coli* and Agrobacterium. Its construction is described by Rothstein et al., *Gene* 53:153–161 (1987). Various derivatives of pCIB10 have been constructed that incorporate the gene for hygromycin B phosphotransferase described by Gritz et al., *Gene* 25:179–188 (1983)). These derivatives enable selection of transgenic plant cells on hygromycin only (pCIB743), or hygromycin and kanamycin (pCIB715, pCIB717).

II. Construction of Vectors Suitable for non-Agrobacterium Transformation

Transformation without the use of *Agrobacterium tumefaciens* circumvents the requirement for T-DNA sequences in the chosen transformation vector and consequently vectors lacking these sequences can be utilized in addition to vectors such as the ones described above that contain T-DNA sequences. Transformation techniques that do not rely on Agrobacterium include transformation via particle bombardment, protoplast uptake (e.g. PEG and electroporation) and microinjection. The choice of vector depends largely on the preferred selection for the species being transformed. Below, the construction of some typical vectors is described.

Construction of pCIB3064: pCIB3064 is a pUC-derived vector suitable for direct gene transfer techniques in combination with selection by the herbicide basta (or phosphinothricin). The plasmid pCIB246 comprises the CaMV 35S promoter in operational fusion to the *E. coli* GUS gene and the CaMV 35S transcriptional terminator and is described in the PCT published application WO 93/07278. The 35S promoter of this vector contains two ATG sequences 5' of the start site. These sites were mutated using standard PCR techniques in such a way as to remove the ATG's and generate the restriction sites SspI and PvuII. The new restriction sites were 96 and 37 bp away from the unique SalI site and 101 and 42 bp away from the actual start site. The resultant derivative of pCIB246 was designated pCIB3025. The GUS gene was then excised from pCIB3025 by digestion with SalI and SacI, the termini rendered blunt and religated to generate plasmid pCIB3060. The plasmid pJIT82 was obtained from the John Innes Centre, Norwich and the 400 bp SmaI fragment containing the bar gene from *Streptomyces viridochromogenes* was excised and inserted into the HpaI site of pCIB3060 (Thompson et al. *EMBO J* 6:2519–2523 (1987)). This generated pCIB3064, which comprises the bar gene under the control of the CaMV 35S promoter and terminator for herbicide selection, a gene for ampicillin resistance (for selection in *E coli*) and a polylinker with the unique sites SphI, PstI, HindIII, and BamHI. This vector is suitable for the cloning of plant expression cassettes containing their own regulatory signals.

Construction of pSOG19 and pSOG35: pSOG35 is a transformation vector that utilizes the *E. coli* gene dihydrofolate reductase (DHFR) as a selectable marker conferring resistance to methotrexate. PCR was used to amplify the 35S promoter (~800 bp), intron 6 from the maize Adh1 gene (~550 bp) and 18 bp of the GUS untranslated leader sequence from pSOG10. A 250 bp fragment encoding the *E. coli* dihydrofolate reductase type II gene was also amplified by PCR and these two PCR fragments were assembled with a SacI-PstI fragment from pBI221 (Clontech), which comprised the pUC19 vector backbone and the nopaline synthase terminator. Assembly of these fragments generated pSOG19, which contains the 35S promoter in fusion with the intron 6 sequence, the GUS leader, the DHFR gene and the nopaline synthase terminator. Replacement of the GUS leader in pSOG19 with the leader sequence from Maize Chlorotic Mottle Virus (MCMV) generated the vector pSOG35. pSOG19 and pSOG35 carry the pUC gene for ampicillin resistance and have HindIII, SphI, PstI and EcoRI sites available for the cloning of foreign sequences such as chimeric gene sequences containing a plant protox promoter.

Example 6
Construction of Chimeric Genes/Plant Expression Cassettes

Coding sequences intended for expression in transgenic plants under the control of a plant protox promoter may be assembled in expression cassettes behind a suitable protox promoter and upstream of a suitable transcription terminator. The resulting chimeric genes can then be easily transferred to the plant transformation vectors described above in Example 5.

I. Protox Promoter Selection

In accordance with the present invention, the chimeric gene will contain a plant protox promoter. The selection of the specific protox promoter used in the chimeric gene is primarily up to the individual researcher, although generally it will be preferable to use a protox promoter from a plant species closely related to, or most preferably identical, to the species intended to contain the resulting chimeric gene. For example, if the chimeric gene is intended to be contained in a maize plant it would be preferable to use a protox promoter from a monocotyledonous plant and most preferable to use a maize protox promoter.

II. Transcriptional Terminators

A variety of transcriptional terminators are available for use in expression cassettes. These are responsible for the termination of transcription beyond the transgene and its correct polyadenylation. Appropriate transcriptional terminators are those that are known to function in plants and include the CaMV 35S terminator, the tml terminator, the nopaline synthase terminator, the pea rbcS E9 terminator, as well as terminators naturally associated with the plant protox gene (i.e. "protox terminators"). These can be used in both monocotyledons and dicotyledons.

III. Sequences for the Enhancement or Regulation of Expression

Numerous sequences have been found to enhance gene expression from within the transcriptional unit and these sequences can be used in conjunction with the genes of this invention to increase their expression in transgenic plants.

Various intron sequences have been shown to enhance expression, particularly in monocotyledonous cells. For example, the introns of the maize Adh1 gene have been found to significantly enhance the expression of the wild-type gene under its cognate promoter when introduced into maize cells. Intron 1 was found to be particularly effective and enhanced expression in fusion constructs with the chloramphenicol acetyltransferase gene (Callis et al., *Genes Develop.* 1:1183–1200 (1987)). In the same experimental system, the intron from the maize bronze1 gene had a similar effect in enhancing expression (Callis et al., supra). Intron sequences have been routinely incorporated into plant transformation vectors, typically within the non-translated leader.

A number of non-translated leader sequences derived from viruses are also known to enhance expression, and these are particularly effective in dicotyledonous cells. Specifically, leader sequences from Tobacco Mosaic Virus (TMV, the "W-sequence"), Maize Chlorotic Mottle Virus (MCMV), and Alfalfa Mosaic Virus (AMV) have been shown to be effective in enhancing expression (e.g. Gallie et al. *Nucl. Acids Res.* 15:8693–8711 (1987); Skuzeski et al. *Plant Molec. Biol.* 15:65–79 (1990))

IV. Targeting of the Gene Product Within the Cell

Various mechanisms for targeting gene products are known to exist in plants and the sequences controlling the functioning of these mechanisms have been characterized in some detail. For example, the targeting of gene products to the chloroplast is controlled by a signal sequence found at the amino terminal end of various proteins and that is cleaved during chloroplast import yielding the mature protein (e.g. Comai et al. *J. Biol. Chem.* 263:15104–15109 (1988)). These signal sequences can be fused to heterologous gene products to effect the import of heterologous products into the chloroplast (van den Broeck et al, *Nature* 313:358–363 (1985)). DNA encoding for appropriate signal sequences can be isolated from the 5' end of the cDNAs encoding the RUBISCO protein, the CAB protein, the EPSP synthase enzyme, the GS2 protein and many other proteins that are known to be chloroplast localized.

Other gene products are localized to other organelles such as the mitochondrion and the peroxisome (e.g. Unger et al. *Plant Molec. Biol.* 13:411–418 (1989)). The cDNAs encoding these products can also be manipulated to effect the targeting of heterologous gene products to these organelles. Examples of such sequences are the nuclear-encoded ATPases and specific aspartate amino transferase isoforms for mitochondria. Targeting to cellular protein bodies has been described by Rogers et al., *Proc. Natl. Acad. Sci. USA* 82:6512–6516 (1985)).

In addition, sequences have been characterized that cause the targeting of gene products to other cell compartments. Amino terminal sequences are responsible for targeting to the ER, the apoplast, and extracellular secretion from aleurone cells (Koehler & Ho, *Plant Cell* 2:769–783 (1990)). Additionally, amino terminal sequences in conjunction with carboxy terminal sequences are responsible for vacuolar targeting of gene products (Shinshi et al., *Plant Molec. Biol.* 14:357–368 (1990)).

By the fusion of the appropriate targeting sequences described above to transgene sequences of interest it is possible to direct the transgene product to any organelle or cell compartment. For chloroplast targeting, for example, the chloroplast signal sequence from the RUBISCO gene, the CAB gene, the EPSP synthase gene, or the GS2 gene is fused in frame to the amino terminal ATG of the transgene. The signal sequence selected should include the known cleavage site and the fusion constructed should take into account any amino acids after the cleavage site that are required for cleavage. In some cases this requirement may be fulfilled by the addition of a small number of amino acids between the cleavage site and the transgene ATG or alternatively replacement of some amino acids within the transgene sequence. Fusions constructed for chloroplast import can be tested for efficacy of chloroplast uptake by in vitro translation of in vitro transcribed constructions followed by in vitro chloroplast uptake using techniques described by (Bartlett et al. In: Edelmann et al. (Eds.) *Methods in Chloroplast Molecular Biology,* Elsevier. pp. 1081–1091 (1982); Wasmann et al. *Mol Gen. Genet.* 205:446–453 (1986)). These construction techniques are well known in the art and are equally applicable to mitochondria and peroxisomes. The choice of targeting that may be required for expression of the transgenes will depend on the cellular localization of the precursor required as the starting point for a given pathway. This will usually be cytosolic or chloroplastic, although it may is some cases be mitochondrial or peroxisomal. The products of transgene expression will not normally require targeting to the ER, the apoplast or the vacuole.

The above described mechanisms for cellular targeting can be utilized in conjunction with plant protox promoters so as to effect a specific cell targeting goal under the transcriptional regulation of a promoter that has an expression pattern different to that of the promoter from which the targeting signal derives.

Example 7

Transformation of Dicotyledons

Transformation techniques for dicotyledons are well known in the art and include Agrobacterium-based techniques and techniques that do not require Agrobacterium. Non-Agrobacterium techniques involve the uptake of exogenous genetic material directly by protoplasts or cells. This can be accomplished by PEG or electroporation mediated uptake, particle bombardment-mediated delivery, or microinjection. Examples of these techniques are described by Paszkowski et al., *EMBO J* 3:2717–2722 (1984), Potrykus et al., *Mol. Gen. Genet.* 199:169–177 (1985), Reich et al, *Biotechnology* 4:1001–1004 (1986), and Klein et al, *Nature* 327:70–73 (1987). In each case the transformed cells are regenerated to whole plants using standard techniques known in the art.

Agrobacterium-mediated transformation is a preferred technique for transformation of dicotyledons because of its high efficiency of transformation and its broad utility with many different species. The many crop species that are routinely transformable by Agrobacterium include tobacco, tomato, sunflower, cotton, oilseed rape, potato, soybean, alfalfa and poplar (EP 0 317 511 (cotton), EP 0 249 432 (tomato, to Calgene), WO 87/07299 (Brassica, to Calgene), U.S. Pat. No. 4,795,855 (poplar)).

Transformation of the target plant species by recombinant Agrobacterium usually involves co-cultivation of the Agrobacterium with explants from the plant and follows protocols well known in the art. Transformed tissue is regenerated on selectable medium carrying the antibiotic or herbicide resistance marker present between the binary plasmid T-DNA borders.

Example 8

Transformation of Monocotyledons

Transformation of most monocotyledon species has now also become routine. Preferred techniques include direct gene transfer into protoplasts using PEG or electroporation techniques, and particle bombardment into callus tissue. Transformations can be undertaken with a single DNA species or multiple DNA species (i.e. co-transformation) and both these techniques are suitable for use with this invention. Co-transformation may have the advantage of avoiding complex vector construction and of generating transgenic plants with unlinked loci for the gene of interest and the selectable marker, enabling the removal of the selectable marker in subsequent generations, should this be regarded desirable. However, a disadvantage of the use of co-transformation is the less than 100% frequency with which separate DNA species are integrated into the genome (Schocher et al. *Biotechnology* 4:1093–1096 (1986)).

Patent Applications EP 0 292 435 (to Ciba-Geigy), EP 0 392 225 (to Ciba-Geigy), WO 93/07278 (to Ciba-Geigy) and U.S. Pat. No. 5,350,689 (to Ciba-Geigy) describe techniques for the preparation of callus and protoplasts from an élite inbred line of maize, transformation of protoplasts using PEG or electroporation, and the regeneration of maize plants from transformed protoplasts. Gordon-Kamm et al., *Plant Cell* 2:603–618 (1990)) and Fromm et al., *Biotechnology* 8:833–839 (1990)) have published techniques for transformation of A188-derived maize line using particle bombardment. Furthermore, application WO 93/07278 (to Ciba-Geigy) and Koziel et al., *Biotechnology* 11:194–200 (1993)) describe techniques for the transformation of élite inbred lines of maize by particle bombardment. This technique utilizes immature maize embryos of 1.5–2.5 mm length excised from a maize ear 14–15 days after pollination and a PDS-1000He Biolistics device for bombardment.

Transformation of rice can also be undertaken by direct gene transfer techniques utilizing protoplasts or particle bombardment. Protoplast-mediated transformation has been described for Japonica-types and Indica-types (Zhang et al., *Plant Cell Rep* 7:379–384 (1988); Shimamoto et al. *Nature* 338:274–277 (1989); Datta et al. *Biotechnology* 8:736–740 (1990)). Both types are also routinely transformable using particle bombardment (Christou et al. *Biotechnology* 9:957–962 (1991)).

Patent Application EP 0 332 581 (to Ciba-Geigy) describes techniques for the generation, transformation and regeneration of Pooideae protoplasts. These techniques allow the transformation of Dactylis and wheat. Furthermore, wheat transformation was been described by Vasil et al., *Biotechnology* 10:667–674 (1992)) using particle bombardment into cells of type C long-term regenerable callus, and also by Vasil et al., *Biotechnology* 11:1553–1558 (1993)) and Weeks et al, *Plant Physiol.* 102:1077–1084 (1993) using particle bombardment of immature embryos and immature embryo-derived callus. A preferred technique for wheat transformation, however, involves the transformation of wheat by particle bombardment of immature embryos and includes either a high sucrose or a high maltose step prior to gene delivery. Prior to bombardment, any number of embryos (0.75–1 mm in length) are plated onto MS medium with 3% sucrose (Murashige & Skoog, *Physiologia Plantarum* 15:473–497 (1962)) and 3 mg/l 2,4-D for induction of somatic embryos, which is allowed to proceed in the dark. On the chosen day of bombardment, embryos are removed from the induction medium and placed onto the osmoticum (i.e. induction medium with sucrose or maltose added at the desired concentration, typically 15%). The embryos are allowed to plasmolyze for 2–3 h and are then bombarded. Twenty embryos per target plate is typical, although not critical. An appropriate gene-carrying plasmid (such as pCIB3064 or pSG35) is precipitated onto micrometer size gold particles using standard procedures. Each plate of embryos is shot with the DuPont Biolistics helium device using a burst pressure of ~1000 psi using a standard 80 mesh screen. After bombardment, the embryos are placed back into the dark to recover for about 24 h (still on osmoticum). After 24 hrs, the embryos are removed from the osmoticum and placed back onto induction medium where they stay for about a month before regeneration. Approximately one month later the embryo explants with developing embryogenic callus are transferred to regeneration medium (MS+1 mg/liter NAA, 5 mg/liter GA), further containing the appropriate selection agent (10 mg/l basta in the case of pCIB3064 and 2 mg/l methotrexate in the case of pSOG35). After approximately one month, developed shoots are transferred to larger sterile containers known as "GA7s," which contained half-strength MS, 2% sucrose, and the same concentration of selection agent. WO94/13822 describes methods for wheat transformation and is hereby incorporated by reference.

Example 9
Construction of Plant Transformation Vectors Expressing Altered Protox-1 Genes Behind the Native Maize Protox-1 Promoter The 3848 bp maize genomic fragment (SEQ ID NO:14) is excised from the isolated lambda phage clone as a SalI-KpnI partial digest product and ligated to a KpnI-NotI fragment derived from an altered maize Protox-1 cDNA that contains an alanine to leucine change at amino acid 164 (SEQ ID NO:6) This creates a fusion of the native maize Protox-1 promoter to a full length cDNA that has been shown to confer herbicide tolerance in a bacterial system (see copending U.S. patent application Ser. No. 08/808,931 entitled "DNA Molecules Encoding Plant Protoporphyrinogen Oxidase and Inhibitor Resistant Mutants Thereof", Examples 8–13). This fusion is cloned into a pUC18 derived vector containing the CaMV 35S terminator sequence to create a protox promoter/altered protox cDNA/terminator cassette. The plasmid containing this cassette is designated pWCo-1.

A second construct for maize transformation is created by engineering the first intron found in the coding sequence from the maize genomic clone back into the maize cDNA. The insertion is made using standard overlapping PCR fusion techniques. The intron (SEQ ID NO:25) is 93 bp long and is inserted between nucleotides 203 and 204 of SEQ ID NO:5, exactly as it appeared in natural context in the lambda clone described in Example 4. This intron-containing version of the expression cassette is designated pWCo-2.

Example 10
Demonstration of Maize Protox-1 Promoter Activity in Transgenic Maize Plants Maize plants transformed with maize protox promoter/altered protox fusions were identified using PCR analysis with primers specific for the transgene. Total RNA was prepared from the PCR positive plants and reverse-transcribed using Superscript M-MLV (Life Technologies) under recommended conditions. Two microliters of the reverse transcription reaction was used in a PCR reaction designed to be specific for the altered protox sequence. While untransformed controls give no product in this reaction, approximately 85% of plants transformed with pWCo-1 gave a positive result, indicating the presence of mRNA derived from the transgene. This demonstrates some level of activity for the maize protox promoter. The RNA's from the transgenic maize plants were also subjected to standard northern blot analysis using the radiolabeled maize protox cDNA fragment from SEQ ID NO:5 as a probe. Protox-1 mRNA levels significantly above those of untransformed controls were detected in some of the transgenic maize plants. This elevated mRNA level is presumed to be due to expression of altered protox-1 mRNA from the cloned maize protox promoter.

Example 11
Isolation of a Sugar Beet Protox-1 Promoter Sequence

A genomic sugar beet library was prepared by Stratagene in the Lambda Fix II vector. Approximately 300,000 pfu of the library was plated and probed with the sugar beet protox-1 cDNA sequence (SEQ ID NO:17) as described for maize in Example 4. Analysis by restriction digest, hybridization patterns and DNA sequence analysis identified a lambda clone containing approximately 7 kb of sugar beet genomic DNA located 5' to the sugar beet coding sequence previously isolated as a cDNA clone. A PstI-SalI fragment of 2606 bb was subcloned from the lambda clone into a pBluescript vector. This fragment contains 2068 bp of 5' noncoding sequence and includes the sugar beet protox-1 promoter sequence. It also includes the first 453 bp of the protox-1 coding sequence and the 85 bp first intron contained in the coding sequence. The sequence of this fragment is set forth in SEQ ID NO:26.

A plasmid containing the sequence of SEQ ID NO:26 was deposited Dec. 6, 1996 pWDC-20 (NRRL #B-21650).

Example 12
Construction of Plant Transformation Vectors Expressing Altered Sugar Beet Protox-1 Genes Behind the Native Sugar Beet Protox-1 Promoter The sugar beet genomic fragment (SEQ ID NO:26) was excised from the genomic subclone described in Example 11 as a SacI-BsrGI fragment that includes 2068 bp of 5' noncoding sequence and the first 300 bp of the sugar beet Protox-1 coding sequence. This fragment was ligated to a BsrGI-NotI fragment derived from an altered sugar beet Protox-1 cDNA that contained a tyrosine to methionine change at amino acid 449 (SEQ ID NO:18). This created a fusion of the native sugar beet Protox-1 promoter to a full length cDNA that had been shown to confer herbicide tolerance in a bacterial system (Co-pending application Ser. No. 08/808,931. This fusion was cloned into a pUC18 derived vector containing the CaMV 35S terminator sequence to create a protox promoter/altered protox cDNA/terminator cassette. The plasmid containing this cassette was designated pWCo-3.

Example 13
Production of Herbicide Tolerant Plants by Expression of a Native Sugar Beet Protox-1 Promoter/Altered Sugar Beet Protox-1 Fusion The expression cassette from pWCo-3 is transformed into sugar beet using any of the transformation methods applicable to dicot plants, including Agrobacterium, protoplast, and biolistic transformation techniques. Transgenic sugar beets expressing the altered protox-1 enzyme are identified by RNA-PCR and tested for tolerance to protox-inhibiting herbicides at concentrations that are lethal to untransformed sugar beets.

While the present invention has been described with reference to specific embodiments thereof, it will be appreciated that numerous variations, modifications, and embodiments are possible, and accordingly, all such variations, modifications and embodiments are to be regarded as being within the spirit and scope of the present invention.

What is claimed is:

1. An isolated DNA molecule comprising any one of SEQ ID NO:13, SEQ ID NO:14, or SEQ ID NO:26.
2. The isolated DNA molecule of claim 1, wherein said DNA molecule comprises SEQ ID NO:13.
3. The isolated DNA molecule of claim 1, wherein said DNA molecule comprises SEQ ID NO:14.
4. The isolated DNA molecule of claim 1, wherein said DNA molecule comprises SEQ ID NO:26.
5. A chimeric gene comprising the DNA molecule of claim 2.
6. A chimeric gene comprising the DNA molecule of claim 3.
7. A chimeric gene comprising the DNA molecule of claim 4.
8. A vector comprising the DNA molecule of claim 2.
9. A vector comprising the DNA molecule of claim 3.
10. A vector comprising the DNA molecule of claim 4.
11. A host cell comprising the chimeric gene of claim 5.
12. A host cell comprising the chimeric gene of claim 6.
13. A host cell comprising the chimeric gene of claim 7.
14. The host cell of claim 11, wherein said host cell is a plant cell.
15. The host cell of claim 12, wherein said host cell is a plant cell.
16. The host cell of claim 13, wherein said host cell is a plant cell.
17. A plant comprising a plant cell of claim 14.
18. A plant comprising a plant cell of claim 15.
19. A plant comprising a plant cell of claim 16.

* * * * *